US007867727B2

(12) United States Patent
Hageman

(10) Patent No.: US 7,867,727 B2
(45) Date of Patent: Jan. 11, 2011

(54) METHODS AND REAGENTS FOR TREATMENT AND DIAGNOSIS OF VASCULAR DISORDERS AND AGE-RELATED MACULAR DEGENERATION

(75) Inventor: Gregory S. Hageman, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 11/894,667

(22) Filed: Aug. 20, 2007

(65) Prior Publication Data

US 2008/0152659 A1 Jun. 26, 2008

Related U.S. Application Data

(63) Continuation of application No. PCT/US2007/073514, filed on Jul. 13, 2007.

(60) Provisional application No. 60/831,018, filed on Jul. 13, 2006, provisional application No. 60/840,073, filed on Aug. 23, 2006.

(51) Int. Cl.
C12Q 1/48 (2006.01)
C12Q 1/68 (2006.01)
G01N 33/53 (2006.01)

(52) U.S. Cl. .......................... 435/7.92; 435/6

(58) Field of Classification Search ...................... None
See application file for complete search history.

(56) References Cited

U.S. PATENT DOCUMENTS

| 5,474,796 A | 12/1995 | Brennan |
| 2002/0015957 A1 | 2/2002 | Hageman et al. |
| 2004/0170633 A1 | 9/2004 | Taylor et al. |
| 2008/0146501 A1 | 6/2008 | Hageman et al. |
| 2008/0261211 A1 | 10/2008 | Allikmets et al. |
| 2008/0280825 A1 | 11/2008 | Hageman et al. |
| 2009/0017029 A1* | 1/2009 | Hoh et al. ................. 424/137.1 |
| 2009/0312394 A1* | 12/2009 | Hughes .................... 514/44 A |

FOREIGN PATENT DOCUMENTS

| WO | WO 2007/056111 A1 | 5/2007 |
| WO | WO 2007/144621 A2 | 12/2007 |

OTHER PUBLICATIONS

Abrera-Abeleda, M.A., et al., "Variations in the complement regulatory genes factor H (CFH) and factor H related 5 (CFHR5) are associated with membranoproliferative glomerulonephritis type II (dense deposit disease)," *J. Med. Genet*, 43:582-589, 2006, E-Publication Nov. 18, 2005.
Boerhinger Mannheim, "Non-Radioactive Labeling and Detection of Nucleric Acids," *1997 Biochemical Catalog*, cover page and p. 65.
Despriet, D., et al, "Complement Factor H Polymorphism Complement Activators, and Risk of Age-Related Macular Degeneration," *JAMA*, Jul. 19, 2006 vol. 296, pp. 301-309.
Dragon-Durey, M., et al., Heterozygous and Homozygous Factor H Deficiencies Associated with Hemolytic Uremic Syndrome or Membranoproliferative Glomerulonephritis: Report and Genetic Analysis of 16 Cases, *J Am Soc Nephrol*. (2004) 15:787-795.
Edwards et al., "Complement Factor H Polymorphism in Age-Relaged Macular Degeneration," *Science*, 308:421-424, Apr. 15, 2005.
Francis, Peter J., "Haplotypes in the Complement Factor H (CFH) Gene: Associations with Drusen and Advanced Age-Related Macular Degeneration," *PloS One*, 2007 vol. 2, pp. 1-6.
Gotoh, N. et al., "No association between complement factor H gene polymorphism and exudative age-related macular degeneration in Japanese," *Human Genetics*, 2006, 120:139-143.
Hageman et al., "A common haplotype in the complement regulatory gene factor H (HF1/CFH) predisposes individuals to age-related macular degeneration," *PNAS*, 102:20: 7227-7232, May 17, 2005.
Haines et al, "Complement Factor H Variant Increases the Risk of Age-Related Macular Degeneration," *Science*, 308:419-421, Apr. 15, 2005.
Hughes, Anne E., et al, "A common CFH haplotype of CFHR1 and CFHR3, is associated with the lower risk of age-related macular degeneration," *Nature Genetics*, Oct. 2006 (E publication Sep. 24, 2006), vol. 38, pp. 1173-1178.
PCT Search Report for application No. PCT/US07/73514 of Aug. 13, 2008.
Written Opinion for application No. PCT/US07/73514 of Aug. 13, 2008.
EP 07812932.7 European Supplementary Search Report completed Sep. 16, 2009.
Heinen et al, "De Novo Gene Conversion in the RCA Gene Cluster (1q32) Causes Mutations in Complement Factor H Associated with Atypical Hemolytic Uremic Syndrome," *Human Mutation*, 27(3):292-293 (2006).
Perez-Caballero et al., "Clustering of Missense Mutations in the C-Terminal Region of Factor H in Atypical Hemolytic Uremic Syndrome," *American Journal of Human Genetics*, 68(2):478-484 (2001).
Klein et al., "Complement Factor H Polymorphism in Age-Related Macular Degeneration," *Science*, 308:385-389, Apr. 15, 2005.
Li, M. et al., "CFH haplotypes without the Y402H coding variant show strong association with susceptibility to age-related macular degeneration," *Nature Genetics*, Sep. 2006, vol. 38, No. 9, pp. 1049-1054.

(Continued)

Primary Examiner—Lisa J Hobbs
(74) Attorney, Agent, or Firm—Townsend and Townsend and Crew LLP

(57) ABSTRACT

Disclosed are screening methods for determining a human subject's propensity to develop a vascular disorder and/or age-related macular degeneration (AMD), therapeutic or prophylactic compounds for treating disease or inhibiting its development, and methods of treating patients to alleviate symptoms of the disease, prevent or delay its onset, or inhibit its progression. The inventions are based on the discovery that persons with a genome having a deletion of the CFHR-1 and/or CFHR-3 gene, which normally lie on human chromosome 1 between DNA encoding CFH and CFHR-4, are at reduced risk of developing AMD, and elevated risk of developing vascular disease such as aneurysm.

30 Claims, 16 Drawing Sheets

OTHER PUBLICATIONS

Magnusson, K. P., et al., "CFH Y402H Confers Similar Risk of Soft Drusen and Both Forms of Advanced AMD," *PLoS Medicine*, vol. 3, Issue e5, pp. 109-113.

Mullins, R., et al., "Structure and composition of drusen associated with glomerulonephritis: Implications for the role of complement activation in drusen biogenesis", *Eye* (2001) 15:390-395.

Nicaud, V. et al., "Lack of association between complement factor H polymorphisms and coronary artery disease or myocardial infarction," *Journal of Molecular Medicine*, 2007, 85:771-775.

Reference SNP Cluster Report: rs641153 available at http://www.ncbi.nlm.nih.gov/projects/SNP.

Tedeschi-Blok, N. et al., "Population-Based Study of Early Age-Related Macular Degeneration, Role of the Complement Factor H Y402H Polymorphism in Bilateral but Not Unilateral Disease," *Ophthalmology*, Jan. 2007, 114:99-103.

PCT Search Report for application No. PCT/US07/03696 of Jun. 12, 2008.

Written Opinion for application No. PCT/US07/03696 of Jun. 12, 2008.

PCT Search Report for application No. PCT/US07/03904 of Aug. 1, 2008.

Written Opinion for application No. application PCT/US07/03904 of Aug. 1, 2008.

\* cited by examiner

```
H Factor AA seq    1 MRLLAKIICLMLWAICVAEDCNELPPRRNTEILTGSWSDQTYPEGTQAIY    50
CFHR1 AA seq.      1                                                          0
CHFR3 AA seq.      1                                                          0

H Factor AA seq   51 KCRPGYRSLGNVIMVCRKGEWVALNPLRKCQKRPCGHPGDTPFGTFTLTG   100
CFHR1 AA seq.      1                                                          0
CHFR3 AA seq.      1                                                          0

H Factor AA seq  101 GNVFEYGVKAVYTCNEGYQLLGEINYRECDTDGWTNDIPICEVVKCLPVT   150
CFHR1 AA seq.      1                                                          0
CHFR3 AA seq.      1                                                          0

H Factor AA seq  151 APENGKIVSSAMEPDREYHFGQAVRFVCNSGYKIEGDEEMHCSDDGFWSK   200
CFHR1 AA seq.      1                                              MWLL         4
CHFR3 AA seq.      1                                              MLLL         4

H Factor AA seq  201 EKPKCVEISCKSPDVINGSPISQKIIYKENERFQYKCNMGYEYSERGDAV   250
CFHR1 AA seq.      5 VS-------------VILISRISS--------------------------  15
CHFR3 AA seq.      5 IN-------------VILTLWVSC--------------------------  15
                      **          .*

H Factor AA seq  251 CTESGWRPLPSCEEKSCDNPYIPNGDYSPLRIKHRTGDEITYQCRNGFYP   300
CFHR1 AA seq.     16 ------------------------------VGGEATF-----------   22
CHFR3 AA seq.     16 ------------------------------ANGQVKP-----------   22
                                                    . .

H Factor AA seq  301 ATRGNTAKCTSTGWIPAPRCTLKPCDYPDIKHGGLYHENMRRPYFPVAVG   350
CFHR1 AA seq.     23 --------------------CDFPKINHGILYDEEKYKPFSQVPTG      48
CHFR3 AA seq.     23 --------------------CDFPDIKHGGLFHENMRRPYFPVAVG      48
                                         **.* * ** *.*     .*.   *    *

H Factor AA seq  351 KYYSYYCDEHFETPSGSYWDHIHCTQDGWSPAVPCLRKCYFPYLENGYNQ   400
CFHR1 AA seq.     49 EVFYYSCEYNFVSPSKSFWTRITCTEEGWSPTPKCLRLCFFPFVENGHSE   98
CHFR3 AA seq.     49 KYYSYYCDEHFETPSGSYWDYIHCTQNGWSPAVPCLRKCYFPYLENGYNQ   98
                      . * .* .*  ** *.*   * **.  ***. *** *.**..***  .

H Factor AA seq  401 NHGRKFVQGKSIDVACHPGYALPKA-QTTVTCMENGWSPTPRCIRVKTCS   449
CFHR1 AA seq.     99 SSGQTHLEGDTVQIICNTGYRLQNN-ENNISCVERGWSTPP--------  138
CHFR3 AA seq.     99 NYGRKFVQGNSTEVACHPGYGLPKVRQTTVTCTENGWSPT---------  139
                     *.   ..* .  *. * * **   .....* *** *

H Factor AA seq  450 KSSIDIENGFISESQYTYALKEKAKYQCKLGYVTADGETSGSIRCGKDGW   499
CFHR1 AA seq.    139 -------------------------------------------------  138
CHFR3 AA seq.    140 -------------------------------------------------  139

H Factor AA seq  500 SAQPTCIKSCDIPVFMNARTKNDFTWFKLNDTLDYECHDGYESNTGSTTG   549
CFHR1 AA seq.    139 -------------------------------------------------  138
CHFR3 AA seq.    140 -------------------------------------------------  139

H Factor AA seq  550 SIVCGYNGWSDLPICYERECELPKIDVHLVPDRKKDQYKVGEVLKFSCKP   599
```

FIG. 6

```
CFHR1 AA seq.      139 -------------------------------------------------- 138
CHFR3 AA seq.      140 -------------------------------------------------- 139

H Factor AA seq    600 GFTIVGPNSVQCYHFGLSPDLPICKEQVQSCGPPPELLNGNVKEKTKEEY  649
CFHR1 AA seq.      139 -------------------------------------------------- 138
CHFR3 AA seq.      140 -------------------------------------------------- 139

H Factor AA seq    650 GHSEVVEYYCNPRFLMKGPNKIQCVDGEWTTLPVCIVEESTCGDIPELEH  699
CFHR1 AA seq.      139 -------------------------------------------------- 138
CHFR3 AA seq.      140 -------------------------------------------------- 139

H Factor AA seq    700 GWAQLSSPPYYYGDSVEFNCSESFTMIGHRSITCIHGVWTQLPQCVAIDK  749
CFHR1 AA seq.      139 -------------------------------------------------- 138
CHFR3 AA seq.      140 -------------------------------------------------- 139

H Factor AA seq    750 LKKCKSSNLIILEEHLKNKKEFDHNSNIRYRCRGKEGWIHTVCINGRWDP  799
CFHR1 AA seq.      139 --KCRST------------------------------------------- 143
CHFR3 AA seq.      140 --RCIR-------------------------------------------- 143
                           .*

H Factor AA seq    800 EVNCSMAQIQLCPPPPQIPNSHNMTTTLNYRDGEKVSVLCQENYLIQEGE  849
CFHR1 AA seq.      144 -------------------------------------------------- 143
CHFR3 AA seq.      144 -------------------------------------------------- 143

H Factor AA seq    850 EITCKDGRWQSIPLCVEKIPCSQPPQIEHGTINSSRSSQESYAHGTKLSY  899
CFHR1 AA seq.      144 -------------------------------------------------- 143
CHFR3 AA seq.      144 -------------------------------------------------- 143

H Factor AA seq    900 TCEGGFRISEENETTCYMGKWSSPPQCEGLPCKSPPEISHGVVAHMSDSY  949
CFHR1 AA seq.      144 -------------------------------------------------- 143
CHFR3 AA seq.      144 -------------------------------------------------- 143

H Factor AA seq    950 QYGEEVTYKCFEGFGIDGPAIAKCLGEKWSHPPSCIKTDCLSLPSFENAI  999
CFHR1 AA seq.      144 -------------------------------------------------- 143
CHFR3 AA seq.      144 -------------------------------------------------- 143

H Factor AA seq   1000 PMGEKKDVYKAGEQVTYTCATYYKMDGASNVTCINSRWTGRPTCRDTSCV 1049
CFHR1 AA seq.      144 ---------------------------------------------DTSCV 148
CHFR3 AA seq.      144 ---------------------------------------------DRTCS 148
                                                                    * .*

H Factor AA seq   1050 NPPTVQNAYIVSRQMSKYPSGERVRYQCRSPYEMFGDEE---VMCLNGNW 1096
CFHR1 AA seq.      149 NPPTVQNAYIVSRQMSKYPSGERVRYQCRSPYEMFGDEE---VMCLNGNW 195
CHFR3 AA seq.      149 KSDIEIENGFISESSSIYILNKEIQYKCKPGYATADGNSSGSITCLRNGW 198
                            .*    *  *      ..*.*.  *      . **  ..*
```

FIG. 6 (cont.)

```
H Factor AA seq  1097 TEPPQCKDSTGKCGPPPPIDNGDITSFPLSVYAPASSVEYQCQNLYQLEG 1146
CFHR1 AA seq.     196 TEPPQCKDSTGKCGPPPPIDNGDITSFPLSVYAPASSVEYQCQNLYQLEG  245
CHFR3 AA seq.     199 SAQPICINSSEKCGPPPPISNGDTTSFLLKVYVPQSRVEYQCQSYYELQG  248
                       . *  *  *. ******** *** *** * ** * * ******  *.*.*

H Factor AA seq  1147 NKRITCRNGQWSEPPKCLHPCVISREIMENYNIALRWTAKQKLYSRTGES 1196
CFHR1 AA seq.     246 NKRITCRNGQWSEPPKCLHPCVISREIMENYNIALRWTAKQKLYLRTGES  295
CHFR3 AA seq.     249 SNYVTCSNGEWSAPPRCIHPCIITEENMNKNNIKLKGRSDRKYYAKTGDT  298
                       .** **.** **.*.***.*. * *    ** *.  .  .* * .**..

H Factor AA seq  1197 VEFVCKRGYRLSSRSHTLRTTCWDGKLEYPTCAKR 1231
CFHR1 AA seq.     296 AEFVCKRGYRLSSRSHTLRTTCWDGKLEYPTCAKR  330
CHFR3 AA seq.     299 IEFMCKLGYNANTSILSFQAVCREGIVEYPRCE    331
                       **.** **    .  . .. * .* .*** *
```

FIG. 6 (cont.)

```
H Factor mRNA      1  ATGAGACTTCTAGCAAAGATTATTTGCCTTATGTTATGGGCTATTTGTGT  50
CFHR1 mRNA      .  1                                                      0
CFHR3 mRNA         1                                                      0

H Factor mRNA     51  AGCAGAAGATTGCAATGAACTTCCTCCAAGAAGAAATACAGAAATTCTGA  100
CFHR1 mRNA      .  1                                                      0
CFHR3 mRNA         1                                                      0

H Factor mRNA    101  CAGGTTCCTGGTCTGACCAAACATATCCAGAAGGCACCCAGGCTATCTAT  150
CFHR1 mRNA      .  1                                                      0
CFHR3 mRNA         1                                                      0

H Factor mRNA    151  AAATGCCGCCCTGGATATAGATCTCTTGGAAATGTAATAATGGTATGCAG  200
CFHR1 mRNA      .  1                                                      0
CFHR3 mRNA         1                                                      0

H Factor mRNA    201  GAAGGGAGAATGGGTTGCTCTTAATCCATTAAGGAAATGTCAGAAAAGGC  250
CFHR1 mRNA      .  1                                                      0
CFHR3 mRNA         1                                                      0

H Factor mRNA    251  CCTGTGGACATCCTGGAGATACTCCTTTTGGTACTTTTACCCTTACAGGA  300
CFHR1 mRNA      .  1                                                      0
CFHR3 mRNA         1                                                      0

H Factor mRNA    301  GGAAATGTGTTTGAATATGGTGTAAAAGCTGTGTATACATGTAATGAGGG  350
CFHR1 mRNA      .  1                                                      0
CFHR3 mRNA         1                                                      0

H Factor mRNA    351  GTATCAATTGCTAGGTGAGATTAATTACCGTGAATGTGACACAGATGGAT  400
CFHR1 mRNA      .  1                                                      0
CFHR3 mRNA         1                                                      0

H Factor mRNA    401  GGACCAATGATATTCCTATATGTGAAGTTGTGAAGTGTTTACCAGTGACA  450
CFHR1 mRNA      .  1                                                      0
CFHR3 mRNA         1                                                      0

H Factor mRNA    451  GCACCAGAGAATGGAAAAATTGTCAGTAGTGCAATGGAACCAGATCGGGA  500
CFHR1 mRNA      .  1                                                      0
CFHR3 mRNA         1                                                      0

H Factor mRNA    501  ATACCATTTTGGACAAGCAGTACGGTTTGTATGTAACTCAGGCTACAAGA  550
CFHR1 mRNA      .  1                                                      0
CFHR3 mRNA         1                                                      0
```

FIG. 7

```
H Factor mRNA    551 TTGAACGAGATGAAGAAATGCATTGTTCAGACGATGGTTTTTGGAGTAAA  600
CFHR1 mRNA         1                                                       0
CFHR3 mRNA         1                                                       0

H Factor mRNA    601 GAGAAACCAAAGTGTGTCGAAATTTCATGCAAATCCCCAGATGTTATAAA  650
CFHR1 mRNA         1                                                       0
CFHR3 mRNA         1                                                       0

H Factor mRNA    651 TGGATCTCCTATATCTCAGAAGATTATTTATAAGGAGAATGAACGATTTC  700
CFHR1 mRNA         1                                                       0
CFHR3 mRNA         1                                                       0

H Factor mRNA    701 AATATAAATGTAACATGGGTTATGAATACAGTGAAAGAGGAGATGCTGTA  750
CFHR1 mRNA         1                                                       0
CFHR3 mRNA         1                                                       0

H Factor mRNA    751 TGCACTGAATCTGGATGCCGTCCGTTGCCTTCATGTGAACAAAAATCATG  800
CFHR1 mRNA         1                                                       0
CFHR3 mRNA         1                                                       0

H Factor mRNA    801 TGATAATCCTTATATTCCAAATGGTGACTACTCACCTTTAAGGATTAAAC  850
CFHR1 mRNA         1                                                       0
CFHR3 mRNA         1                                                       0

H Factor mRNA    851 ACAGAACTGGAGATGAAATCACGTACCAGTGTAGAAATGGTTTTTATCCT  900
CFHR1 mRNA         1                                                       0
CFHR3 mRNA         1                                                       0

H Factor mRNA    901 GCAACCCGGGGAAATACAGCCAAATGCACAAGTACTGGCTGGATACCTGC  950
CFHR1 mRNA         1                                                       0
CFHR3 mRNA         1                                                       0

H Factor mRNA    951 TCCGACATGTACCTTGAAACCTTGTGATTATCCAGACATTAAACATGGAG 1000
CFHR1 mRNA         1                                                       0
CFHR3 mRNA         1                                                       0

H Factor mRNA   1001 GTCTATATCATGAGAATATGCGTAGACCATACTTTCCAGTAGCTGTAGGA 1050
CFHR1 mRNA         1                                                       0
CFHR3 mRNA         1                                                       0

H Factor mRNA   1051 AAATATTACTCCTATTACTGTGATGAACATTTTGAGACTCCGTCAGGAAG 1100
CFHR1 mRNA         1                                                       0
CFHR3 mRNA         1                                                       0
```

FIG. 7 (cont.)

```
H Factor mRNA    1101 TTACTGGGATCACATTCATTGCACACAAGATGGATGGTCGCCAGCAGTAC 1150
CFHR1 mRNA          .    1                                                       0
CFHR3 mRNA               1                                                       0

H Factor mRNA    1151 CATGCCTCAGAAAATGTTATTTTCCTTATTTGGAAAATGGATATAATCAA 1200
CFHR1 mRNA          .    1                                                       0
CFHR3 mRNA               1                                                       0

H Factor mRNA    1201 AATCATCCAACAAACTTTCTACACCCTAAATCTATACACCTTCCCTCCCA 1250
CFHR1 mRNA          .    1                                                       0
CFHR3 mRNA               1                                                       0

H Factor mRNA    1251 TCCTGGCTACGCTCTTCCAAAAGCGCAGACCACAGTTACATGTATGGAGA 1300
CFHR1 mRNA          .    1                                                       0
CFHR3 mRNA               1                                                       0

H Factor mRNA    1301 ATGGCTGGTCTCCTACTCCCAGATGCATCCGTGTCAAAACATGTTCCAAA 1350
CFHR1 mRNA          .    1                                                       0
CFHR3 mRNA               1                                                       0

H Factor mRNA    1351 TCAACTATACATATTCACAATCCCTTTATTTCTCAATCTCACTATACATA 1400
CFHR1 mRNA          .    1                                                       0
CFHR3 mRNA               1                                                       0

H Factor mRNA    1401 TGCCTTAAAAGAAAAAGCGAAATATCAATGCAAACTAGGATATGTAACAG 1450
CFHR1 mRNA          .    1                                                       0
CFHR3 mRNA               1                                                       0

H Factor mRNA    1451 CAGATGGTGAAACATCAGGATCAATTAGATGTGGGAAAGATGGATGGTCA 1500
CFHR1 mRNA          .    1                                                       0
CFHR3 mRNA               1                                                       0

H Factor mRNA    1501 GCTCAACCCACGTGCATTAAATCTTGTGATATCCCAGTATTTATGAATGC 1550
CFHR1 mRNA          .    1                                                       0
CFHR3 mRNA               1                                                       0

H Factor mRNA    1551 CAGAACTAAAAATGACTTCACATGGTTTAAGCTGAATGACACATTGGACT 1600
CFHR1 mRNA          .    1                                                       0
CFHR3 mRNA               1                                                       0

H Factor mRNA    1601 ATGAATGCCATGATGGTTATGAAAGCAATACTGGAAGCACCACTGGTTCC 1650
CFHR1 mRNA          .    1                                                       0
CFHR3 mRNA               1                                                       0
```

FIG. 7 (cont.)

```
H Factor mRNA    1651 ATAGTGTGTGGTTACAATGGTTGGTCTGATTTACCCATATGTTATGAAAG 1700
CFHR1 mRNA    .     1                                                      0
CFHR3 mRNA          1                                                      0

H Factor mRNA    1701 AGAATGCGAACTTCCTAAAATAGATGTACACTTAGTTCCTGATCGCAAGA 1750
CFHR1 mRNA    .     1                                                      0
CFHR3 mRNA          1                                                      0

H Factor mRNA    1751 AAGACCAGTATAAAGTTGGAGAGGTGTTGAAATTCTCCTGCAAACCAGGA 1800
CFHR1 mRNA    .     1                                                      0
CFHR3 mRNA          1                                                      0

H Factor mRNA    1801 TTTACAATACTTCCACCTAATTCCCTTCACTCCTACCACTTTCCATTCTC 1850
CFHR1 mRNA    .     1                                                      0
CFHR3 mRNA          1                                                      0

H Factor mRNA    1851 TCCTGACCTCCCAATATGTAAAGAGCAAGTACAATCATGTGGTCCACCTC 1900
CFHR1 mRNA    .     1                                                      0
CFHR3 mRNA          1                                                      0

H Factor mRNA    1901 CTGAACTCCTCAATGGGAATGTTAAGGAAAAAACGAAAGAAGAATATGGA 1950
CFHR1 mRNA    .     1                                                      0
CFHR3 mRNA          1                                                      0

H Factor mRNA    1951 CACAGTGAAGTGGTGGAATATTATTGCAATCCTAGATTTCTAATGAAGGG 2000
CFHR1 mRNA    .     1                                                      0
CFHR3 mRNA          1                                                      0

H Factor mRNA    2001 ACCTAATAAAATTCAATGTGTTGATGGAGAGTGGACAACTTTACCAGTGT 2050
CFHR1 mRNA    .     1                                                      0
CFHR3 mRNA          1                                                      0

H Factor mRNA    2051 GTATTGTGGAGGAGAGTACCTGTGGAGATATACCTGAACTTGAACATGGC 2100
CFHR1 mRNA    .     1                                                      0
CFHR3 mRNA          1                                                      0

H Factor mRNA    2101 TGGGCCCAGCTTTCTTCCCCTCCTTATTACTATGGAGATTCAGTGGAATT 2150
CFHR1 mRNA    .     1                                                      0
CFHR3 mRNA          1                                                      0

H Factor mRNA    2151 CAATTGCTCACAATCATTTACAATCATTCCACACACATCAATTACCTCTA 2200
CFHR1 mRNA    .     1                                                      0
CFHR3 mRNA          1                                                      0
```

FIG. 7 (cont.)

```
H Factor mRNA    2201 TTCATGGAGTATGGACCCAACTTCCCCAGTGTGTGGCAATAGATAAACTT 2250
CFHR1  mRNA        1                                                    0
CFHR3  mRNA        1                                                    0

H Factor mRNA    2251 AAGAAGTGCAAATCATCAAATTTAATTATACTTGAGGAACATTTAAAAAA 2300
CFHR1  mRNA        1                                                    0
CFHR3  mRNA        1                                                    0

H Factor mRNA    2301 CAAGAAGGAATTCGATCATAATTCTAACATAAGGTACAGATGTAGAGGAA 2350
CFHR1  mRNA        1                                                    0
CFHR3  mRNA        1                                                    0

H Factor mRNA    2351 AAGAAGGATGGATACACACAGTCTGCATAAATGGAAGATGGGATCCAGAA 2400
CFHR1  mRNA        1                                                    0
CFHR3  mRNA        1                                                    0

H Factor mRNA    2401 GTGAACTGCTCAATGGCACAAATACAATTATGCCCACCTCCACCTCAGAT 2450
CFHR1  mRNA        1                                                    0
CFHR3  mRNA        1                                                    0

H Factor mRNA    2451 TCCCAATTCTCACAATATGACAACCACACTGAATTATCGGGATGGAGAAA 2500
CFHR1  mRNA        1                                                    0
CFHR3  mRNA        1                                                    0

H Factor mRNA    2501 AACTATCTCTTCTTTCCCAACAAAATTATCTAATTCACCAACCACAACAA 2550
CFHR1  mRNA        1                                                    0
CFHR3  mRNA        1                                                    0

H Factor mRNA    2551 ATTACATGCAAAGATGGAAGATGGCAGTCAATACCACTCTGTGTTGAAAA 2600
CFHR1  mRNA        1                                                    0
CFHR3  mRNA        1                                                    0

H Factor mRNA    2601 AATTCCATGTTCACAACCACCTCAGATAGAACACGGAACCATTAATTCAT 2650
CFHR1  mRNA        1                                                    0
CFHR3  mRNA        1                                                    0

H Factor mRNA    2651 CCAGGTCTTCACAAGAAAGTTATGCACATGGGACTAAATTGAGTTATACT 2700
CFHR1  mRNA        1                 ATGTGGCTCCTGGTCAGTGTAATTCTAAT       29
CFHR3  mRNA        1                 ATGTTGTTACTAATCAATGTCATTCTGAC       29
                                      ***   *    * ***    **  *

H Factor mRNA    2701 TGTGACGGTGGTTTCAGGATATCTGAAGAAAATGAAACAACATGCTACAT 2750
CFHR1  mRNA       30 CTCACGGATATCCTCTG-----TTCGGGGAGAAGCAACATTTTCTGATTT   74
CFHR3  mRNA       30 CTTCTCCGTTTCCTCTG-----CTAATCCACAACTCAAACCTTCTCATTT   74
                     **  *   *   *         *      *   **   **  * *
```

FIG. 7 (cont.)

```
H Factor mRNA   2751 GGGAAAATGGAGTTCTCCACCTCAGTGTGAAGGCCTTCCTTGTAAATCTC 2800
CFHR1 mRNA       75 TCCAAAAATAAACCATGGAATTCTATATGATGAAGAAAAATATAAGCCAT  124
CFHR3 mRNA       75 TCCAGACATTAAACATGGAGGTCTATTTCATGACAATATGCGTAGACCAT  124
                    *  *    *    * * **  * **** *       * *   **    *

H Factor mRNA   2801 CACCTGAGATTTCTCATGCTGTTGTAGCTCACATGTCAGACAGTTATCAG 2850
CFHR1 mRNA      125 TTTCCCAGGTTCCTACAGGGGAAGTTTTCTA------------TTACTCC  162
CFHR3 mRNA      125 ACTTTCCAGTAGCTGTAGGAAAATATTACTC------------CTATTAC  162
                      *  ** **                                   **

H Factor mRNA   2851 TATGGAGAAGAAGTTACGTACAAATGTTTTCAACGTTTTGGAATTGATGG 2900
CFHR1 mRNA      163 TGTGAATATAATTTTGTGT----CTCCTTCAAAATCATT-------TTGG  201
CFHR3 mRNA      163 TGTGATGAACATTTTGAGA----CTCCGTCAGGAAGTTA-------CTGG  201
                    * **   *    * * **  *      *     *  *         ***

H Factor mRNA   2901 GCCTGCAATTGCAAAATGCTTAGGAGAAAAATGGTCTCACCCTCCATCAT 2950
CFHR1 mRNA      202 ACTCGCA----TAACATGCACAGAAGAAGGATGGTCACCAACACCAAAGT  247
CFHR3 mRNA      202 GATTACA----TTCATTGCACACAAAATGGCTGGTCACCAGCAGTACCAT  247
                      *  **     *    ***     * *   *****  *    *    *

H Factor mRNA   2951 GCATAAAAACAGATTGTCTCAGTTTACCTAGCCTTTGAAAATGCCATACCC 3000
CFHR1 mRNA      248 GTCT-----CAGACTGTGTTTCTTTTCCTTTTGTCGAAAATGGTCATTCTG  292
CFHR3 mRNA      248 GTCT-----CAGAAAATGTTATTTTCCTTATTTCGAAAATGGATATAATC  292
                     * *     **** **  *   ***** *   * * *** *  *  * **

H Factor mRNA   3001 ATGGGAGAGAAGAAGGATCTGTATAAGGCGGG--TGAGCAAGTGACTTAC 3048
CFHR1 mRNA      293 AATCTTCAGGACAAACACATCTGGAAGGTGATACTGTGCAAATTATTTGC  342
CFHR3 mRNA      293 AAAATTATGGAAGAAAGTTTGTACAGGGTAACTCTACAGAAGTTGCCTGC  342
                    *        *    *       *  * * **    *  **  *    * *

H Factor mRNA   3049 A-CTTGTGCAACATATTACAAAATCGATGGAGCCAGTAATGTAACATGCA 3097
CFHR1 mRNA      343 AACACAGGATACAGACTTCAAAACAATCAGAAC----AACATTTCATGTG  388
CFHR3 mRNA      343 CATCCTGGCTACGGTCTTCCAAAACTCCGTCAG-ACCACAGTTACATGTA  391
                         *  **   *  * *  *  *    *       *    *  ****

H Factor mRNA   3098 TTAATAGCAGATGGACAGGAAGGCCAACATGCACA-------GACACCTCC 3141
CFHR1 mRNA      389 TAGAACGGGGCTGGTCCACCCCTCCCAAATCCAGGTCCACTGACACTTCC  438
CFHR3 mRNA      392 CGGAGAATGGCTGGTCTCCTACTCCCACATGCATCC---GAGACAGAACA  438
                      *    * ****         **  * *****      ****  *

H Factor mRNA   3142 TGTGTGAATCCGCCCACAGTACAAAATGCTTATATAGTGTCGAGACAGAT 3191
CFHR1 mRNA      439 TGTGTGAATCCGCCCACAGTACAAAATGCTTATATAGTGTCGAGACAGAT 488
CFHR3 mRNA      439 TGCTCAAAATCAGATATACAAATTCAAAATCGATTCATTTCTGAATCTTC  488
                    **   *  **    *  *  * * ** *  * *    * * **  *

H Factor mRNA   3192 GAGTAAATATCCATCTGGTGACAGAGTACGTTATCAATGTAGGAGCCCTT 3241
CFHR1 mRNA      489 GAGTAAATATCCATCTGGTGACAGAGTACGTTATCAATGTAGGAGCCCTT 538
CFHR3 mRNA      489 CTCTATTTATATTTAAATAAAGAAATACAATATAAATGTAAACCAGCAT   538
                     * ***    *   *        *   ***  ******     *

H Factor mRNA   3242 ATGAAATGTT---TGGGGAT------GAAGAAGTGATGTGTTTAAATGGA 3282
CFHR1 mRNA      539 ATGAAATGTT---TGGGGAT------GAAGAAGTGATGTGTTTAAATGGA 579
CFHR3 mRNA      539 ATGCAACAGCAGATGGAAATTCTTCAGGATCAATTACATGTTTGCGAAAT  588
                    *** **       ***  **        *   *  *  * *****
```

FIG. 7 (cont.)

```
H Factor mRNA    3283 AACTGGACGGAACCACCTCAATGCAAAGATTCTACAGGAAAATGTGGGCC 3332
CFHR1 mRNA       .580 AACTGCACGGAACCACCTCAATGCAAAGATTCTACCGGAAAATGTGGGCC  629
CFHR3 mRNA        589 GGATGGTCAGCACAACCAATTTGCATTAATTCTTCAGAAAAGTGTGGACC  638
                      ***  * * ** ***      ****   *****  * * *** ***** **

H Factor mRNA    3333 CCCTCCACCTATTGACAATGCGGACATTACTTCATTCCCGTTGTCAGTAT 3382
CFHR1 mRNA        630 CCCTCCACCTATTGACAATGCGGACATTACTTCATTCCCGTTGTCAGTAT  679
CFHR3 mRNA        639 TCCTCCACCTATTAGCAATGGTGATACCACCTCCTTTCTACTAAAAGTGT  688
                       ***********  * ****** **  ** ** **  *    *  *** *

H Factor mRNA    3383 ATGCTCCAGCTTCATCAGTTGAGTACCAATGCCAGAACTTGTATCAACTT 3432
CFHR1 mRNA        680 ATGCTCCAGCTTCATCAGTTGAGTACCAATGCCAGAACTTGTATCAACTT  729
CFHR3 mRNA        689 ATGTGCCACAGTCAAGAGTCCAGTACCAATGCCAGTCCTACTATGAACTT  738
                      ***  ***   **   *** ** *************  **  *** *****

H Factor mRNA    3433 CACGGTAACAACCCAATAACATCTAGAAATCGACAATCCTCAGAACCACC 3482
CFHR1 mRNA        730 GAGGGTAACAAGCGAATAACATGTAGAAATGGACAATGGTCAGAACCACC  779
CFHR3 mRNA        739 CAGGGTTCTAATTATGTAACATGTAGTAATGGAGAGTGGTCGGCACCACC  788
                        ****    **   ********** *** *** ***** *    *****

H Factor mRNA    3483 AAAATGCTTACATCCGTGTGTAATATCCCGAGAAATTATGGAAAATTATA 3532
CFHR1 mRNA        780 AAAATGCTTACATCCGTGTGTAATATCCCGAGAAATTATGGAAAATTATA  829
CFHR3 mRNA        789 TAGATGCATACATCCATGTATAATAACTGAAGAAAACATGAATAAAAATA  838
                       * **** ****** *** *****   *  ***** *** * **  ***

H Factor mRNA    3533 ACATAGCATTAAGGTGGACAGCCAAACAGAAGCTTTATTCGAGAACAGGT 3582
CFHR1 mRNA        830 ACATAGCATTAAGGTGGACAGCCAAACAGAAGCTTTATTTGAGAACAGGT  879
CFHR3 mRNA        839 ACATAAAGTTAAAAGGAAGAAGTGACAGAAAATATTATGCAAAAACAGGG  888
                      *****    ****      *      * *  *  ****  * ******

H Factor mRNA    3583 GAATCAGTTGAATTTGTGTGTAAACGGGATATCGTCTTTCATCACGTTC 3632
CFHR1 mRNA        880 GAATCAGCTGAATTTGTGTGTAAACGGGGATATCGTCTTTCATCACGTTC  929
CFHR3 mRNA        889 GATACCATTGAATTTATGTGTAAATTGGGATATAATGCAAATACATCAAT  938
                      **  *  ******* ********       ******    *       **

H Factor mRNA    3633 TCACACATTGCGAACAACATCTTGGGATGGGAAACTGGAGTATCCAACTT 3682
CFHR1 mRNA        930 TCACACATTGCGAACAACATCTTGGGATGGGAAACTGGAGTATCCAACTT  979
CFHR3 mRNA        939 TCTATCATTTCAAGCAGTGTGTCGGGAAGGGATAGTGGAATACCCCAGAT  988
                      **    **** *  **  * *  *****  ****  **** *  **  *

H Factor mRNA    3683 GTGCAAAAAGATAGAATCAAT-CATAAAGTGCACACCTTTATTCAGAACT 3731
CFHR1 mRNA        980 GTGCAAAAAGATAGAATCAAT-CATAAAATGCACACCTTTATTCAGAACT 1028
CFHR3 mRNA        989 GCG-AATAAGGCAGCATTGTTTACCCTAAATGTATGTCCAACTTCCACTTT 1037
                      *  *  ** ***  ** **   *    *  * * *    ***    *

H Factor mRNA    3732 TTAGTATTAAATCAGTTCTCAATTTCATTTTTTATCTATTGTTTTACTCC 3781
CFHR1 mRNA       1029 TTAGTATTAAATCAGTTCTTAATTTAATTTTTTAA-GTATTGTTTTACTCC 1077
CFHR3 mRNA       1038 TCCACTTCTCACTCTTATGGTCTCAAAGCTTGCAAAGATAGCTTCTGATA 1087
                      *   *   *   *      *       *   *    ** **  *

H Factor mRNA    3782 TTTTTATTCATACGTAAAATTTTGGATTAATTTCTGAAAATGTAATTATA 3831
CFHR1 mRNA       1078 TTTTTATTCATACGTAAAATTTTGGATTAATTTGTGAAAATGTAATTATA 1127
CFHR3 mRNA       1088 TTGTTGTA-ATTTCTACTTTATTTCAAAGAAAATTAATATAATAGTTTCA 1136
                      ** ** **  *    ** *   **  *    *   * *  *** *   *
```

FIG. 7 (cont.)

```
H Factor mRNA   3832 AGCTGAGACCGGTGGCTCTCTT                              3853
CFHR1 mRNA     .1128 AGCTGAGACCGGTGGCTCTCTTCTTAAAAGCACCATATTAAAACTTGGAA 1177
CFHR3 mRNA      1137 ATTTCCAAC---TTAATATATTCTCAAAAATATATTAAAACAAACTAAAT 1183
                      *  ** **     *    * * **

H Factor mRNA   3854                                                    3853
CFHR1 mRNA     .1178 AACTGGAAAACT                                       1189
CFHR3 mRNA      1184 TATTGCTTATGCTTGTACTAAAATAATAAAAACTACTCTTATAAAAAAA  1233

H Factor mRNA   3854               3853
CFHL1 mRNA     .1190               1189
CFHL3 mRNA      1234 AAAAAAAAAAAA  1246
```

FIG. 7 (cont.)

METHODS AND REAGENTS FOR TREATMENT AND DIAGNOSIS OF VASCULAR DISORDERS AND AGE-RELATED MACULAR DEGENERATION

CROSS-REFERENCES TO RELATED APPLICATIONS

This application is a Continuation of PCT/US07/73514 filed Jul. 13, 2007, which claims priority to U.S. Provisional Patent Application No. 60/840,073, filed Aug. 23, 2006, and to U.S. Provisional Patent Application No. 60/831,018, filed Jul. 13, 2006. All these applications are hereby incorporated by reference.

STATEMENT AS TO RIGHTS TO INVENTIONS MADE UNDER FEDERALLY SPONSORED RESEARCH AND DEVELOPMENT

This invention was made with government support under NIH R01 EY11515 and R24 EY017404, awarded by the National Institutes of Health. The government has certain rights in the invention.

FIELD OF THE INVENTION

This invention relates to screening and therapeutic methods for complement-mediated diseases such as age-related macular degeneration and vascular diseases. The invention finds application in the fields of biology and medicine.

BACKGROUND OF THE INVENTION

Complement Factor H(CFH) is a multifunctional protein that acts as a key regulator of the complement system. See Zipfel, 2001, "Factor H and disease: a complement regulator affects vital body functions" Semin Thromb Hemost. 27:191-9. The Factor H protein activities include: (1) binding to C-reactive protein (CRP), (2) binding to C3b, (3) binding to heparin, (4) binding to sialic acid; (5) binding to endothelial cell surfaces, (6) binding to cellular integrin receptors (7) binding to pathogens, including microbes (see FIG. 3 of U.S. patent publication No. 20070020647), and (8) C3b co-factor activity. The Factor H gene, known as HF1, CFH and HF, is located on human chromosome 1, at position 1q32. The 1q32 locus contains a number of complement pathway-associated genes. One group of these genes, referred to as the regulators of complement activation (RCA) gene cluster, contains the genes that encode Factor H, five Factor H-related proteins (FHR-1, FHR-2, FHR-3, FHR-4 and FHR-5 or CFHR1, CFHR2, CFHR3, CFHR4 and CFHR5, respectively), and the gene encoding the beta subunit of coagulation factor XIII. The Factor H and Factor H related proteins are composed almost entirely of short consensus repeats (SCRs). Factor H and FHL1 are composed of SCRs 1-20 and 1-7, respectively. FHR-1, FHR-2, FHR-3, FHR-4 and FHR-5 are composed of 5, 4, 5, 5 and 8 SCRs, respectively. The order of genes, from centromere to telomere is FH/FHL1, FHR-3, FHR-1, FHR-4, FHR-2 and FHR-5.

Factor H Gene

The Factor H cDNA encodes a polypeptide 1231 amino acids in length having an apparent molecular weight of 155 kDa (see Ripoche et al., 1988, *Biochem J* 249:593-602). There is an alternatively spliced form of Factor H known as FHL-1 (and also has been referred to as HFL1 or CFHT). FHL-1 corresponds essentially to exons 1 through 9 of Factor H (see Ripoche et al., 1988, *Biochem J* 249:593-602). The FHL1 cDNA encodes a polypeptide 449 amino acids in length having an apparent molecular weight of 45-50 kDa. The first 445 amino acids of FH1 and FHL1 are identical, with FHL1 having four unique C-terminal amino acids (encoded by alternative exon 10A, which is located in the intron between exon 9 and exon 10. cDNA and amino acid sequence data for human Factor H and FHL1 are found in the EMBL/GenBank Data Libraries under accession numbers Y00716 and X07523, respectively. The 3926 base nucleotide sequence of the reference form of human Factor H cDNA has GenBank accession number Y00716 and the polypeptide has GenBank accession number Y00716. The 1658 base nucleotide sequence of the reference form of HFL1, the truncated form of the human Factor H, has GenBank accession number X07523, and the polypeptide sequence has GenBank accession number X07523. The Factor H gene sequence (150626 bases in length) has GenBank accession number AL049744. The Factor H promoter is located 5' to the coding region of the Factor H gene.

FHR-1 Gene

The FHR-1 gene is also known as CFHR1, CFHL1, CFHL, FHR1 and HFL1. The FHR-1 cDNA encodes a polypeptide 330 amino acids in length having an predicted molecular weight of 39 kDa (see Estaller et al., 1991, *J. Immunol.* 146:3190-3196). cDNA and amino acid sequence data for human FHR-1 are found in the EMBL/GenBank Data Libraries under accession number M65292. The FHR-1 gene sequence is found under GenBank accession number AL049741.

FHR-2 Gene

The FHR-2 gene is also known as CFHR2, CFHL2, FHR2 and HFL3. The FHR-2 cDNA encodes a polypeptide 270 amino acids in length having a predicted molecular weight of 31 kDa (see Strausberg et al., *Proc. Natl. Acad. Sci. USA* 99:16899-16903). cDNA and amino acid sequence data for human FHR-2 are found in the EMBL/GenBank Data Libraries under accession number BC022283. The FHR-2 gene sequence is found under GenBank accession number AL139418.

FHR-3 Gene

The FHR-3 gene is also known as CFHR3, CFHL3, FHR3 and HLF4. The FHR-3 cDNA encodes a polypeptide 330 amino acids in length having a predicted molecular weight of 38 kDa (see Strausberg et al., *Proc. Natl. Acad. Sci. USA* 99:16899-16903). cDNA and amino acid sequence data for human FHR-3 are found in the EMBL/GenBank Data Libraries under accession number BC058009. The FHR-3 gene sequence is found under GenBank accession number AL049741.

FHR-4 Gene

The FHR-4 gene is also known as CFHR4, CFHL4 and FHR4. The FHR-4 cDNA encodes a polypeptide 331 amino acids in length having a predicted molecular weight of 38 kDa (see Skerka et al., 1991, *J. Biol. Chem.* 272:5627-5634). cDNA and amino acid sequence data for human FHR-4 are found in the EMBL/GenBank Data Libraries under accession number X98337. The FHR-4 gene sequence is found under GenBank accession numbers AF190816 (5' end), AL139418 (3' end) and BX248415.

FHR-5 Gene

The FHR-5 gene is also known as CFHR5, CFHL5 and FHR5. The CFHR5 cDNA encodes a polypeptide 569 amino acids in length having an apparent molecular weight of 65 kDa (see McRae et al., 2001, *J. Biol. Chem.* 276:6747-6754). cDNA and amino acid sequence data for human CFHR5 are found in the EMBL/GenBank Data Libraries under accession number AF295327. The 2821 base nucleotide sequence of the reference form of human CFHR5 has GenBank accession number AF295327, and the polypeptide sequence has Gen-Bank accession number AAK15619. The CFHR5 genomic sequence is found under GenBank accession numbers AL139418 (5' end) and AL353809 (3' end). The FHR-5 promoter is located 5' to the coding region of the CFHR5 gene.

BRIEF SUMMARY OF THE INVENTION

In one aspect, the invention provides a screening method for determining a human subject's propensity to develop a vascular disorder and/or age-related macular degeneration (AMD), involving analysis of a biological sample from the subject to detect the presence or absence of a deletion in chromosome 1 between the 3' end of exon 22 of the complement factor H(CFH) gene and the 5' end of exon 1 of complement Factor H-related 4 (CFHR4) gene, wherein the presence of a deletion is evidence that the subject is at an increased risk of developing a vascular disorder and a decreased risk of developing AMD.

Examples of vascular disorders include aneurysms, such as abdominal aortic aneurysm (AAA) and brain intracranial aneurysm.

In one embodiment, the method comprises detecting the presence or absence of at least a portion of the complement Factor H-related 3 (CFHR3) gene. In a related embodiment the entire protein coding region of the CFHR3 gene is deleted. In a related embodiment the entire CFHR3 gene is deleted. In a related embodiment the entire CFHR3 gene and the region between the CFHR3 gene and complement Factor H-related 1 (CFHR1) gene are deleted.

In one embodiment, the method comprises detecting the presence or absence of at least a portion of the complement Factor H-related 1 (CFHR1) gene. In a related embodiment the entire protein coding region of the CFHR1 gene is deleted. In a related embodiment the entire CFHR1 gene is deleted. In a related embodiment the entire CFHR1 gene and the region between the CFHR1 gene and complement factor H-related 4 (CFHR4) gene are deleted. In a related embodiment the entire CFHR1 gene and the region between the CFHR1 gene and CFHR3 gene are deleted.

In one embodiment, the method comprises detecting the presence or absence of at least a portion of the CFHR3 gene and at least a portion of the CFHR1 gene. In a related embodiment both the entire protein coding regions of the CFHR3 and CFHR1 genes are deleted. In a related embodiment the entire CFHR3 and CFHR1 genes are deleted.

In one embodiment, a deletion or a partial deletion of an intergenic sequence selected from: a) a sequence between the CFH gene and the CFHR3 gene; b) a sequence between the CFHR3 gene and the CFHR1 gene; c) a sequence between the CFHR1 gene and the CFHR4 gene. In yet another embodiment, at least a portion of the CFH gene is deleted (e.g., at least a portion of exon 22 is deleted).

In one embodiment, the presence or absence of the deletion is detected by assaying for a gene product encoded in chromosome 1 between the 3' end of exon 22 of the complement factor H(CFH) gene and the 5' end of exon 1 of complement Factor H-related 4 (CFHR4) gene, where the absence of the gene product, or a reduced level of expression of the gene product, indicates the presence of deletion. In another embodiment, the presence or absence of a CFHR1 gene product and/or a CFHR3 gene product is detected, where the absence of a gene product is indicative of a deletion. In one instance, the gene product is a protein. In another embodiment, detecting the presence or absence of a deletion is performed by analyzing a chromosome or nucleic acid (e.g., DNA or RNA) from the subject.

In one embodiment the presence or absence of the deletion is detected by assaying for a truncated CFHR1 or CRHR3 gene product, where detection of a truncated gene product is indicative of a deletion. In a preferred embodiment, the CFHR1 gene is partially deleted and expresses a truncated polypeptide gene product.

In one embodiment the subject has a genotype of T at position 1277 of the coding region of the CFH gene of the chromosome comprising the deletion.

The subject may be homozygous or heterozygous for deletions. Thus, in one embodiment, deletions are present in both chromosomes 1 of the subject.

The presence or absence of the deletion may be detected in a biological sample from a patient by, for example, analyzing a chromosome or nucleic acid (e.g., DNA or RNA) sample from the subject. The presence or absence of the deletion also may be detected by, for example, determining the presence or absence of protein encoded by the (deleted) DNA in a biological sample from the subject, e.g., a body fluid or tissue sample of the subject, by detecting a variant or truncated form of the CFHR1 or CFHR3 polypeptides in a body fluid or tissue sample of the subject, or by measuring the level of CFHR1 or CFHR3 polypeptides in a body fluid or tissue sample of the subject.

The biological sample is any sample taken from a patient that is suitable for use in the invention. Examples of biological samples that include body fluids include blood, serum, urine, cerebral spinal fluid (CSF) and saliva. In one embodiment, the body fluid is blood, serum or urine. Examples of biological samples that comprise tissue samples include a skin biopsy and a cheek scraping. In one embodiment, the tissue sample is a skin biopsy.

Proteins (amount or presence) may be detected, for example, using an immunoassay such as a sandwich immunoassay, a competitive immunoassay, a radioimmunoassay, fluorophore-labelled immunoassay, an ELISA or a Western blot. Mass spectroscopy also may be used. Variant proteins (amount or presence) may be detected, for example, using variant-specific antibodies. Truncated proteins (amount or presence) may be detected, for example, by a difference in the size of the protein by Western blot analysis or mass spectroscopy.

In certain embodiments, the method comprises in the detecting step determining the presence of a deletion, for example, a deletion in a CFHR1 or CFHR3 gene, or the absence or a reduction of corresponding gene product (e.g., the amount or activity of the gene product) indicating a higher risk of the subject developing a vascular disorder.

In other embodiments, the method comprises in the detecting step determining the absence of a deletion, for example, the presence of a CFHR1 or CFHR3 gene, or the presence or an increase of the corresponding gene product (e.g., the amount or activity of the gene product) indicating a lower risk of the subject developing a vascular disorder.

In another embodiment, the method comprises in the detecting step determining the presence of a deletion, for example, a deletion in a CFHR1 or CFHR3 gene, or the absence or a reduction of the corresponding gene product (e.g., the amount or activity of the gene product) indicating a lower risk of the subject developing AMD.

In yet another embodiment, the method comprises in the detecting step determining the absence of a deletion, for example, the presence of a CFHR1 or CFHR3 gene, or the presence or an increase of the corresponding gene product (e.g., the amount or activity of the gene product) indicating a higher risk of the subject developing AMD. The increase in gene product, for example, can be at least 10%, at least 20%, at least 50%, or more.

In certain embodiments, the method further comprises detecting at least one other genetic variant or biomarker indicative of AMD and/or vascular disease. Genetic variants that may be detected in the invention include genetic variants of complement factor H(CFH) gene, HTRA1 gene, complement factor B (BF) gene and/or the complement component 2 (C2) gene. In an embodiment, the genetic variants include one or a plurality of polymorphic sites, such as those described herein.

In another aspect, the invention provides a method for treating a subject having (i.e., exhibiting symptoms of), or is at risk for developing, a vascular disorder, by administering a CFHR1 polypeptide and/or a CFHR3 polypeptide to the subject. The polypeptide may be a full-length CFHR1 polypeptide or a fragment or portion thereof. The polypeptide may be a full-length CFHR3 polypeptide or a fragment or portion thereof.

In another aspect the invention provides a pharmaceutical composition comprising a CFHR3 protein or fragment thereof and at least one pharmaceutically effective excipient. In another aspect the invention provides a pharmaceutical composition comprising a CFHR1 protein or fragment thereof and at least one pharmaceutically effective excipient.

In another aspect the invention provides the use of a protein comprising the gene product of at least a portion of the CFHR3 and/or CFHR1 gene for the preparation of a medicament for the treatment of a vascular disorder.

In another aspect the invention provides gene therapy vectors comprising nucleic acid encoding a CFHR3 or CFHR1 protein, or fragment thereof. The vector may include a promoter that drives expression of the CFHR3 or CFHR1 gene in multiple cell types. Alternatively, the vector may include a promoter that drives expression of the CFHR3 or CFHR1 gene only in specific cell types, for example, in cells of the retina or in cells of the kidney. In a related aspect pharmaceutical compositions are provided containing a gene therapy vector encoding a CFHR3 or CFHR1 protein or fragment thereof and a pharmaceutically acceptable excipient.

In another aspect the invention provides a method of treating a subject having (i.e., exhibiting symptoms of), or susceptible to developing, age-related macular degeneration (AMD), by administering an agent that reduces the expression of the CFHR1 and/or CFHR3 genes or reduces the activity or amount of a gene product of the CFHR1 and/or CFHR3 genes. Agents include antisense RNA, siRNA or ribozyme that reduces expression of the CFHR1 and/or CFHR3 genes. In a related aspect the level of protein is reduced, for example by using plasmaphoresis or antibody-based inhibition, for example, using an anti-CFHR1 antibody and/or an anti-CFHR3 antibody.

In another aspect the invention provides a pharmaceutical composition comprising an anti-CFHR1 antibody and a pharmaceutically acceptable carrier. In one embodiment, an anti-CFHR1 antibody specifically binds the amino-terminus of a CFHR1 polypeptide. In another aspect the invention provides a pharmaceutical composition comprising an anti-CFHR3 antibody and a pharmaceutically acceptable carrier. In one embodiment, an anti-CFHR3 antibody specifically binds the carboxyl-terminus of a CFHR3 antibody.

In another aspect the invention provides a diagnostic kit for diagnosing susceptibility to a vascular disorder and/or AMD in a subject, comprising nucleic acid primers or probes that detect the presence or absence of a deletion in the DNA sequence between the 3' end of exon 22 of the complement factor H (CFH) gene and the 5' end of exon 1 of complement Factor H-related 4 (CFHR4) gene on human chromosome 1.

In another aspect the invention provides a diagnostic device comprising nucleic acid primers or probes that detect the presence or absence of a deletion in the DNA sequence between the 3' end of exon 22 of the complement factor H(CFH) gene and the 5' end of exon 1 of complement Factor H-related 4 (CFHR4) gene on human chromosome 1 immobilized on a substrate, such as a microarray.

In another aspect the invention provides a diagnostic kit for diagnosing susceptibility to a vascular disorder and/or AMD in a subject, comprising antibodies that detect the presence or absence of the complement Factor H-related 3 (CFHR3) protein, or variant or truncated forms thereof, and/or complement Factor H related 1 (CFHR1) protein, or variant or truncated forms thereof, in a body fluid or tissue sample of the subject.

In another aspect the invention provides a drug screening method for screening for agents for use in treating a vascular disorder. The method involves a) combining (i) a cell that expresses CFHR3 and/or CFHR1 polypeptides; and (ii) a test agent; b) measuring the level of CFHR3 and/or CFHR1 polypeptides secreted into the medium; and c) comparing the level of CFHR3 and/or CFHR1 polypeptides secreted into the medium in the presence of the test agent with a reference value, said reference value being the level of CFHR3 and/or CFHR1 polypeptides secreted into the medium in the absence of the test agent, where a higher level of CFHR3 and/or CFHR1 polypeptides secreted into the medium in the presence of the test agent indicates the test agent may be useful for treating the vascular disorder.

In another aspect the invention provides a method for identifying a CFH protein likely to protect against AMD development, by identifying a subject with a deletion in the DNA sequence between the 3' end of exon 22 of the complement factor H(CFH) gene and the 5' end of exon 1 of complement Factor H-related 4 (CFHR4) gene on human chromosome 1; determining the sequence of the CFH gene encoded by the gene contained in the chromosome containing the deletion; and determining the sequence of the protein encoded by the CFH gene, wherein said protein is different from wild-type CFH, said protein being a CFH protein likely to protect against AMD development. The invention also provides a protective CFH protein obtained using the method.

BRIEF DESCRIPTION OF THE FIGURES

FIG. 6 shows an amino acid alignment of the CFH (SEQ ID NO: 2), CFHR1 (SEQ ID NO: 4), and CFHR3 (SEQ ID NO: 6) proteins.

FIG. 7 shows a nucleotide alignment of the CFH (SEQ ID NO: 1), CFHR1 (SEQ ID NO: 3), and CFHR3 genes (SEQ ID NO: 5).

DETAILED DESCRIPTION

1. Definitions

Figure 1:
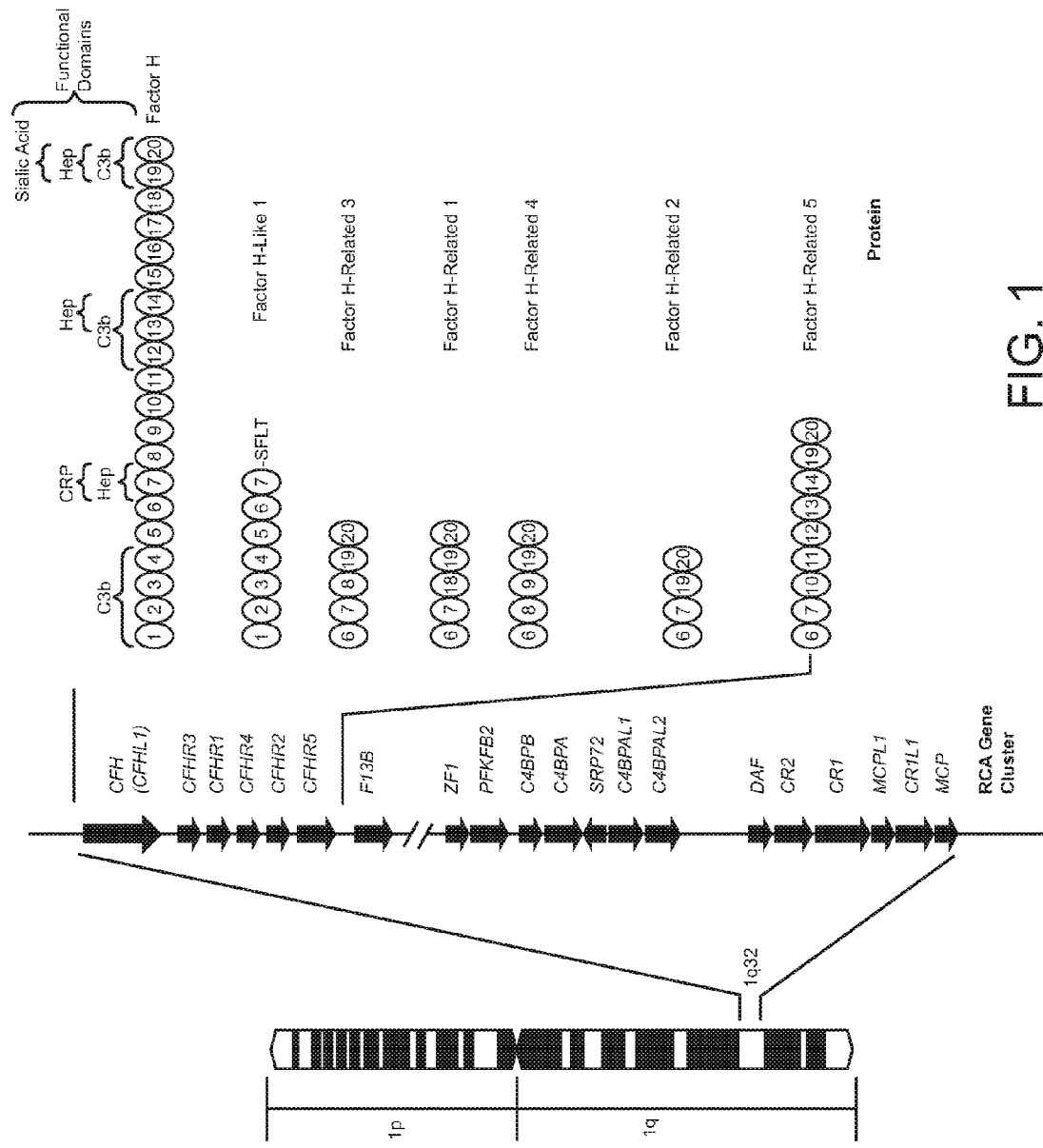
FIG. 1 is a diagram showing the organization of the regulators-of-complement-activation (RCA) gene cluster on chromosome 1q32 and the arrangement of approximately 60-amino acid domains known as short consensus repeats (SCRs) in complement Factor 1-1 (CFH), Factor H-Like 1 (CFHL1) and Factor H-Related 1, 2, 3, 4 and 5 (CFHR1, CFHR2, CFHR3, CFHR4 and CFHR5). CFH has 20 SCRs. The interacting partners with some of these SCRs has been determined and is shown on the top right (CRP, C reactive protein; Hep, heparin). Complement factor H-like 1 (CFHL1) is a splice isoform of CFH, while complement factor H-related proteins 1-5 (CFHR1-5) are each encoded by a unique gene (CFHR1-5). The SCRs of CFHR1-5 are similar to some of the SCRs in CFH, as denoted by the numbers in the ovals. For example, CFHR5 has 9 SCRs, with the first two being similar to SCRs 6 and 7 of Factor H and therefore having CRP and heparin binding properties. SCRs 5-7 of CFHR5 have the numbers 12-14 within the corresponding ovals because these SCRs are similar to SCRs 12-14 of Factor H and have C3b and heparin binding properties.
Figure 2:
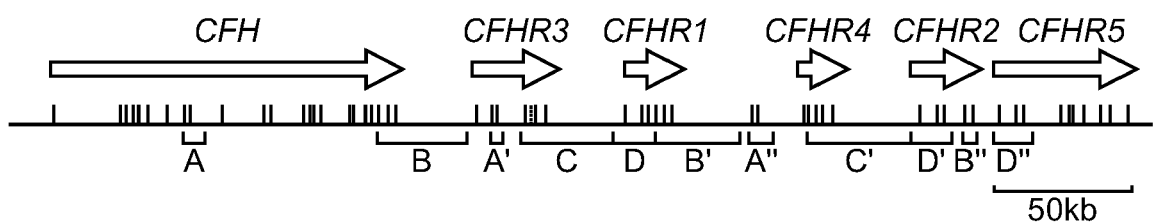
FIG. 2 shows regions of homology (genomic duplications) in the genes encoding CFH and the Factor H-related proteins. Exons are indicated as vertical lines. Regions labeled with the same letter (e.g., A, A', and A") have substantially identical sequences.

The following definitions are provided to aid in understanding the invention. Unless otherwise defined, all terms of art, notations and other scientific or medical terms or terminology used herein are intended to have the meanings commonly understood by those of skill in the arts of medicine and molecular biology. In some cases, terms with commonly understood meanings are defined herein for clarity and/or for ready reference, and the inclusion of such definitions herein should not be assumed to represent a substantial difference over what is generally understood in the art.

A "vascular disorder" is a disease or condition of the vascular system. One type of vascular disorder is an aneurysm such as abdominal aortic aneurysm or brain intracranial aneurysm. Other types of vascular disorder include hypertension, cerebral vascular accidents, trans-ischemic accidents (e.g., stroke). Still other types of vascular disorders include coronary artery disease, peripheral artery disease, varicose veins, and peripheral vascular disease.

A "nucleic acid", "polynucleotide" or "oligonucleotide" is a polymeric form of nucleotides of any length, may be DNA or RNA, and may be single- or double-stranded. Nucleic acids may include promoters or other regulatory sequences. Oligonucleotides are usually prepared by synthetic means. A reference to the sequence of one strand of a double-stranded nucleic acid defines the complementary sequence and except where otherwise clear from context, a reference to one strand of a nucleic acid also refers to its complement. For certain applications, nucleic acid (e.g., RNA) molecules may be modified to increase intracellular stability and half-life. Possible modifications include, but are not limited to, the use of phosphorothioate or 2'-O-methyl rather than phosphodiesterase linkages within the backbone of the molecule. Modified nucleic acids include peptide nucleic acids (PNAs) and nucleic acids with nontraditional bases such as inosine, queosine and wybutosine and acetyl-, methyl-, thio-, and similarly modified forms of adenine, cytidine, guanine, thymine, and uridine which are not as easily recognized by endogenous endonucleases.

"Hybridization probes" are nucleic acids capable of binding in a base-specific manner to a complementary strand of nucleic acid. Such probes include nucleic acids and peptide nucleic acids (Nielsen et al., 1991). Hybridization may be performed under stringent conditions which are known in the art. For example, see, e.g., Berger and Kimmel (1987) METHODS IN ENZYMOLOGY, VOL. 152: GUIDE TO MOLECULAR CLONING TECHNIQUES, San Diego: Academic Press, Inc.; Sambrook et al. (1989) MOLECULAR CLONING: A LABORATORY MANUAL, 2nd Ed., Vols. 1-3, Cold Spring Harbor Laboratory; Sambook (2001) 3rd Edition; Rychlik, W. and Rhoads, R. E., 1989, Nucl. Acids Res. 17, 8543; Mueller, P. R. et al. (1993) In: CURRENT PROTOCOLS IN MOLECULAR BIOLOGY 15.5, Greene Publishing Associates, Inc. and John Wiley and Sons, New York; and Anderson and Young, QUANTITATIVE FILTER HYBRIDIZATION IN NUCLEIC ACID HYBRIDIZATION (1985)). As used herein, the term "probe" includes primers. Probes and primers are sometimes referred to as "oligonucleotides."

The term "primer" refers to a single-stranded oligonucleotide capable of acting as a point of initiation of template-directed DNA synthesis under appropriate conditions, in an appropriate buffer and at a suitable temperature. The appropriate length of a primer depends on the intended use of the primer but typically ranges from 15 to 30 nucleotides. A primer sequence need not be exactly complementary to a template but must be sufficiently complementary to hybridize with a template. The term "primer site" refers to the area of the target DNA to which a primer hybridizes. The term "primer pair" means a set of primers including a 5' upstream primer, which hybridizes to the 5' end of the DNA sequence to be amplified and a 3' downstream primer, which hybridizes to the complement of the 3' end of the sequence to be amplified.

Exemplary hybridization conditions for short probes and primers is about 5 to 12 degrees C. below the calculated Tm. Formulas for calculating Tm are known and include: Tm=4° C.×(number of G's and C's in the primer)+2° C.×(number of A's and T's in the primer) for oligos <14 bases and assumes a reaction is carried out in the presence of 50 mM monovalent cations. For longer oligos, the following formula can be used: Tm=64.9° C.+41° C.×(number of G's and C's in the primer–16.4)/N, where N is the length of the primer. Another commonly used formula takes into account the salt concentration of the reaction (Rychlik, supra, Sambrook, supra, Mueller, supra.): Tm=81.5° C.+16.6° C.×(log 10[Na+]+[K+])+0.41° C.×(% GC)−675/N, where N is the number of nucleotides in the oligo. The aforementioned formulae provide a starting point for certain applications; however, the design of particular probes and primers may take into account additional or different factors. Methods for design of probes and primers for use in the methods of the invention are well known in the art.

The term "polymorphism" refers to the occurrence of two or more genetically determined alternative sequences or alleles in a population. A "polymorphic site" is the locus at which sequence divergence occurs. Polymorphic sites have at least two alleles. A diallelic polymorphism has two alleles. A triallelic polymorphism has three alleles. Diploid organisms may be homozygous or heterozygous for allelic forms. A polymorphic site may be as small as one base pair. Examples of polymorphic sites include: restriction fragment length polymorphisms (RFLPs); variable number of tandem repeats (VNTRs); hypervariable regions; minisatellites; dinucleotide repeats; trinucleotide repeats; tetranucleotide repeats; and simple sequence repeats. As used herein, reference to a "polymorphism" can encompass a set of polymorphisms (i.e., a haplotype).

A "single nucleotide polymorphism (SNP)" occurs at a polymorphic site occupied by a single nucleotide, which is the site of variation between allelic sequences. The site is usually preceded by and followed by highly conserved sequences of the allele. A SNP usually arises due to substitution of one nucleotide for another at the polymorphic site. Replacement of one purine by another purine or one pyrimidine by another pyrimidine is called a transition. Replacement of a purine by a pyrimidine or vice versa is called a transversion. A synonymous SNP refers to a substitution of one nucleotide for another in the coding region that does not change the amino acid sequence of the encoded polypeptide. A non-synonymous SNP refers to a substitution of one nucleotide for another in the coding region that changes the amino acid sequence of the encoded polypeptide. A SNP may also arise from a deletion or an insertion of a nucleotide or nucleotides relative to a reference allele.

The term "deletion," when referring to a nucleic acid sequence, has the usual meaning in genetics of an allele in which one or more bases are missing compared to a reference or wild-type sequence. Deletions may be as short as one base-pair. Deletions detected in the present invention may be longer, such as a deletion of at least 100 bp, at least 200 bp, at least 300 bp, at least 400 bp, at least 500 bp, at least 600 bp, at least 700 bp, at least 800 bp, at least 900 bp, at least 1000 bp, at least 1100 bp, at least 1200 bp, at least 1300 bp, at least 1400 bp, at least 1500 bp, at least 1600 bp, at least 1700 bp, at least 1800 bp, at least 1900 bp, at least 2000 bp, at least 2500 bp, at least 3000 bp, at least 3500 bp, at least 4000 bp, at least 4500 bp, at least 5000 bp, at least 6000 bp, at least 7000 bp, at least 8000 bp, at least 9000 bp, at least 10,000 bp, at least 15,000 bp, at least 20,000 bp, at least 30,000 bp, at least 40,000 bp, at least 50,000 bp, at least 75,000 bp, at least 100,000 bp, at least 125,000 bp, at least 150,000 bp, at least 200,000 bp or at least 250,000 bp.

The term "haplotype" refers to the designation of a set of polymorphisms or alleles of polymorphic sites within a gene of an individual. For example, a "112" Factor H haplotype refers to the Factor H gene comprising allele 1 at each of the first two polymorphic sites and allele 2 at the third polymorphic site. A "diplotype" is a haplotype pair.

An "isolated" nucleic acid means a nucleic acid species that is the predominant species present in a composition. Isolated means the nucleic acid is separated from at least one compound with which it is associated in nature. A purified nucleic acid comprises (on a molar basis) at least about 50, 80 or 90 percent of all macromolecular species present.

Two amino acid sequences are considered to have "substantial identity" when they are at least about 80% identical, preferably at least about 90% identical, more preferably at least about 95%, at least about 98% identical or at least about 99% identical. Percentage sequence identity is typically calculated by determining the optimal alignment between two sequences and comparing the two sequences. Optimal alignment of sequences may be conducted by inspection, or using the local homology algorithm of Smith and Waterman, 1981, *Adv. Appl. Math.* 2: 482, using the homology alignment algorithm of Needleman and Wunsch, 1970, *J. Mol. Biol.* 48: 443, using the search for similarity method of Pearson and Lipman, 1988, *Proc. Natl. Acad. Sci. U.S.A.* 85: 2444, by computerized implementations of these algorithms (e.g., in the Wisconsin Genetics Software Package, Genetics Computer Group, 575 Science Dr., Madison, Wis.) using default parameters for amino acid comparisons (e.g., for gap-scoring, etc.). It is sometimes desirable to describe sequence identity between two sequences in reference to a particular length or region (e.g., two sequences may be described as having at least 95% identity over a length of at least 500 basepairs). Usually the length will be at least about 50, 100, 200, 300, 400, 500, 600, 700, 800, 900 or 1000 amino acids, or the full length of the reference protein. Two amino acid sequences can also be considered to have substantial identity if they differ by 1, 2, or 3 residues, or by from 2-20 residues, 2-10 residues, 3-20 residues, or 3-10 residues.

"Linkage" describes the tendency of genes, alleles, loci or genetic markers to be inherited together as a result of their location on the same chromosome. Linkage can be measured by percent recombination between the two genes, alleles, loci or genetic markers. Typically, loci occurring within a 50 centimorgan (cM) distance of each other are linked. Linked markers may occur within the same gene or gene cluster. "Linkage disequilibrium" or "allelic association" means the preferential association of a particular allele or genetic marker with a specific allele or genetic marker at a nearby chromosomal location more frequently than expected by chance for any particular allele frequency in the population. A marker in linkage disequilibrium can be particularly useful in detecting susceptibility to disease, even if the marker itself does not cause the disease.

The terms "susceptibility," "propensity," and "risk" refer to either an increased or decreased likelihood of an individual developing a disorder (e.g., a condition, illness, disorder or disease) relative to a control population. In one example, the control population may be individuals in the population (e.g., matched by age, gender, race and/or ethnicity) without the disorder, or without the genotype or phenotype assayed for. In some contexts, the terms diagnosing and screening are used interchangeably (e.g., a person skilled in the art can diagnose a propensity to develop the disease).

The term "diagnose" and "diagnosis" refer to the ability to determine or identify whether an individual has a particular disorder (e.g., a condition, illness, disorder or disease).

The term "screen" or "screening" as used herein has a broad meaning. It includes processes intended for the diagnosis or for determining the susceptibility, propensity, risk, or risk assessment of an asymptomatic subject for developing a disorder later in life. Screening also includes the prognosis of a subject, i.e., when a subject has been diagnosed with a disorder, determining in advance the progress of the disorder as well as the assessment of efficacy of therapy options to treat a disorder.

The terms "portion," "fragment" and/or "truncated form" when used in reference to a Factor H-related gene product (e.g., CFHR3 or CFHR1 gene product), refers to a nucleic acid or polypeptide sequence that is less than the full-length sequence (i.e., a portion of the full-length gene or polypeptide). A portion or fragment or truncated form of CFHR3 or CFHR1 gene or polypeptide can be at least 25, at least 50, at least 75, at least 100, at least 150, at least 200, at least 250, or at least 300 nucleotides or amino acids in length. Typically the portion includes at least 1, often at least two, and sometimes at least 3 or 4 complete SCRs.

As used herein, the term "gene product" means an RNA (e.g., mRNA) or protein that is encoded by the gene. A "protein coding region" is a region of DNA/RNA sequence within a gene that encodes a polypeptide or protein.

An "assay" is a procedure wherein the presence or amount or a property of a test substance, e.g., a nucleic acid or gene product, is detected or measured.

The terms "inhibit" and "reduce" refer to any inhibition, reduction, or decrease in expression or activity including partial or complete inhibition of gene expression or gene product activity.

2. Association of Polymorphisms in the CFHR1 and CFHR3 Genes and Risk of Developing AMD and Vascular Disorders A correlation between polymorphic sites and haplotypes in the CFH gene and the likelihood of developing AMD has been discovered. See Hageman et al., 2005, *Proc. Natl. Acad. Sci. U.S.A.* 102:7227-32; Haines et al., 2005, *Science* 308:419-21; Klein et al., 2005, *Science* 308:385-9; Edwards et al., 2005, *Science* 308:421-4 and U.S. patent publication No. 20070020647, each incorporated by reference in its entirety for all purposes. Both CFH risk haplotypes and CFH protective haplotypes are known. Polymorphisms particularly associated with increased risk include a variant allele at: rs1061170 (420H; exon 9); rs203674 (intron 10) and the polymorphism at residue 1210 (1210C; exon 22).

Polymorphisms particularly associated with decreased risk include the protective H2 haplotype, which includes a variant allele in IVS6 (intron 6, rs3766404) and the H4 haplotype, which includes a variant allele in IVS1 (intron 1, rs529825) and a variant allele (162) (exon 2, rs800292).

It has now been discovered that an AMD protective haplotype is genetically linked to deletions in the DNA sequence between the 3' end of exon 22 of the complement factor H(CFH) gene and the 5' end of exon 1 of complement Factor H-related 4 (CFHR4) gene on human chromosome 1 (i.e., the DNA sequence encoding the CFHR1 and CFHR3 proteins). See Example 1, infra. The discovery that deletions at the CFHR1 and CFHR3 loci are associated with decreased risk of developing AMD has a number of specific applications, including screening individuals to ascertain risk of developing AMD and identification of new and optimal therapeutic approaches for individuals afflicted with, or at increased risk of developing, AMD. As discussed in Example 1, below, the deletion genotype is predominantly associated with the CFH H4 haplotype. See Hageman et al., 2005, *Proc. Natl. Acad. Sci. U.S.A.* 102:7227-32. Thus, this deletion acts as a marker for decreased risk of conditions for which the H4 haplotype is protective.

Moreover, it has now been discovered that deletions in the DNA sequence between the 3' end of exon 22 of the complement factor H(CFH) gene and the 5' end of exon 1 of complement Factor H-related 4 (CFHR4) gene on human chromosome 1 (i.e., the DNA sequence encoding the CFHR1 and CFHR3 proteins) are associated with increased risk of developing a vascular disease such as aortic aneurysm. See Example 1, infra. The discovery that deletions at the CFHR1 and CFHR3 loci are associated with increased risk of developing a vascular disorder has a number of specific applications, including screening individuals to ascertain risk of developing a vascular disorder and identification of new and optimal therapeutic approaches for individuals afflicted with, or at increased risk of developing, vascular disorders.

3. Screening Methods

Based on the discoveries described herein, a subject's risk for AMD or vascular disease can be assessed by determining whether or not a the subject has a deletion within the region of chromosome 1 lying between the 3' end of exon 22 of the complement factor H(CFH) gene and the 5' end of exon 1 of complement Factor H-related 4 (CFHR4). The extent of the deletion may vary in different individuals or populations. For example, in one embodiment the all of most of the region between CFH exon 22 and CFHR4 exon 1 is deleted. Alternatively, a portion of the region may be deleted, such as, for example, a deletion of less than the entire region between CFH exon 22 and CFHR4 exon 1 but including the CFHR1 encoding sequence, or including the CFHR3 encoding sequence, including both, or including a non-coding (e.g., intragenic) sequence. An individual may be homozygous for deletion (both chromosomes 1 have a deletion in the region) or may be heterozygous for deletion.

For example and not limitation, the homozygous deletion of CFHR1 and/or CFHR3 can be detected from the absence of CFHR1 and/or CFHL3 protein in a body fluid or tissue sample (see FIG. 3), by the absence of RNA encoded in the region between the 3' end of CFH exon 22 and the 5' end of CFHR4 exon 1 (e.g., absense of absence of CFHR1 and/or CFHL3 mRNAs), or by absense of genomic DNA in the region in the region between the 3' end of CFH exon 22 and the 5' end of CFHR4 exon 1. The present or absense of DNA or RNA sequences can be determined using art known methods, such as PCR. The absense of a nucleic acid sequence is deduced from the absense of an amplified PCR product in an assay of a tissue sample (see FIG. 5). It will be understood that, although PCR is frequently cited herein as a method for genetic analysis, many other analytical methods are known and are suitable for detection of a deletion. For example and not limitation several are described below in the section captioned "Analysis of Nucleic Acid Samples."

The heterozygous deletion of CFHR1 and/or CFHR3 can be determined, for illustration and not limitation, (1) from a reduction in the amount of protein in a body fluid or tissue sample as compared to the amount from a control having both alleles of CFHR1 and/or CFHR3 genes, (2) from a reduction in the amount of RNA, DNA, or amplified PCR product in a tissue sample as compared to the amount from similar sample of a homozygote without the deletion, or (3) by an assay using direct DNA sequencing, quantitative PCR or other methods known in the art. For example, the amount of a gene product may be reduced in a heterozygote by at least 10%, at least 20%, at least 30%, about 50% or more compared to a homozygote without the deletion. Quantitative PCR and methods are available that would be able to detect a two-fold difference in mRNA or DNA in a sample.

As noted, a deletion lies in the region between CFH exon 22 and CFHR4 exon 1 but need not span the entire region. Deletions of a portion of the CFHR1 and/or CFHR3 genes ("partial deletions") may result in truncated forms of CFHR1 and/or CFHR3 RNAs and polypeptides. Such partial deletions can be identified by a difference in size of a protein in a body fluid or tissue sample compared to the full-length protein, by detecting a size difference in the RNA, and by various methods well known in the art, including PCR amplification of DNA or RNA in a biological sample using primers selected to distinguish between a nucleic acid comprising a deletion and a nucleic acid not containing a deletion. Methods known in the art can be used to distinguish homozygotes from heterozygotes (see, e.g., Example 1).

The selection, design and manufacture of suitable primers or probes for analysis of nucleic acid is well known in the art. A person of ordinary skill in the art can use suitable combinations of primers to detect deletions. In an embodiment, the primers or probes are designed to hybridize at any position in the DNA sequence between the 3' end of exon 22 of the complement factor H (CFH) gene and the 5' end of exon 1 of complement Factor H-related 4 (CFHR4) gene. For instance, both primers may be located in the CHFR3 gene to detect its presence or absence. In another example. In other examples, one or more primers are located within intergenic (non-coding) sequence, e.g., intergenic sequence between between CFHR3 and CFHR1 or between CFHR1 and CFHR4.

In another embodiment, the invention includes a method of detecting a nonreciprocal transfer of genetic information, such as gene conversion. In one instance, the gene conversion results in replacement of a 3' portion of the CFH gene with a portion of the 3'CFHR1 gene, such that a chimeric protein with sequence derived from both the CFH gene and the CFHR1 gene is produced.

3.1 Analysis of Nucleic Acid Samples

Methods for detection of polymorphisms and deletions in genetic sequences are well known in the art and can be adapted for use in the present invention.

In one embodiment, genomic DNA is analyzed. For assay of genomic DNA, virtually any biological sample containing genomic DNA or RNA, e.g., nucleated cells, is suitable. For example, genomic DNA can be obtained from peripheral blood leukocytes collected from case and control subjects (QIAamp DNA Blood Maxi kit, Qiagen, Valencia, Calif.). Other suitable samples include saliva, cheek scrapings, biopsies of retina, kidney, skin, or liver or other organs or tissues; amniotic fluid, cerebral spinal fluid (CSF) samples; and the like. Alternatively RNA or cDNA can be assayed. Methods for purification or partial purification of nucleic acids from patient samples for use in diagnostic or other assays are well known Methods for detecting polymorphisms and deletions in nucleic acids include, without limitation, Southern blot analysis (see Kees et al., "Homozygous Deletion of the p16/MTS1 Gene in Pediatric Acute Lymphoblastic Leukemia Is Associated With Unfavorable Clinical Outcome," *Blood* 89:4161-4166, Fizzotti et al., "Detection of homozygous deletions of the cyclin-dependent kinase 4 inhibitor (p16) gene in acute lymphoblastic leukemia and association with adverse prognostic features," *Blood* 85(10):2685-2690, Kitada et al., "Mutations in the parkin gene cause autosomal recessive juvenile parkinsonism," *Nature* 392 (9):605-608); Northern Blot Analysis (see Fieschi et al., "A novel form of complete IL-12/IL-23 receptor b1 deficiency with cell surface-expressed nonfunctional receptors," *Immunobiology* 104(7):2095-2101) and amplification based method such as PCR-based methods are used to detect deletions in samples. PCR primers may be designed to target DNA sequences flanking a known mutation, in which a change in PCR product size in comparison to amplification reactions using WT DNA identifies a mutant template. Primers may also be targeted to deleted sequences, wherein an absence of a PCR product identifies a mutant template (Kitada et al., "Mutations in the parkin gene cause autosomal recessive juvenile parkinsonism," *Nature* 392:605-608) including multiplex PCR (Chong et al., "Single-tube multiplex-PCR screen for common deletional determinants of α-thalassemia," *Blood* 95 (1):360-362).

Polymorphisms (e.g., deletions) can also be detected using allele-specific probes; use of allele-specific primers; direct sequence analysis; denaturing gradient gel electropohoresis (DGGE) analysis; single-strand conformation polymorphism (SSCP) analysis; and denaturing high performance liquid chromatography (DHPLC) analysis. Other well known methods to detect polymorphisms in DNA include use of: Molecular Beacons technology (see, e.g., Piatek et al., 1998; *Nat. Biotechnol.* 16:359-63; Tyagi, and Kramer, 1996, *Nat. Biotechnology* 14:303-308; and Tyagi, et al., 1998, *Nat. Biotechnol.* 16:49-53), Invader technology (see, e.g., Neri et al., 2000, *Advances in Nucleic Acid and Protein Analysis* 3826: 117-125 and U.S. Pat. No. 6,706,471), nucleic acid sequence based amplification (Nasba) (Compton, 1991), Scorpion technology (Thelwell et al., 2000, *Nuc. Acids Res,* 28:3752-3761 and Solinas et al., 2001, "Duplex Scorpion primers in SNP analysis and FRET applications" *Nuc. Acids Res,* 29:20), restriction fragment length polymorphism (RFLP) analysis, and the like.

The design and use of allele-specific probes for analyzing polymorphisms are described by e.g., Saiki et al., 1986; Dattagupta, EP 235,726; and Saiki, WO 89/11548. Briefly, allele-specific probes are designed to hybridize to a segment of target DNA from one individual but not to the corresponding segment from another individual, if the two segments represent different polymorphic forms. Hybridization conditions are chosen that are sufficiently stringent so that a given probe essentially hybridizes to only one of two alleles. Typically, allele-specific probes are designed to hybridize to a segment of target DNA such that the polymorphic site aligns with a central position of the probe.

Exemplary probes for analyzing deletions and polymorphisms are shown in Table 1 of Example 1, but many others may be designed by one of skill.

Allele-specific probes are often used in pairs, one member of a pair designed to hybridize to the reference allele of a target sequence and the other member designed to hybridize to the variant allele. Several pairs of probes can be immobilized on the same support for simultaneous analysis of multiple polymorphisms within the same target gene sequence.

The design and use of allele-specific primers for analyzing polymorphisms are described by, e.g., WO 93/22456 and Gibbs, 1989. Briefly, allele-specific primers are designed to hybridize to a site on target DNA overlapping a polymorphism and to prime DNA amplification according to standard PCR protocols only when the primer exhibits perfect complementarity to the particular allelic form. A single-base mismatch prevents DNA amplification and no detectable PCR product is formed. The method works best when the polymorphic site is at the extreme 3'-end of the primer, because this position is most destabilizing to elongation from the primer.

Amplification products generated using PCR can be analyzed by the use of denaturing gradient gel electrophoresis (DGGE). Different alleles can be identified based on sequence-dependent melting properties and electrophoretic migration in solution. See Erlich, ed., PCR Technology, Principles and Applications for DNA Amplification, Chapter 7 (W.H. Freeman and Co, New York, 1992).

Alleles of target sequences can be differentiated using single-strand conformation polymorphism (SSCP) analysis. Different alleles can be identified based on sequence- and structure-dependent electrophoretic migration of single stranded PCR products (Orita et al., 1989). Amplified PCR products can be generated according to standard protocols, and heated or otherwise denatured to form single stranded products, which may refold or form secondary structures that are partially dependent on base sequence.

Alleles of target sequences can be differentiated using denaturing high performance liquid chromatography (DHPLC) analysis. Different alleles can be identified based on base differences by alteration in chromatographic migration of single stranded PCR products (Frueh and Noyer-Weidner, 2003, *Clin Chem Lab Med.* 41(4):452-61). Amplified PCR products can be generated according to standard protocols, and heated or otherwise denatured to form single stranded products, which may refold or form secondary structures that are partially dependent on the base sequence.

Direct sequence analysis of polymorphisms can be accomplished using DNA sequencing procedures that are well-known in the art. See Sambrook et al., MOLECULAR CLONING, A LABORATORY MANUAL (2nd Ed., CSHP, New York 1989) and Zyskind et al., RECOMBINANT DNA LABORATORY MANUAL (Acad. Press, 1988).

Homozygote deletions can be identified by a variety of methods known in the art. For example, in one approach DNA samples are amplified for further analysis. In an embodiment, two CFHR1-specific primer pairs are used, for instance, ("CFHL1ex6.F" [5'-AGTCGGTTTGGACAGTG-3' (SEQ ID NO: 7)] & "CFHL1ex6R" [5'-GCACAAGTTG-GATACTCC-3' (SEQ ID NO: 8)]; and/or "CHFL1ex6.F2" [5'-CATAGTCGGTTTGGACAGTG-3' (SEQ ID NO: 9)] & "CFHL1ex6.R" [5'-GCACAAGTTGGATACTCC-3' (SEQ ID NO: 8)]). In another embodiment, CFHR3-specific primer pairs are used. for instance, ("CFHL3ex3.F" [5'-TCATTGC-TATGTCCTTAGG-4' (SEQ ID NO: 10)] & "CFHL3ex3.R" [5'-TCTGAGACTGTCGTCCG-3' (SEQ ID NO: 11)]; and/or "CFHL3ex3seq.F" [5'-TTTTGGATGTTTATGCG-3' (SEQ ID NO: 12)] & "CFHL3ex3seq.R" [5'-AAATAGGTCCGT-TGGC-3' (SEQ ID NO: 13)]). Absence of the correct-sized PCR product indicates that the CFHL1 and/or CFHL3 gene(s) are deleted.

Similarly, heterozygote deletions can be identified by a variety of methods known in the art. For example, in one approach DNA samples are amplified for further analysis, for example with the same primers listed above, followed by direct sequencing. Heterozygotes are characterized, for instance, by chromatograms in which one peak is approximately half the height of the second peak (in contrast to equal sized peaks) at the SNP positions (rs460897, rs16840561, rs4230, rs414628 for CFHR1; rs1061170 for CFHR3). In another embodiment, a protocol employing ParAllele genotyping data, a copy number analysis is performed, in which samples that fail to genotype key markers (MRD_3855, MRD_3856, MRD_3857, rs385390, rs389897) in the region of these two genes are identified. All samples assigned a copy number of 0 (designated CN0) allow the haplotypes that contain the deletion to be defined. Having defined a deletion haplotype, linkage disequilibrium is used to infer whether samples could not carry a deletion. Specifically, if a sample is homozygous for a different allele than one that defines the haplotype, then it does not carry a deletion.

A wide variety of other methods are known in the art for detecting polymorphisms in a biological sample. For example and not limitation, see, e.g., Ullman et al. "Methods for single nucleotide polymorphism detection" U.S. Pat. No. 6,632,606; Shi, 2002, "Technologies for individual genotyping: detection of genetic polymorphisms in drug targets and disease genes" *Am J Pharmacogenomics* 2:197-205; and Kwok et al., 2003, "Detection of single nucleotide polymorphisms" *Curr Issues Biol.* 5:43-60).

3.2 Analysis of Protein Samples

Methods for protein analysis that can be adapted for detection of proteins such as the CFHR1 and CFHR3 gene products and variants or fragments thereof are well known. These methods include analytical biochemical methods such as electrophoresis (including capillary electrophoresis and one- and two-dimensional electrophoresis), chromatographic methods such as high performance liquid chromatography (HPLC), thin layer chromatography (TLC), hyperdiffusion chromatography, mass spectrometry, and various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting and others.

For example, a number of well established immunological binding assay formats suitable for the practice of the invention are known (see, e.g., Harlow, E.; Lane, D. ANTIBODIES: A LABORATORY MANUAL. Cold Spring Harbor, N.Y.: Cold Spring Harbor Laboratory; 1988; and Ausubel et al., (2004) CURRENT PROTOCOLS IN MOLECULAR BIOLOGY, John Wiley & Sons, New York N.Y. The assay may be, for example, competitive or non-competitive. Typically, immunological binding assays (or immunoassays) utilize a "capture agent" to specifically bind to and, often, immobilize the analyte. In one embodiment, the capture agent is a moiety that specifically binds to a variant or wild-type CFHR1 or CFHR3 polypeptide or subsequence (e.g., a fragment or truncated form of CFHR1 or CFHR3). The bound protein may be detected using, for example, a detectably labeled anti-CFHR1 or anti-CFHR3 antibody.

3.3 Screening Using Multiple Polymorphisms and Markers

In diagnostic methods, analysis of CFHR1 and/or CFHR3 polymorphisms can be combined with analysis of polymorphisms in other genes associated with AMD or vascular disease (e.g., AAA), detection of protein markers of AMD (see, e.g., Hageman et al., patent publications US 20030017501; US 20020102581; WO0184149; and WO0106262; and U.S. patent application Ser. Nos. 11/706,154 (entitled "Protective Complement Proteins and Age-Related Macular Degeneration") and 11/706,074 (entitled "Variants in Complement Regulatory Genes Predict Age-Related Macular Degeneration"); Gorin et al., US20060281120; and Hoh, WO2007/044897, each of which are incorporated herein by reference in their entirety for all purposes), assessment of other risk factors of AMD or vascular disease (such as family history).

For example, analysis of CFHR1 and/or CFHR3 polymorphisms (e.g., deletions) can be combined with the analysis of polymorphisms in the Complement Factor H gene (CFH). Genetic variants of the CFH gene that may be detected include, but are not limited to, a genotype of a T at position 1277 of the coding region of human CFH, any one or more of rs529825; rs800292; rs3766404; rs1061147; rs1061170; and rs203674; any one of more of intron 2 (IVS2 or insTT); rs2274700; exon 10A; and rs375046; one or both of rs529825 and rs800292; one or more of rs1061147, rs1061170 and rs203674; at least one of rs529825 and rs800292; and rs3766404; and at least one of rs1061147, rs1061170 and rs203674; at least rs529825, rs800292, rs3766404, rs1061170, and rs203674; and/or exon 22 (R1210C). See. e.g., Hartman et al., 2006, "HTRA1 promoter polymorphism in wet age-related macular degeneration" *Science* 314:989-92, incorporated herein by reference.

In certain embodiments, the analysis of CFHR1 and/or CFHR3 polymorphisms can be combined with analysis of polymorphisms in the HTRA1 gene (also known as the PRSS11 gene), the complement factor B (BF) gene, and/or the complement component 2 (C2) gene. Genetic variants of the HTRA1 gene that may be detected include, but are not limited to, at least one of rs10490924, rs11200638, rs760336, and rs763720. Each of the single nucleotide polymorphisms (SNPs) within the HTRA1 gene are associated with increased risk of developing AMD. The genetic variants of the BF gene that may be detected include the presence of an A or G at rs641153 of the BF gene, or an R or Q at position 32 of the BF protein; and/or an A or T at rs4151667 of the BF gene, or L or H at position 9 of the BF protein. The genetic variants of the C2 protein that may be detected include a G or T at rs547154 of the C2 gene; and/or a C or G at rs9332379 of the C2 gene, or E of D at position 318 of the C2 protein. See, e.g., Gold et al., 2006 "Variation in factor B (BF) and complement component 2 (C2) genes is associated with age-related macular degeneration" *Nat Genet.* 38:458-62.

In addition, the analysis of CFHR1 and/or CFHR3 polymorphisms can be combined with an analysis of protein markers associated with AMD. The protein markers may include, but are not limited to, fibulin-3, vitronectin, β-crystallin A2, β-crystallin A3, β-crystallin A4, β-crystallin S, glucose-regulated protein 78 kD (GRP-78), calreticulin, 14-3-3 protein epsilon, serotransferrin, albumin, keratin, pyruvate carboxylase, villin 2, complement 1q binding protein/hyaluronic acid binding protein ("complement 1q component"), amyloid A (a1 amyloid A), amyloid P component, C5 and C5b-9 terminal complexes, HLA-DR, fibrinogen, Factor X, prothrombin, complements 3,5 and 9, complement reactive protein (CRP), HLA-DR, apolipoprotein A, apolipoprotein E, antichymotrypsin, p2 microglobulin, thrombospondin, elastin, collagen, ICAM-1, LFA1, LFA3, B7, IL-1, IL-6, IL-12, TNF-alpha, GM-CSF, heat shock proteins, colony stimulating factors (GM-CSF, M-CSFs), and IL-10.

4. Therapeutic Methods

In an embodiment, the invention provides methods of treatment and/or prophylaxis of diseases associated with a deletion within a CFHR1 and/or CFHR3 gene, or with reduced amount or activity of a CFHR1 and/or CFHR3 gene product, though the administration of a CFHR1 or CFHR3 polypeptide, or at least one portion of a CFHR1 and/or a CFHR3 polypeptide, or mixtures thereof, to a subject. In one instance, the disease is vascular disease.

In an embodiment, the invention provides methods of treatment and/or prophylaxis of diseases associated with an absence of a deletion within a CFHR1 and/or CFHR3 gene, or with unchanged or increased amount or activity of a CFHR1 and/or CFHR3 gene product, though the administration of at least one agent that reduces or inhibits CFHR1 or CFHR3 polypeptide to a subject. In one instance, the disease is AMD.

4.1 Prevention and Treatment of Vascular Disorders

A subject identified as having an elevated likelihood of developing a vascular disorder (e.g., aneurysm) can be treated by administering CFHR1 and/or CFHR3 polypeptides or biologically active fragments or variants thereof. The therapeutic polypeptide can be administered systemically (e.g., by intravenous infusion) or locally (e.g., directly to an organ or tissue, such as the eye or the liver). The polypeptides may have the sequence of wild-type (naturally occurring) polypeptides or may have an amino acid sequence substantially identical to the naturally occurring form.

CFHR1 and CFHR3 polypeptides or biologically active fragments or variants thereof may be isolated from blood (serum or plasma) or produced using conventional recombinant technology (see Ausubel et al., 2004, CURRENT PROTOCOLS IN MOLECULAR BIOLOGY, Greene Publishing and Wiley-Interscience, New York). Recombinant expression generally involved introducing the CFHR1 or CFHR3 gene into an expression vector that include a promoter to drive transcription of the DNA which is adapted for expression in prokaryotic (e.g., *E. coli*) and eukaryotic (e.g., yeast, insect or mammalian cells) hosts. Suitable host cells include bacteria such as *E. coli*, yeast, filamentous fungi, insect cells, and mammalian cells, which are typically immortalized, including mouse, hamster, human, and monkey cell line. Usually, the promoter is a eukaryotic promoter for expression in a mammalian cell. Usually, transcription regulatory sequences comprise a heterologous promoter and optionally an enhancer, which is recognized by the host cell. Commercially available expression vectors can be used. Expression vectors can include host-recognized replication systems, amplifiable genes, selectable markers, host sequences useful for insertion into the host genome, and the like.

In another embodiment the recombinant CFHR1 or CFHR3 is a full-length polypeptide, a variant thereof, or fragment thereof. In one embodiment the fragment is a biologically active fragment. In this context, a biologically active CFHR1 or CFHR3 polypeptide has an activity associated with wild-type CFHR1 or CFHR3. For example, in some embodiments the fragment has heparin and/or CRP and/or C3b-protein binding activity. Preferably the fragment has substantial sequence identity to at least a portion of the wild-type proteins. Biologically active fragments may comprise varying lengths of sequence substantially identical to wild-type proteins, such as, for example, at least 100, 200, 500, 700, 900 or 1100 residues. Alternatively, biologically active fragments may comprise at least one SCR substantially identical to CFHR1 or CFHR3, preferably at least 2, 3, 4, or 5 SCRs.

In specific embodiments, the biologically active fragment includes at least SCR 6-7. In another embodiment, the biologically active fragment includes at least SCR 19-20. In another embodiment, the biologically active CFH includes at least SCR1.

In certain embodiments the therapeutic Factor H polypeptides are chimeric or fusion proteins, and comprise sequence from other proteins. For example, a therapeutic Factor H polypeptide may contain portions of human CFHR1 or CFHR3 as well as portions comprised, at least in part, of SCR (or CCP) consensus domains from other proteins (e.g., CR1, MCP, DAF, C4BP, CR2, CFH) and/or artificial SCR(CCP) consensus sequences. See U.S. Pat. No. 5,545,619, incorporated herein by reference.

4.1.1 Therapeutic Compositions Containing CFHR1 or CFHR3 Polypeptides

The invention provides therapeutic preparations of CFHR1 or CFHR3 polypeptides, which may be wild-type or variants (e.g., neutral or protective variants), and may be full length forms, truncated forms, or biologically active fragments, including splice variants and recombinant fusion proteins. Therapeutic CFHR1 or CFHR3 polypeptides can be made recombinantly. Therapeutic proteins can be recombinantly produced (e.g., in cultured bacterial or eukaryotic cells) and purified using methods well known in the art and described herein. Alternatively, CFHR1 or CFHR3 polypeptides can be isolated from cultured RPE cells (e.g., primary cultures) or other cells that express CFHR1 or CFHR3 endogenously. Recombinant or purified polypeptides subject to FDA approval must be tested for potency and identity, be sterile, be free of extraneous material, and all ingredients in a product (i.e., preservatives, diluents, adjuvants, and the like) must meet standards of purity, quality, and not be deleterious to the patient.

The invention provides a composition comprising a CFHR1 polypeptide or CFHR3 polypeptide, and a pharmaceutically acceptable excipient or carrier. The term "pharmaceutically acceptable excipient or carrier" refers to a medium that is used to prepare a desired dosage form of a compound. A pharmaceutically acceptable excipient or carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. B. Kibbe ed. (American Pharmaceutical Assoc. 2000), disclose various carriers used in formulating pharmaceutical compositions and known techniques for the preparation thereof. The pharmaceutical compositions may be formulated using slow release agents or biodegradeable agents following techniques known in the art. In one embodiment, the pharmaceutically acceptable excipient is not deleterious to a mammal (e.g., human patient) if administered to the eye (e.g., by intraocular injection). For intraocular administration, for example and not limitation, the therapeutic agent can be administered in a Balanced Salt Solution (BSS) or Balanced Salt Solution Plus (BSS Plus) (Alcon Laboratories, Fort Worth, Tex., USA). In a related aspect, the invention provides a sterile container, e.g. vial, containing a therapeutically acceptable CFHR1 or CFHR3 polypeptides, optionally as a lyophilized preparation.

The amount of CFHR1 or CFHR3 polypeptide, or biologically active fragment thereof, to be administered to an individual can be determined. In one embodiment, exogenous CFHR1 or CFHR3 can be administered to an individual in an amount sufficient to achieve a level similar to the plasma concentration of CFHR1 or CFHR3 in a healthy individual, i.e., an amount sufficient to achieve a plasma level of from about 50 to 600 micrograms/ml, such as from about 100 to 560 micrograms/ml. The amount of CFHR1 or CFHR3 to be administered to an individual (e.g., a 160 pound subject) can be, for example and not for limitation, from about 10 milligrams to about 5000 milligrams per dose, from about 50 milligrams to about 2000 milligrams per dose, from about 100 milligrams to about 1500 milligrams per dose, from about 200 milligrams to about 1000 milligrams per dose, or from about 250 milligrams to about 750 milligrams per dose. The frequency with which CFHR1 or CFHR3 can be administered to an individual can be, for example and not for limitation, twice per day, once per day, twice per week, once per week, once every two weeks, once per month, once every two months, once every six months, or once per year. The amount and frequency of administration of CFHR1 or CFHR3 to an individual can be readily determined by a physician by monitoring the course of treatment.

Alternatively, the CFHR1 or CFHR3 polypeptide, or biologically active fragment thereof, can be administered to an individual using gene therapy or cell therapy methods as described further below.

4.1.2 Gene Therapy Methods

In another approach, CFHR1 or CFHR3 polypeptide is administered by in vivo expression of protein encoded by exogenous polynucleotide (i.e., via gene therapy). In one example, gene therapy involves introducing into a cell a vector that expresses CFHR1 or CFHR3 polypeptides or biologically active fragments of CFHR1 or CFHR3. The cell may be an endogenous cell (i.e., a cell from the patient) or engineered exogenous cell.

Vectors can be viral or nonviral. A number of vectors derived from animal viruses are available, including those derived from adenovirus, adeno-associated virus, retroviruses, pox viruses, alpha viruses, rhadboviruses, and papillomaviruses. Usually the viruses have been attenuated to no longer replicate (see, e.g., Kay et al. 2001, *Nature Medicine* 7:33-40).

The nucleic acid encoding the polypeptide is typically linked to regulatory elements, such as a promoters and an enhancers, which drive transcription of the DNA in the target cells of an individual. The promoter may drive expression of the gene in all cell types. Alternatively, the promoter may drive expression of the CFHR1 or CFHR3 gene only in specific cell types, for example, in cells of the retina, the liver or the kidney. The regulatory elements, operably linked to the nucleic acid encoding the polypeptide, are often cloned into a vector.

As will be understood by those of skill in the art, gene therapy vectors contain the necessary elements for the transcription and translation of the inserted coding sequence (and may include, for example, a promoter, an enhancer, other regulatory elements). Promoters can be constitutive or inducible. Promoters can be selected to target preferential gene expression in a target tissue, such as the RPE (for recent reviews see Sutanto et al., 2005, "Development and evaluation of the specificity of a cathepsin D proximal promoter in the eye" *Curr Eye Res.* 30:53-61; Zhang et al., 2004, "Concurrent enhancement of transcriptional activity and specificity of a retinal pigment epithelial cell-preferential promoter" *Mol. Vis.* 10:208-14; Esumi et al., 2004, "Analysis of the VMD2 promoter and implication of E-box binding factors in its regulation" *J Biol Chem* 279:19064-73; Camacho-Hubner et al., 2000, "The *Fugu rubripes* tyrosinase gene promoter targets transgene expression to pigment cells in the mouse" *Genesis.* 28:99-105; and references therein).

Suitable viral vectors include DNA virus vectors (such as adenoviral vectors, adeno-associated virus vectors, lentivirus vectors, and vaccinia virus vectors), and RNA virus vectors (such as retroviral vectors). In one embodiment, an adeno-associated viral (AAV) vector is used. For recent reviews see Auricchio et al., 2005, "Adeno-associated viral vectors for retinal gene transfer and treatment of retinal diseases" *Curr Gene Ther.* 5:339-48; Martin et al., 2004, Gene therapy for optic nerve disease, *Eye* 18: 1049-55; Ali, 2004, "Prospects for gene therapy" *Novartis Found Symp.* 255:165-72; Hennig et al., 2004, "AAV-mediated intravitreal gene therapy reduces lysosomal storage in the retinal pigmented epithelium and improves retinal function in adult MPS VII mice" *Mol Ther.* 10:106-16; Smith et al., 2003, "AAV-Mediated gene transfer slows photoreceptor loss in the RCS rat model of retinitis pigmentosa" *Mol Ther.* 8:188-95; Broderick et al., 2005, "Local administration of an adeno-associated viral vector expressing IL-10 reduces monocyte infiltration and subsequent photoreceptor damage during experimental autoimmune uveitis" *Mol. Ther.* 12:369-73; Cheng et al., 2005, "Efficient gene transfer to retinal pigment epithelium cells with long-term expression. *Retina* 25:193-201; Rex et al.," Adenovirus-mediated delivery of catalase to retinal pigment epithelial cells protects neighboring photoreceptors from photo-oxidative stress. *Hum Gene Ther.* 15:960-7; and references cited therein).

Gene therapy vectors must be produced in compliance with the Good Manufacturing Practice (GMP) requirements rendering the product suitable for administration to patients. The present invention provides gene therapy vectors suitable for administration to patients including gene therapy vectors that are produced and tested in compliance with the GMP requirements. Gene therapy vectors subject to FDA approval must be tested for potency and identity, be sterile, be free of extraneous material, and all ingredients in a product (i.e., preservatives, diluents, adjuvants, and the like) must meet standards of purity, quality, and not be deleterious to the patient. For example, the nucleic acid preparation is demonstrated to be mycoplasma-free. See, e.g, Islam et al., 1997, An academic centre for gene therapy research and clinical grade manufacturing capability, *Ann Med* 29, 579-583.

Methods for administering gene therapy vectors are known. In one embodiment, CFHR1 or CFHR3 expression vectors are introduced systemically (e.g., intravenously or by infusion). In one embodiment, expression vectors are introduced locally (i.e., directly to a particular tissue or organ, e.g., liver). In one embodiment, expression vectors are introduced directly into the eye (e.g., by intraocular injection). As will be understood by those of skill in the art, the promoter chosen for the expression vectors will be dependent upon the target cells expressing the CFHR1 or CFHR3 polypeptides. In some embodiments, a cell type-specific promoter is used and in other embodiments, a constitutive or general promoter is used. For recent reviews see, e.g., Dinculescu et al., 2005, "Adeno-associated virus-vectored gene therapy for retinal disease" *Hum Gene Ther.* 16:649-63; Rex et al., 2004, "Adenovirus-mediated delivery of catalase to retinal pigment epithelial cells protects neighboring photoreceptors from photo-oxidative stress" *Hum Gene Ther.* 15:960-7; Bennett, 2004, "Gene therapy for Leber congenital amaurosis" *Novartis Found Symp.* 255:195-202; Hauswirth et al., "Range of retinal diseases potentially treatable by AAV-vectored gene therapy" *Novartis Found Symp.* 255:179-188, and references cited therein).

Thus in one aspect, the invention provides a preparation comprising a gene therapy vector encoding a CFHR1 or CFHR3 polypeptide, optionally a viral vector, where the gene therapy vector is suitable for administration to a human subject and in an excipient suitable for administration to a human subject (e.g., produced using GLP techniques). Optionally the gene therapy vector comprises a promoter that is expressed preferentially or specifically in retinal pigmented epithelium cells.

Nonviral methods for introduction of CFHR1 or CFHR3 gene sequences, such as encapsulation in biodegradable polymers (e.g., polylactic acid (PLA); polyglycolic acid (PGA); and co-polymers (PLGA) can also be used (for recent reviews see, e.g., Bejjani et al., 2005, "Nanoparticles for gene delivery to retinal pigment epithelial cells" *Mol. Vis.* 11:124-32; Mannermaa et al., 2005, "Long-lasting secretion of transgene product from differentiated and filter-grown retinal pigment epithelial cells after nonviral gene transfer" *Curr Eye Res.* 2005 30:345-53; and references cited therein). Alternatively, the nucleic acid encoding a CFHR1 or CFHR3 polypeptide may be packaged into liposomes, or the nucleic acid can be delivered to an individual without packaging without using a vector.

4.1.3. Cell Therapy Methods

In another approach, CFHR1 or CFHR3 polypeptide is administered by in vivo expression of protein encoded by endogenous or exogenous CFHR1 or CFHR3 polynucleotide (i.e., via cell therapy). For example, hepatocyte transplantation has been used as an alternative to whole-organ transplantation to support many forms of hepatic insufficiency (see, e.g., Ohashi et al., Hepatocyte transplantation: clinical and experimental application, *J Mol Med.* 2001 79:617-30). According to this method, hepatocytes or other CFHR1- or CFHR3-expressing cells are administered (e.g., infused) to a patient in need of treatment. These cells migrate to the liver or other organ, and produce the therapeutic protein. Also see, e.g., Alexandrova et al., 2005, "Large-scale isolation of human hepatocytes for therapeutic application" *Cell Transplant.* 14(10):845-53; Cheong et al., 2004, "Attempted treatment of factor H deficiency by liver transplantation" *Pediatr Nephrol.* 19:454-8; Ohashi et al., 2001, "Hepatocyte transplantation: clinical and experimental application" *J Mol. Med.* 79:617-30; Serralta et al., 2005, "Influence of preservation solution on the isolation and culture of human hepatocytes from liver grafts" *Cell Transplant.* 14(10):837-43; Yokoyama et al., 2006, "In vivo engineering of metabolically active hepatic tissues in a neovascularized subcutaneous cavity" *Am. J. Transplant.* 6(1):50-9; Dhawan et al., 2005, "Hepatocyte transplantation for metabolic disorders, experience at King's College hospital and review of literature." *Acta Grastroenterol. Belg.* 68(4):457-60; Bruns et al., 2005, "injectable liver: a novel approach using fibrin gel as a matrix for culture and intrahepatic transplantation of hepatocytes" *Tissue Eng.* 11 (11-12):1718-26. Other cell types that may be used include, for illustration and not limitation, kidney and pancreatic cells. In one embodiment, the administered cells are engineered to express a recombinant form of the CFHR1 or CFHR3 protein.

In another, related approach, therapeutic organ transplantation is used. Most of the body's systemic CFHR1 and CFHR3 is produced by the liver, making transplantation of liver tissue the preferred method. See, Gerber et al., 2003, "Successful (?) therapy of hemolytic-uremic syndrome with factor H abnormality" *Pediatir Nephrol.* 18:952-5.

In another approach, a CFHR1 or CFHR3 protein is delivered to the back of the eye by injection into the eye (e.g., intravitreal) or via encapsulated cells. Neurotech's Encapsulated Cell Technology (ECT), as an example, is a unique technology that allows for the sustained, longterm delivery of therapeutic factors to the back of the eye. See (http://www.neurotech.fr). ECT implants consist of cells that have been genetically modified to produce a specific therapeutic protein that are encapsulated in a semi-permeable hollow fiber membrane. The cells continuously produce the therapeutic protein that diffuses out of the implant and into the eye (Bush et al., 2004, "Encapsulated cell-based intraocular delivery of ciliary neurotrophic factor in normal rabbit: dose-dependent effects on ERG and retinal histology" *Invest Opthalmol Vis Sci.* 45:2420-30.). CNTF delivered to the human eye by ECT devices was recently shown to be completely successful and associated with minimal complications in 10 patients enrolled in a Phase I clinical trial (Sieving et al., 2006, "Ciliary neurotrophic factor (CNTF) for human retinal degeneration: phase I trial of CNTF delivered by encapsulated cell intraocular implants" *Proc Natl Acad Sci USA* 103(10):3896-901). Also see et al., 2003, "Photoreceptor protection by cardiotrophin-1 in transgenic rats with the rhodopsin mutation s334ter" *IOVS,* 44(9):4069-75; Tao et al., 2002, "Encapsulated Cell-Based Delivery of CNTF Reduces Photoreceptor Degeneration in Animal Models of Retinitis Pigmentosa" IOVS, 43 10:3292-3298; and Hammang et al., U.S. Pat. No. 6,649,184. In one embodiment of the present invention, a form of CFHR1 or CFHR3 is expressed in cells and administered in an encapsulated form. In one embodiment, the cells used are the NTC-201 human RPE line (ATCC # CRL-2302) available from the American Type Culture Collection P.O. Box 1549, Manassas, Va. 20108.

4.2 Prevention and Treatment of AMD

A subject identified as having an elevated likelihood of developing AMD, exhibiting symptoms of AMD, or susceptible to AMD, can be treated by reducing the expression, activity or amount of a gene product of the CFHR1 and/or CFHR3 genes. Any method of reducing levels of CFHR1 or CFHR3 in the eye or systemically may be used for treatment including, for example, inhibiting transcription of a CFHR1 or CFHR3 gene, inhibiting translation of CFHR1 or CFHR3RNA, decreasing the amount or activity of CFHR1 or CFHR3 proteins (e.g., by plasmaphoresis, antibody-directed plasmaphoresis, or complexing with a CFHR1 or CFHR3 binding moiety (e.g., heparin or antibody), or by administration of inhibitory nucleic acids. In some embodiments levels of CFHR1 or CFHR3 are preferentially reduced in the eye (e.g., RPE) relative to other tissues. For illustration and not limitation, several methods are briefly described below.

4.2.1 Inhibitory Nucleic Acids

Inhibitory nucleic acids are known and include antisense nucleic acids, interfering RNAs, ribozymes and others (see, e.g., Gomes et al., 2005, "Intraocular delivery of oligonucleotides" *Curr Pharm Biotechnol.* 6:7-15; and Henry et al., 2004, "Setting sights on the treatment of ocular angiogenesis using antisense oligonucleotides" *Trends Pharmacol Sci* 25:523-7; PCT Publications WO 98/53083; WO 99/32619; WO 99/53050; WO 00/44914; WO 01/36646; WO 01/75164; WO 02/44321; and U.S. Pat. No. 6,107,094; Sui et al., 2002, "A DNA vector-based RNAi technology to suppress gene expression in mammalian cells" *Proc Natl Acad Sci USA* 99:5515-20; and Kasahara and Aoki, 2005, "Gene silencing using adenoviral RNA vector in vascular smooth muscle cells and cardiomyocytes" *Methods Mol. Med.* 112:155-72; U.S. Pat. No. 6,180,399; U.S. Pat. No. 5,869,254; U.S. Pat. No. 6,025,167; U.S. Pat. No. 5,854,038; U.S. Pat. No. 5,591,610; U.S. Pat. No. 5,667,969; U.S. Pat. No. 5,354,855;U.S. Pat. No. 5,093,246; U.S. Pat. No. 5,180,818; U.S. Pat. No. 5,116,742; U.S. Pat. No. 5,037,746; and U.S. Pat. No. 4,987,071; Dawson et al., 2000, "Hammerhead ribozymes selectively suppress mutant type I collagen mRNA in osteogenesis imperfecta fibroblasts" *Nucleic Acids Res.* 28:4013-20; Blalock et al., 2004 "Hammerhead ribozyme targeting connective tissue growth factor mRNA blocks transforming growth factor-beta mediated cell proliferation" *Exp Eye Res.* 78:1127-36; Kuan et al., 2004, "Targeted gene modification using triplex-forming oligonucleotides" *Methods Mol. Biol.* 262:173-94.

It will be understood that inhibitory nucleic acids can be administered as a pharmaceutical composition or using gene therapy or cell therapy methods.

4.2.2 Antibodies and Antibody Therapy

In one aspect, an anti-CFHR1 or anti-CFHR3 binding agents (e.g., antibodies) that reduce the activity or amount of the proteins is administered to an individual with or at risk for AMD. The antibody can be administered systemically or locally (see, e.g., Gaudreault et al., 2005, "Preclinical pharmacokinetics of Ranibizumab (rhuFabV2) after a single intravitreal administration" *Invest Ophthalmol Vis Sci.* 46:726-33).

In one embodiment, an anti-CFHR1 antibody specifically binds an epitope of CFHR1, in particular human CFHR1. In certain embodiments, an anti-CFHR1 antibody specifically binds an epitope located within the amino-terminus of a CFHR1 polypeptide. In particular, an anti-CFHR1 antibody specifically binds an epitope located between amino acids 1-143 of SEQ ID NO: 4 as shown in FIG. 6. In other embodiments, an anti-CFHR1 antibody specifically binds an epitope within the CFHR1 short consensus repeats (SCRs) 6 and/or 7 as shown in FIG. 1. The amino acid sequence of CFHR1SCR6 is 35% homologous to the corresponding CFH SCR, and the amino acid sequence of CFHR SCR7 is 45% homologous to the corresponding CFH SCR. Anti-CFHR1 antibodies of the invention specifically bind CFHR1 and do not cross-react with CFH or other factor H related proteins including CFHT, CFHR2, CFHR3, CFHR4, or CFHR5. A variety of immunoassay formats may be used to select antibodies that are specifically immunoreactive with a particular protein. For example, solid-phase ELISA immunoassays are routinely used to select monoclonal antibodies specifically immunoreactive with an antigen. See Harlow and Lane (1988) Antibodies, A Laboratory Manual, Cold Spring Harbor Publications, New York. Epitope mapping of the CFHR1 protein is within the skill of the art to determine epitopes that are most immunogenic for the generation of anti-CFHR1 antibodies.

In another embodiment, an anti-CFHR3 antibody specifically binds an epitope of CFHR3, in particular human CFHR3. In certain embodiments, an anti-CFHR3 antibody specifically binds an epitope located within the carboxyl-terminus of a CFHR3 polypeptide. For example, an anti-CFHR3 antibody may specifically bind to an epitope between amino acids 144-330 of SEQ ID NO: 6 as shown in FIG. 6. In other embodiments, an anti-CFHR3 antibody specifically binds an epitope within the CHFR3 SCRs 8, 19 and/or 20 as shown in FIG. 1. The amino acid sequence of CFHR3SCR8 is 63% homologous to the corresponding CRH SCR, the amino acid sequence of CFHR3SCR19 is 62% homologous to the corresponding CFH SCR, and the amino acid sequence of CFHR3SCR20 is 36% homologous to the corresponding CFH SCR. Anti-CFHR3 antibodies of the invention specifically bind CFHR3 and do not cross-react with CFH or other factor H related proteins including CFHT, CFHR1, CFHR2, CFHR4, or CFHR5. Epitope mapping of the CFHR3 protein is within the skill of the art to determine epitopes that may be immunogenic for the generation of anti-CFHR3 antibodies.

It is understood that each of the antibodies discussed above can be an intact antibody, for example, a monoclonal antibody. Alternatively, the binding protein can be an antigen binding fragment of an antibody, or can be a biosynthetic antibody binding site. Antibody fragments include Fab, Fab', (Fab')$_2$ or Fv fragments. Techniques for making such antibody fragments are known to those skilled in the art. A number of biosynthetic antibody binding sites are known in the art and include, for example, single Fv or sFv molecules, described, for example, in U.S. Pat. No. 5,476,786. Other biosynthetic antibody binding sites include bispecific or bifunctional binding proteins, for example, bispecific or bifunctional antibodies, which are antibodies or antibody fragments that bind at least two different antigens. For example, bispecific binding proteins can bind CFHR1, CFHR3, and/or another antigen. Methods for making bispecific antibodies are known in art and, include, for example, by fusing hybridomas or by linking Fab' fragments. See, e.g., Songsivilai et al. (1990) CLIN. EXP. IMMUNOL. 79: 315-325; Kostelny et al. (1992) J. IMMUNOL. 148: 1547-1553.

Anti-CFHR1 and anti-CFHR3 antibodies can be produced using techniques well known in the art. Monoclonal antibodies can be produced using standard fusion techniques for forming hybridoma cells. See G. Kohler, et al., *Nature*, 256: 456 (1975). Alternatively, monoclonal antibodies can be produced from cells by the method of Huse, et al., Science, 256:1275 (1989).

It is understood that the CDRs of the antibodies described herein confer the binding specificity to CFHR1 or CFHR3.

The antibodies described herein can be used as diagnostic and/or therapeutic agents. It is understood that the antibodies of the invention can be modified to optimize performance depending upon the intended use of the antibodies. For example, when the antibody is being used as a therapeutic agent, the antibody can be modified to reduce its immunogenicity in the intended recipient. Alternatively or in addition, the antibody can be fused or coupled to another protein or peptide, for example, a growth factor, cytokine, or cytotoxin. Such modifications can be achieved by using routine gene manipulation techniques known in the art.

Various techniques for reducing the antigenicity of antibodies and antibody fragments are known in the art. These techniques can be used to reduce or eliminate the antigenicity of the antibodies of the invention. For example, when the antibodies are to be administered to a human, the antibodies preferably are engineered to reduce their antigenicity in humans. This process often is referred to as humanization. Preferably, the humanized binding proteins have the same or substantially the same affinity for the antigen as the original non-humanized binding protein it was derived from.

In one well known humanization approach, chimeric proteins are created in which immunoglobulin constant regions of antibodies from one species, e.g., mouse, are replaced with immunoglobulin constant regions from a second, different species, e.g., a human. In this example, the resulting antibody is a mouse-human chimera, where the human constant region sequences, in principle, are less immunogenic than the counterpart murine sequences. This type of antibody engineering is described, for example, Morrison, et al. (1984) *Proc. Nat. Acad. Sci.* 81: 6851-6855, Neuberger et al., 1984, *Nature* 312: 604-608; U.S. Pat. Nos. 6,893,625 (Robinson); 5,500,362 (Robinson); and 4,816,567 (Cabilly).

In another approach, known as CDR grafting, the CDRs of the light and heavy chain variable regions of an antibody of interest are grafted into frameworks (FRs) from another species. For example, murine CDRs can be grafted into human FR sequences. In some embodiments, the CDRs of the light and heavy chain variable regions of an anti-CFHR1 antibody or an anti-CFHR3 antibody are grafted into human FRs or consensus human FRs. In order to create consensus human FRs, FRs from several human heavy chain or light chain amino acid sequences are aligned to identify a consensus amino acid sequence. CDR grafting is described, for example, in U.S. Pat. Nos. 7,022,500 (Queen); 6,982,321 (Winter); 6,180,370 (Queen); 6,054,297 (Carter); 5,693,762 (Queen); 5,859,205 (Adair); 5,693,761 (Queen); 5,565,332 (Hoogenboom); 5,585,089 (Queen); 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In addition, it is possible to create fully human antibodies in mice. In this approach, human antibodies are prepared using a transgenic mouse in which the mouse's antibody-producing genes have been replaced by a substantial portion of the human antibody producing genes. Such mice produce human immunoglobulin instead of murine immunoglobulin molecules. See, e.g., WO 98/24893 (Jacobovitz et al.) and Mendez et al., 1997, *Nature Genetics* 15: 146-156. Fully human anti-CFHR1 and/or anti-CFHR3 monoclonal antibodies can be produced using the following approach. Transgenic mice containing human immunoglobulin genes are immunized with the antigen of interest, e.g., CFHR1 or CFHR3. Lymphatic cells from the mice then are obtained from the mice, which are then fused with a myeloid-type cell line to prepare immortal hybridoma cell lines. The hybridoma cell lines are screened and selected to identify hybridoma cell lines that produce antibodies specific to CFHR1 or CFHR3.

5. Drug Screening/Antagonists of Risk Variant Factor H or Variant CFHR5

The invention provides a drug screening method for screening for agents for use in treating vascular disorders. The method involves combining (i) a cell that expresses CFHR3 and/or CFHR1 polypeptides; and (ii) a test agent; b) measuring the level of CFHR3 and/or CFHR1 gene expression in the cell and c) comparing the level of CFHR3 and/or CFHR1 gene expression in the cell with a reference value, where the reference value is the level of CFHR3 and/or CFHR1 gene expression in the absence of the test agent, where a higher level of CFHR3 and/or CFHR1 gene expression in the presence of the test agent indicates the test agent may be useful for treating the vascular disorders. Compounds from natural product libraries or synthetic combinatorial libraries may be screened. The level of CFHR3 and/or CFHR1 gene expression using a variety of approaches including measuring protein levels, measuring mRNA levels or other methods.

In one embodiment the method involves combining (i) a cell that expresses CFHR3 and/or CFHR1 polypeptides; and (ii) a test agent; b) measuring the level of CFHR3 and/or CFHR1 polypeptides produced by the cell (e.g., secreted into the medium); and c) comparing the level of CFHR3 and/or CFHR1 polypeptides secreted into the medium in the presence of the test agent with a reference value, said reference value being the level of CFHR3 and/or CFHR1 polypeptides produced (or secreted into the medium) in the absence of the test agent, where a higher level of CFHR3 and/or CFHR1 polypeptides secreted into the medium in the presence of the test agent indicates the test agent may be useful for treating the vascular disorders. Compounds from natural product libraries or synthetic combinatorial libraries may be screened.

6. Identifying Protective Forms of Complement Factor H Proteins

As described above, deletions at the CFHR1 and CFHR3 loci are linked to the presence of a protective haplotype. Protective haplotypes and protective forms of CFH proteins are described in Hageman et al., 2005, *Proc. Natl. Acad. Sci. U.S.A.* 102:7227-32 and U.S. patent publication No. 20070020647. In one aspect, the invention provides a method for identifying a CFH protein likely to protect against development of AMD when administered to a subject having, or at risk of developing, AMD. The method involves identifying a subject with a deletion in the DNA sequence between the 3' end of exon 22 of the complement factor H(CFH) gene and the 5' end of exon 1 of complement Factor H-related 4 (CFHR4) gene on human chromosome 1; determining the sequence of the CFH gene encoded by the gene contained in the chromosome containing the deletion; and determining the sequence of the protein encoded by the CFH gene, wherein said protein is different from wild-type CFH, said protein being a CFH protein likely to protect against AMD development. The invention also provides a protective CFH protein obtained using the method. U.S. patent publication No.

20070020647 discloses the use of protective forms of CFH protein to protect against AMD development and to treat AMD.

7. Kits and Diagnostic Devices

The invention provides reagents, devices and kits for detecting CFHR1 or CFHR3 deletions. A number of assay systems are known in the art, and it is within the skill of the art to arrive at means to determine the presence of variations associated with vascular disorders or AMD. The kit reagents, such as multiple primers, multiple probes, combinations of primers, or combinations of probes, may be contained in separate containers prior to their use for diagnosis or screening. In an embodiment, the kit contains a first container containing a probe, primer, or primer pair for a first CFHR1 or CFHR3 allele described herein, and a second container containing a probe, primer, or primer pair for a second CFHR1 or CFHR3 allele described herein.

The kits may contain one or more pairs of CFHR1 and/or CFHR3 allele-specific oligonucleotides hybridizing to different forms of a polymorphism. The allele-specific oligonucleotides may be provided immobilized on a substrate.

The invention also provides devices and reagents useful for diagnostic, prognostic, drug screening, and other methods are provided. In one aspect, a device comprising immobilized primer(s) or probe(s) specific for detecting deletions in the CFHR1 and/or CFHR3 genes and optionally also including immobilized primer(s) or probe(s) specific for detecting polymorphic sites in CFH that are associated with AMD. Exemplary probes and polymorphic sites are described in U.S. patent publication No. 20070020647.

In one aspect, a device comprising immobilized primer(s) or probe(s) specific for one or more Factor H and/or CFHR5 and/or CFHR1 and/or CFHR3 gene products (polynucleotides or proteins) is provided. The primers or probes can bind polynucleotides (e.g., based on hybridization to specific polymorphic sites) or polypeptides (e.g., based on specific binding to a variant polypeptide).

In one embodiment, an array format is used in which a plurality (at least 2, usually at least 3 or more) of different primers or probes are immobilized. The term "array" is used in its usual sense and means that each of a plurality of primers or probes, usually immobilized on a substrate, has a defined location (address) e.g., on the substrate. The number of primers or probes on the array can vary depending on the nature and use of the device. For example, a dipstick format array can have as few as 2 distinct primers or probes, although usually more than 2 primers or probes, and often many more, will be present. One method for attaching the nucleic acids to a surface is by making high-density oligonucleotide arrays (see, Fodor et al., 1991, *Science* 251:767-73; Lockhart et al., 1996, *Nature Biotech* 14:1675; and U.S. Pat. Nos. 5,578,832; 5,556,752; and 5,510,270). It is also contemplated that, in some embodiments, a device comprising a single immobilized probe can be used.

In one embodiment, an array format is used in which a plurality (at least 2, usually at least 3 or more) of different primers or probes are immobilized. The term "array" is used in its usual sense and means that each of a plurality of primers or probes, usually immobilized on a substrate, has a defined location (address) e.g., on the substrate. The number of primers or probes on the array can vary depending on the nature and use of the device.

In one embodiment, the immobilized probe is an antibody or other CFHR1 or CFHR3 binding moiety.

It will be apparent to the skilled practitioner guided by this disclosure than various polymorphisms and haplotypes can be detected, and used in combination with a deletion in the DNA sequence between the 3' end of exon 22 of the complement factor H(CFH) gene and the 5' end of exon 1 of complement Factor H-related 4 (CFHR4) gene on human chromosome 1, to assess the propensity of an individual to develop a Factor H related condition. Examples of CFH polymorphisms that may be assayed for include the following SNPs and combinations of SNPs: rs529825; rs800292; rs3766404; rs1061147; rs1061170; rs203674; and optionally including exon 22 (R1210C). In one embodiment the array includes primers or probes to determine the allele at least one of the following polymorphic sites: rs529825; rs800292; intron 2 (UVS2 or insTT); rs3766404; rs1061147; rs1061170; exon 10A; rs203674; rs375046; and optionally including exon 22 (R1210C). In an embodiment the array includes primers or probes to determine the allele at least one of the following polymorphic sites: (a) rs3753394; (b) rs529825; (c) rs800292; (d) intron 2 (IVS2 or insTT); (e) rs3766404; (f) rs1061147; (g) rs1061170; (h) rs2274700; (i) rs203674; (j) rs3753396; 0) rs1065489; and optionally including exon 22 (R1210C). In one embodiment, the array includes primers or probes to determine the allele at least one of the following polymorphic sites: rs800292 (162V); IVS2 (-18insTT); rs1061170 (Y402H); and rs2274700 (A473A). In one embodiment, the array includes primers or probes to determine the allele at least one of the following polymorphic sites: rs9427661 (-249T>C); rs9427662 (-20T>C); and rs12097550 (P46S).

The array can include primers or probes to determine the allele at two of the above sites, at least three, at least four, at least five or at least six. In one embodiment the primers or probes distinguish alleles at rs529825. In one embodiment the primers or probes distinguish alleles at rs800292. In one embodiment the primers or probes distinguish alleles at rs3766404. In one embodiment the primers or probes distinguish alleles at rs1061147. In one embodiment the primers or probes distinguish alleles at rs0161170. In one embodiment the primers or probes distinguish alleles at rs203674. In one embodiment the primers or probes distinguish alleles at exon 22 (R 210C). In one embodiment the primers or probes distinguish alleles at rs529825 and rs800292. In one embodiment the primers or probes distinguish alleles at two or three of rs1061147, rs1061170 and rs203674. In one embodiment the primers or probes distinguish alleles at rs529825 and rs800292, at rs3766404, two or three of rs1061147, rs0161170 and rs203674. In one embodiment the primers or probes distinguish alleles at rs529825, rs800292, rs3766404, rs1061170 and rs203674. In one embodiment, the primers or probes distinguish alleles at exon 22 (R1210C) and at rs529825; at rs800292; at rs3766404; at rs1061147; at rs1061170; at rs203674; at rs529825 and rs800292; at two or three of rs1061147, rs1061170 and rs203674; at rs529825 and rs800292, rs3766404, and two or three of rs1061147, rs1061170 and rs203674; or at rs529825, rs800292, rs3766404, rs1061170 and rs203674. In one embodiment, the primers or probes distinguish alleles at (a) any one or more of rs529825; rs800292; rs3766404; rs1061147; rs1061170; and rs203674; (b) any one of more of intron 2 (IVS2 or insTT); rs2274700; exon 10A; and rs375046; (c) one or both of rs529825 and rs800292; (d) one or more of rs1061147, rs1061170 and rs203674; (e) at least one of rs529825 and rs800292; and rs3766404; and at least one of rs1061147, rs1061170 and rs203674; (f) at least rs529825, rs800292, rs3766404, rs1061170, and rs203674; (g) exon 22 (R1210C); (h) exon 22 (R1210C) and any of (a)-(g); or (i) any one or more of rs529825; rs800292; rs3766404; rs1061147; rs1061170; rs203674; intron 2 (IVS2 or insTT); rs2274700; exon 10A; rs375046; and exon 22 (R1210C) and any one or more of rs9427661, rs9427662 and rs12097550.

The array can include primers or probes to determine the allele at two of the above sites, at least three, at least four, at least five or at least six. In one embodiment the primers or probes distinguish alleles at rs529825. In one embodiment the primers or probes distinguish alleles at rs800292. In one embodiment the primers or probes distinguish alleles at intron 2 (IVS2 or insTT). In one embodiment the primers or probes distinguish alleles at rs3766404. In one embodiment the primers or probes distinguish alleles at rs1061147. In one embodiment the primers or probes distinguish alleles at rs1061170. In one embodiment the primers or probes distinguish alleles at exon 10A. In one embodiment the primers or probes distinguish alleles at rs2274700. In one embodiment the primers or probes distinguish alleles at rs203674. In one embodiment the primers or probes distinguish alleles at rs375046. In one embodiment the primers or probes distinguish alleles at exon 22 (R1210C). In one embodiment the primers or probes distinguish alleles at rs529825 and rs800292. In one embodiment the primers or probes distinguish alleles at two or three of rs1061147, rs1061170 and rs203674. In one embodiment the primers or probes distinguish alleles at of rs529825 and rs800292, at intron 2, at rs3766404, at two or three of rs1061147, rs1061170 and rs203674, at exon 10A, at rs2274700, and at rs375046. In one embodiment the primers or probes distinguish alleles at rs529825, rs800292, intron 2 (IVS2 or insTT), rs3766404, rs1061170, exon 10A, rs2274700, rs203674, and rs375046. In one embodiment, the primers or probes distinguish alleles at exon 22 (R1210C) and at either at rs529825; at rs800292; at intron 2 (IVS2 or insTT); at rs3766404; at rs1061147; at rs1061170; at rs2274700, at exon 10A; at rs203674; at rs375046; at rs529825 and rs800292; at two or three of rs1061147, rs1061170 and rs203674; at rs529825 and rs800292, intron 2 (IVS2 or insTT), rs3766404, two or three of rs1061147, rs1061170 and rs203674, rs2274700, exon 10A, and rs375046; or at rs529825, rs800292, intron 2 (IVS2 or insTT), rs3766404, rs1061170, rs2274700, exon 10A, rs203674, and rs375046. In one embodiment, the device distinguishes any combination of alleles at the sites listed above in the context of kits.

In one embodiment, the substrate comprises fewer than about 1000 distinct primers or probes, often fewer than about 100 distinct primers or probes, fewer than about 50 distinct primers or probes, or fewer than about 10 distinct primers or probes. As used in this context, a primer is "distinct" from a second primer if the two primers do not specifically bind the same polynucleotide (i.e., such as cDNA primers for different genes). As used in this context, a probe is "distinct" from a second probe if the two probes do not specifically bind the same polypeptide or polynucleotide (i.e., such as cDNA probes for different genes). Primers or probes may also be described as distinct if they recognize different alleles of the same gene (i.e., CFH or CFHR5). Thus, in one embodiment diagnostic devices of the invention detect alleles of CFH only, CFHR5 only, CFH and CFHR5 only, or CFH, CFHR5 and up to 20, preferably up to 10, or preferably up to 5 genes other than CFH and/or CFHR5. That is, the device is particularly suited to screening for AMD and related complement-associated diseases. In one embodiment, the device comprises primers or probes that recognize CFH and/or one or more of CFHR1-5 only. In a related embodiment, the device contains primers and probes for up to 20, preferably up to 10, or preferably up to 5 other genes than CFH or CFHR1-5.

In one embodiment, the immobilized primer(s) is/are an allele-specific primer(s) that can distinguish between alleles at a polymorphic site in the Factor H or CHRF5 gene. Exemplary allele-specific primers to identify alleles at polymorphic sites in the Factor H gene are shown in TABLE 16A of U.S. patent publication No. 20070020647, incorporated by reference in its entirety for all purposes. The immobilized allele-specific primers hybridize preferentially to nucleic acids, either RNA or DNA, that have sequences complementary to the primers. The hybridization may be detected by various methods, including single-base extension with fluorescence detection, the oligonucleotide ligation assay, and the like (see Shi, M. M., 2001, Enabling large-scale pharmacogenetic studies by high-throughput mutation detection and genotyping technologies" Clin. Chem. 47(2):164-172). Microarray-based devices to detect polymorphic sites are commercially available, including Affymetrix (Santa Clara, Calif.), Protogene (Menlo Park, Calif.), Genometrix (The Woodland, Tex.), Motorola BioChip Systems (Northbrook, Ill.), and Perlegen Sciences (Mountain View, Calif.).

The invention provides reagents and kits for detecting CFHR1 and/or CFHR3 proteins. A number of assay systems are known in the art, and it is within the skill of the art to arrive at means to determine the presence or absence of CFHR1 and/or CFHR3, or variant or truncated forms thereof, associated with vascular disorders or AMD. The kit reagents, such as anti-CFHR3 or CFHR1 antibodies or other CFHR3 or CFHR1 binding moieties, may be contained in separate containers prior to their use for diagnosis or screening. In an embodiment, the kit contains a first container containing an antibody or binding moiety that specifically binds to CFHR1 protein, or a variant or truncated form thereof, and a second container containing an antibody or binding moiety that specifically binds to CFHR3 protein, or a variant or truncated form thereof. In some embodiments the binding moieties is an aptamer, such as a nucleic acid aptamer. Aptamers are RNA or DNA molecules selected in vitro from vast populations of random sequence that recognize specific ligands by forming binding pockets. Aptamers are nucleic acids that are capable of three dimensional recognition that bind specific proteins or other molecules. See, e.g., US20050176940 "Aptamers and Antiaptamers".

Thus, the invention provides reagents for conducting the screening methods of the invention, comprising a binding moiety capable of specifically binding CFHR1 and/or CFHR3 protein or a portion thereof (e.g., a labeled binder that reacts preferentially with CFHR1 and/or CFHR3 protein or a portion thereof or a labeled binder that reacts preferentially with CFHR1 mRNA and/or CFHR3 mRNA or a portion thereof, or a labeled binder that reacts preferentially with CFHR1 DNA and/or CFHR3 DNA). The binding moiety may comprise, for example, a member of a ligand-receptor pair, i.e., a pair of molecules capable of having a specific binding interaction (such as antibody-antigen, protein-protein, nucleic acid-nucleic acid, protein-nucleic acid, or other specific binding pair known in the art). Optionally the binding moiety is labeled (e.g., directly labeled) or is accompanied by a labeled molecule that reacts with the binding moiety (indirectly labeled). Detectable labels can be directly attached to or incorporated into the detection reagent by chemical or recombinant methods. Examples of detectable labels include, but are not limited to, radioisotopes, fluorophores, chromophores (e.g., colored particles), mass labels, electron dense particles, magnetic particles, spin labels, and molecules that emit chemiluminescence. Methods for labeling are well known in the art.

The kits may contain an instruction manual with instructions how to use the anti-CFHR3 or CFHR1 antibodies or other CFHR3 or CFHR1 binding moieties to detect CFHR3 or CFHR1 proteins in body fluids or in tissue samples.

The kits may contain a control antibody or binding moiety. An example of a control antibody or binding moiety is an antibody that specifically binds to CFH protein.

The kits may contain one or more pairs of antibodies or binding moieties that specifically bind to different (i.e., not wild-type or full-length) forms (e.g., variant or truncated) of CFHR1 or CFHR3 proteins.

In one embodiment, the antibodies or binding moieties are immobilized to a solid support such as an ordered array.

In one embodiment, the antibodies or binding moieties are used in Western blots.

EXAMPLES

Example 1

Polymerase chain reaction (PCR) amplification, single-strand conformation polymorphism (SSCP) analysis and direct DNA sequencing were used to characterize a deletion in the CFHR3 and CFHR1 genes located between the CFH and CFHR4 genes on chromosome 1. Examples of primers that can be used for PCR amplification of the CFH gene and CFH-related genes 1 to 5 are shown in Table 1A. Examples of primers that can be used for SSCP analysis of the CFH and CFHR3 genes are shown in Table 1B. Examples of primers that can be used for direct DNA sequencing of the CFH, CFHR1 and CFHR3 genes are shown in Table 1C and 1D.

TABLE 1

Primers Used for Detecting the CFH and CFHR1-5 Genes

| | Forward 5'-3' | Reverse 5'-3' | Product Size (bp) |
|---|---|---|---|
| A. PCR Primers | | | |
| CFH ex22 | GGTTTGGATAGTGT TTTGAG (SEQ ID NO: 14) | ACCGTTAGTTTTCC AGG (SEQ ID NO: 15) | 521 |
| CFHR1 ex6 | AGTCGGTTTGGACA GTG (SEQ ID NO: 7) | GCACAAGTTGGATA CTCC (SEQ ID NO: 8) | 321 |
| CFHR2 ex4 | TGTGTTCATTCAGT GAG (SEQ ID NO: 16) | ATAGACATTTGGTA GGC (SEQ ID NO: 17) | 510 |
| CFHR3 ex3 | TCATTGCTATGTCC TTAGG (SEQ ID NO: 10) | TCTGAGACTGTCGT CCG (SEQ ID NO: 11) | 263 |
| CFHR4 ex3 | CTACAATGGGACTT TCTTAG (SEQ ID NO: 18) | TTCACACTCATAGG AGGAC (SEQ ID NO: 19) | 378 |
| CFHR5 ex2 | AACCCTTTTTCCCA AG (SEQ ID NO: 20) | CACATCCTTCTCTA TTCAC (SEQ ID NO: 21) | 193 |
| B. SSCP Primers | | | |
| CFH ex22 | GGTTTGGATAGTGT TTTGAG (SEQ ID NO: 14) | ATGTTGTTCGCAAT GTG (SEQ ID NO: 22) | 283 |
| CFHR3 ex3 | TCATTGCTATGTCC TTAGG (SEQ ID NO: 10) | TCTGAGACTGTCGT CCG (SEQ ID NO: 11) | 263 |
| C. Sequencing Primers | | | |
| CFH ex22 | GGTTTGGATAGTGT TTTGAG (SEQ ID NO: 14) | ACCGTTAGTTTTCC AGG (SEQ ID NO: 15) | 521 |
| CFHR3 ex3 seq | TTTTGGATGTTTAT GCG (SEQ ID NO: 12) | AAATAGGTCCGTTG GC (SEQ ID NO: 13) | |
| CFHR1 ex6 | AGTCGGTTTGGACA GTG (SEQ ID NO: 7) | GCACAAGTTGGATA CTCC (SEQ ID NO: 8) | 321 |

TABLE 1-continued

| | Forward 5'-3' | Reverse 5'-3' | Product |
|---|---|---|---|
| D. Primers used for detecting the CFH and CFHR1-5 genes and results | | | |
| CFH (ex22) | GGTTTGGATAGTGT TTTGAG (SEQ ID NO: 14) | ATGTTGTTCGCAAT GTG (SEQ ID NO: 22) | Yes |
| CFH (ex22) | GGTTTGGATAGTGT TTTGAG (SEQ ID NO: 14) | ACCGTTAGTTTTCC AGG (SEQ ID NO: 15) | Yes |
| IVS 5' to CFHR3 | CACGCTATTTGAAA GACAAACTT (SEQ ID NO: 23) | AAGCAACCCTGCTC TACAATGT (SEQ ID NO: 24) | Yes |
| IVD 5' to CFHR3 | GGAACCACATGGGT CAAATG (SEQ ID NO: 25) | GCACAACAAATAAA ACTAGCAAATCAT (SEQ ID NO: 26) | Yes |
| IVD 5' to CFHR3 | ATTGCTGCAATCTC AGAAGAAAA (SEQ ID NO: 27) | TCAAAACGAACAAA CAAACAGG (SEQ ID NO: 28) | No |
| CFHR3 (ex2) | TGCGTAGACCATAC TTTCCAG (SEQ ID NO: 29) | CTCTCTTTAATCTT TTAAAGTTTTATAC ATGTG (SEQ ID NO: 30) | No |
| CFHR3 (ex3) | TTTTGGATGTTTAT GCG (SEQ ID NO: 12) | AAATAGGTCCGTTG GC (SEQ ID NO: 13) | No |
| CFHR3 (ex3) | TCATTGCTATGTCC TTAGG (SEQ ID NO: 10) | TCTGAGACTGTCGT CCG (SEQ ID NO: 11) | No |
| CFHR1 (ex2) | TAAAGTGCTGTGTT TGTATTTGC (SEQ ID NO: 31) | GTGATTATTTTGTT ACCAACAGC (SEQ ID NO: 32) | No |
| CFHR1 (ex6) | AGTCGGTTTGGACA GTG (SEQ ID NO: 7) | GCACAAGTTGGATA CTCC (SEQ ID NO: 8) | No |
| CFHR1 (ex6) | CATAGTCGGTTTGG ACAGTG (SEQ ID NO: 9) | GCACAAGTTGGATA CTCC (SEQ ID NO: 8) | No |
| CFHR2 | TCCTTTTCTAGTTC ATTAACATA (SEQ ID NO: 33) | AGTGATATGACACA TGCTGAC (SEQ ID NO: 34) | Yes |
| CFHR2 | CTACAGACTAACTT TCAATAATTT (SEQ ID NO: 35) | GATACTTTTACATT TTCTTATGAT (SEQ ID NO: 36) | Yes |
| CFHR2 | ACATAGTTATATGA TCGTTTTGAGT (SEQ ID NO: 37) | ACAGAGAAAGAACT TACTAATTG (SEQ ID NO: 38) | Yes |
| CFHR2 | TGTGTTCATTCAGT GAG (SEQ ID NO: 16) | ATAGACATTTGGTA GGC (SEQ ID NO: 17) | Yes |
| CFHR4 | AGTATTAAATTGTT CAGTCCAG (SEQ ID NO: 39) | AAACTAGTGTAAGA ATGTATGAT (SEQ ID NO: 40) | Yes |
| CFHR4 | TAAGTTGAAAGAGA TCTAAACAC (SEQ ID NO: 41) | ACTGTATGTAAGAT TATGAAAGTAT (SEQ ID NO: 42) | Yes |
| CFHR4 | CTACAATGGGACTT TCTTAG (SEQ ID NO: 18) | TTCACACTCATAGG AGGAC (SEQ ID NO: 19) | Yes |

TABLE 1-continued

| CFHR5 | AACCCTTTTTCCCAAG (SEQ ID NO: 20) | CACATCCTTCTCTATTCAC (SEQ ID NO: 21) | Yes |

In a study directed toward further characterization of CFH and its associated haplotypes on chromosome 1q, a complete deletion of the entire CFHL1 and CFHL3 genes was identified. In examining SSCP gels generated using CFH exon 22 primers (Table 1), several additional patterns of variation were observed due to the amplification of CFHR1 in addition to CFH. By designing another set of CFH-specific primers, it was determined that there were no variations in exon 22 of CFH. CFHR1-specific primers were generated and used to identify a deletion of CFHR1. Further analysis of the CFHR1, CFHR2, CFHR3, CFHR4 and CFHR5 genes and intervening sequence 5' to CFHR3 (Table 1D) using specific primers revealed a deletion that extends across the entire length of the CFHR1 and CFHR3 genes. The precise boundaries of the complete deletion have not be determined, but the mapping of the boundaries is within the skill of the art.

SSCP analysis and direct DNA sequencing was used to determine the frequency of the homozygous deletion of the CFHR3 and CFHR1 genes in a set of 1074 patients with and without a clinical history of AMD. The cohort included patients who had other systemic diseases, including vascular diseases, irrespective of their AMD status. As shown in Table 2, homozygous deletion of the CFHR1 and CFHR3 genes was found in ~2.7% of the persons tested.

TABLE 2

Frequency of homozygous deletion of CFHR1 and CFHR3 genes

| Genotype* | Count | Percent |
|---|---|---|
| +/+, +/Δ | 1046 | 97.3% |
| Δ/Δ | 28 | 2.7% |
| +/+, +/Δ, Δ/Δ | 1074 | 100% |

*Genotype refers to the deletion (Δ) or non-deletion (+) of the CFHR1 and CFHR3 genes by SSCP analysis and direct sequencing.

Initial analysis suggested that the deletion homozygotes were more common in control individuals than in AMD cases. To determine whether there was an association of the homozygous deletion of the CFHR3 and CFHR1 genes with AMD, a subset of the above patient population was analyzed by SSCP analysis and direct DNA sequencing. As shown in Table 3, in a study of 576 AMD patients and 352 age-matched non-AMD control patients, deletion homozygotes make up 5.1% of controls and 1.2% of cases. The homozygous deletion of CFHR1 and CFHR3 is strongly associated with controls, with $\chi 2=10.2$ and P value=0.0014, demonstrating a highly significant protective effect of the homozygous CFHR1/CFHR3 deletion for AMD.

TABLE 3

Association of homozygous deletion of CFHR1 and CFHR3 genes with non-AMD

| | Genotype | Non-AMD patients | AMD patients |
|---|---|---|---|
| Count | +/+, +/Δ | 352 | 576 |
| Count | Δ/Δ | 18 | 7 |
| Frequency | +/+, +/Δ | 0.951 | 0.988 |
| Frequency | Δ/Δ | 0.049 | 0.012 |

*Genotype refers to the deletion (Δ) or non-deletion (+) of the CFHR1 and CFHR3 genes by SSCP analysis and direct sequencing.

To determine whether there was an association of the homozygous deletion of the CFHR3 and CFHR1 genes with vascular disorders, two subsets of the above patient population were analyzed by SSCP analysis and direct DNA sequencing. As shown in Table 4A, a study of 26 patients with abdominal aortic aneurysm (AAA) and 133 non-AAA patients revealed that the homozygous deletion of CFHR1 and CFHR3 was strongly associated with AAA, with $\chi 2=6.982329$ and P=0.0082. As shown in Table 4B, a second study of 86 patients with abdominal aortic aneurysm (AAA) and 221 non-AAA patients revealed that the homozygous deletion of CFHR1 and CFHR3 was associated with AAA, with $\chi 2=4.05$ and P=0.0442.

TABLE 4

Association of homozygous deletion of CFHR1 and CFHR3 genes with AAA

| | Genotype | Controls | AAA |
|---|---|---|---|
| A. Study 1 | | | |
| Count | +/+, +/Δ | 126 | 19 |
| Count | Δ/Δ | 7 | 7 |
| Total | +/+, +/Δ, Δ/Δ | 133 | 26 |
| B. Study 2 | | | |
| Count | +/+, +/Δ | 221 | 86 |
| Count | Δ/Δ | 12 | 11 |
| Total | +/+, +/Δ, Δ/Δ | 233 | 97 |

*Genotype refers to the deletion (Δ) or non-deletion (+) of the CFHR1 and CFHR3 genes by SSCP analysis and direct sequencing.

To determine whether previously identified protective haplotypes in the CFH gene were associated with the del (Δ) CFHR1 allele, haplotype analysis was performed. As shown in Tables 5A-5E, the relationship between the del (Δ) CFHR1 allele and SNPs in the CFH gene revealed strong linkage disequilibrium. The SNPs used in this haplotype analysis are described in U.S. patent publication No. 20070020647. In the table, letters refer to genotypes and numbers refer to SSCP shift patterns.

TABLE 5

CFH gene haplotype analysis in subjects with the del/del (Δ/Δ) CFHR1 allele

A. Promoter 1 to Exon 3

| | Promoter 1 | Promoter 4 rs3753394 C-257T | Exon 2 rs800292 I62V G184A | Exon 3a IVS2-18insTT | Exon 3 same SNP as 3a |
|---|---|---|---|---|---|
| 1 | AA | TT | GG | SS | SS |
| 2 | AA | CC | GG | SS | SS |
| 3 | AA | CT | GG | SS | SS |
| 4 | AA | CC | GG | SS + G100R het | SS + G100R het |
| 5 | AA | CT | GG | SS | SS |
| 6 | AA | CT | GG | SS | SS |
| 7 | AA | CC | GG | SS | SS |
| 8 | AA | TT | GG | SS | SS |
| 9 | AA | CT | GG | SS | SS |
| 10 | AA | CC | GG | SS | SS |

TABLE 5-continued

CFH gene haplotype analysis in subjects with the del/del (Δ/Δ) CFHR1 allele

| | | | | | |
|---|---|---|---|---|---|
| 11 | AA | CC | GG | SS | SS |
| 12 | AA | CC | GG | SS | SS |
| 13 | AA | CT | GG | SS | SS |
| 14 | | | GG | SS | SS |
| 15 | | | GG | SS | SS |
| 16 | | | GG | SS | SS |
| 17 | | | GG | SS | SS |
| 18 | | | GG | SS | SS |
| 19 | | | GG | SS | SS |
| 20 | | | GG | SS | SS |
| 21 | | | GA | SS | SS |
| 22 | | | GG | SS | SS |
| 23 | | | | SS | SS |
| 24 | | | | SS | SS |
| 25 | | | | SS | SS |
| 26 | | | | | SS |

B. IVS 6 to Exon 7b

| | IVS 6 shift | IVS 6 N or Del | IVS6 rs16840419 | IVS6 rs3766404 | Exon 7b rs1061147 A307A A921C |
|---|---|---|---|---|---|
| 1 | 3 | NN | GA | CT | CC |
| 2 | 5 | NDel | 5 (GG) | 5 (CC?) | CC |
| 3 | 2 | NN | GG | CC | CC |
| 4 | 2 | NN | GG | CC | CC |
| 5 | 3 | NN | GA | CT | CC |
| 6 | 1 | NN | AA | TT | AC |
| 7 | 5 | NDel | 5 (GG) | 5 (CC?) | CC |
| 8 | 1 | NN | AA | TT | CC |
| 9 | 3 | NN | GA | CT | CC |
| 10 | 2 | NN | GG | CC | CC |
| 11 | No DNA (3) | NN | No DNA (GA) | No DNA (CT) | AC |
| 12 | 2 | NN | GG | CC | CC |
| 13 | 1 | NN | AA | TT | CC |
| 14 | | | | | |
| 15 | | | | | |
| 16 | | | | | |
| 17 | | | | | |
| 18 | | | | | AA |
| 19 | | | | | |
| 20 | | | | | |
| 21 | | | | | |
| 22 | | | | | |
| 23 | | | | | |
| 24 | | | | | |
| 25 | | | | | |
| 26 | | | | | |

C. Exon 9 to Exon 16b

| | Exon 9 rs1061170 Y402H C1204T | Exon 10A CFHtrunc | Exon 10a rs2274700 A473A G2016A | Exon 13b rs3753396 Q672Q A2089G | Exon 16b rs375046 IVS15 |
|---|---|---|---|---|---|
| 1 | TT | | AA | AA | |
| 2 | TT | | | AA | AA |
| 3 | TT | 1 | AA | AA | AA |
| 4 | TT | 1 | AA | AA | AA |
| 5 | TT | 1 | AA | AA | 4 |
| 6 | CT | 1 | GA | AA | |
| 7 | TT | | | | AA |
| 8 | TT | 1 | AA | AA | AA |
| 9 | TT | 1 | AA | AA | AA |
| 10 | TT | 1 | AA | AA | AC? |
| 11 | CT | 1 | GA | AA | |
| 12 | TT | | | AA | |
| 13 | TT | | | | |
| 14 | TT | 1 | AA | | |
| 15 | TT | 1 | AA | | |
| 16 | CT | 1 | GA | | |
| 17 | TT | 1 | AA | AA | CC |
| 18 | CC | 1 | GG | | |
| 19 | TT | 1 | AA | | |
| 20 | TT | 1 | AA | | |
| 21 | TT | 1 | AA | | |
| 22 | TT | 1 | AA | | |
| 23 | TT | | | | |
| 24 | TT | | | | |
| 25 | TT | | | | |
| 26 | TT | | | | |

D. Exon 17a to Exon 19a

| | Exon 17a | Exon 17b A892V C2748T | Exon 18a rs1065489 E936D G2881T | Exon 18b rs1065489 E936D G2881T | Exon 19a rs534399 V1007L G3092T |
|---|---|---|---|---|---|
| 1 | 1 | CC | GG | GG | GG |
| 2 | 1 | CC | | | |
| 3 | 1 | CC | GG | GG | GG |
| 4 | 1 | CC | GG | GG | GG |
| 5 | 1 | CC | GG | GG | GG |
| 6 | 3 | CC | GG | GG | TT |
| 7 | 1 | | | | |
| 8 | 1 | CC | GG | GG | GG |
| 9 | 1 | CC | GG | GG | GG |
| 10 | 1 | CC | GG | GG | GG |
| 11 | 1 | CC | GG | GG | GG |
| 12 | 1 | CC | | | |
| 13 | 1 | CC | | | |
| 14 | | | | GG | |
| 15 | | | | GG | |
| 16 | | | | GG | |
| 17 | | | | GG | |
| 18 | 1 | CC | GG | GG | GG |
| 19 | | | | GG | |
| 20 | | | | GG | |
| 21 | | | | GG | |
| 22 | | | | GG | |
| 23 | | | | GG | |
| 24 | | | | GG | |
| 25 | | | | GG | |
| 26 | | | | GG | |

E. Exon 20b to Exon22 split (detects both CFH and CFHR1)

| | Exon 20b | Exon 22b 1191/1197/1210 | Exon 22split 1197 |
|---|---|---|---|
| 1 | 4 | 4 | 4 |
| 2 | | | 4 |
| 3 | 4 | 4 | 4 |
| 4 | 2 | 4 | 4 |
| 5 | 4 | 4 | 4 |
| 6 | 4 | 4 | 4 |
| 7 | | | 4 |
| 8 | 4 | 4 | 4 |
| 9 | 4 | 4 | 4 |
| 10 | 6 | 4 | 4 |
| 11 | 4 | 4 | 4 |
| 12 | | | 4 |
| 13 | | | 4 |
| 14 | | 4 | |
| 15 | 4 | 4 | |
| 16 | 4 | 4 | |
| 17 | | | |
| 18 | 4 | 4 | |
| 19 | 4 | 4 | |
| 20 | 6 | 4 | |
| 21 | 4 | 4 | |
| 22 | 4 | 4 | |
| 23 | 4 | 4 | |
| 24 | 4 | 4 | |
| 25 | 4 | 4 | |
| 26 | 4 | 4 | |

Also continued from top right:

| | | | |
|---|---|---|---|
| 18 | CC | 1 | GG |
| 19 | TT | 1 | AA |
| 20 | TT | 1 | AA |
| 21 | TT | 1 | AA |
| 22 | TT | 1 | AA |
| 23 | TT | | |
| 24 | TT | | |
| 25 | TT | | |
| 26 | TT | | |

As shown in Table 6, in two studies it was found that the deletion of the CFHR1 and CFHR3 genes was associated with 402T-containing haplotypes. This deletion is almost never found on the same 402C-containing haplotype as the major CFH risk allele, Y402H. The del (Δ) CFHR1 mutation is predominantly associated with the CFH H4 haplotype, a haplotype with T at position 1277 of the coding region of CFH (codon 402) shown previously shown to be protective for AMD. However, not every del (Δ) CFHR1 chromosome is on H4, and the protection of del/del (Δ/Δ) CFHR1 homozygotes for AMD is even stronger than H4 homozygotes. Heterozygous deletion of the CFHR3 and CFHR1 genes was detected by direct DNA sequencing of the CFH, CFHR1 and CFHR3 genes using a CFH exon 22 primer.

TABLE 6

Association of homozygous deletion of CFHR1 and CFHR3 genes with the TT genotype at position 1277 of the coding region of CFH (codon 402)

| Genotype | | CFH402 Genotype | | |
|---|---|---|---|---|
| | | TT | TC | CC |
| A. Study 1 | | | | |
| Count | +/+, +/Δ | 102 | 209 | 150 |
| Count | Δ/Δ | 11 | 2 | 0 |
| Count | +/+, +/Δ, Δ/Δ | 113 | 211 | 150 |
| B. Study 2 | | | | |
| Count | +/+, +/Δ | 192 | 393 | 283 |
| Count | Δ/Δ | 23 | 3 | 0 |
| Count | +/+, +/Δ, Δ/Δ | 215 | 396 | 283 |

*Genotype refers to the deletion (Δ) or non-deletion (+) of the CFHR1 and CFHR3 genes by SSCP analysis and direct sequencing.
**CFH402 Genotype refers to the nucleotide on both alleles at position 1277 of the coding region of human CFH. A T results in a tyrosine at codon 402, whereas a C results in a histidine at codon 402.
***Of the 474 patients, approximately 22 +/− 4% are heterozygous (+/Δ) for the deletion of the CFHR1 and CFHR3 genes, as determined by direct DNA sequencing.

Figure 3:
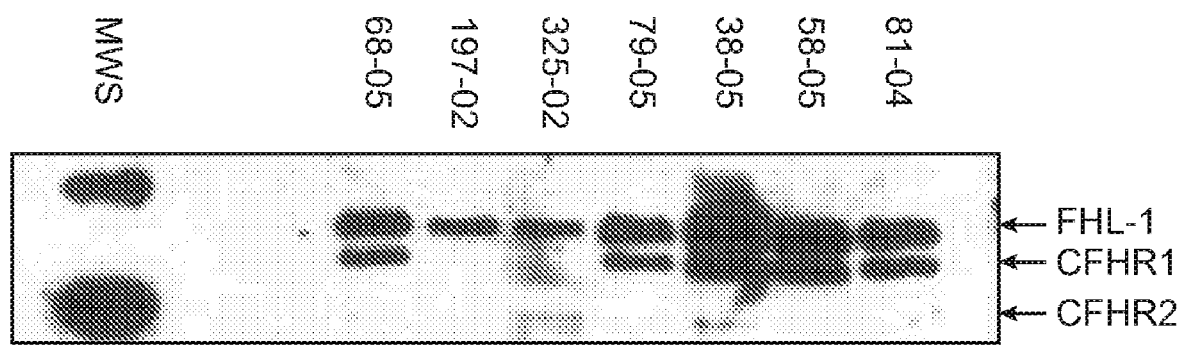
FIG. 3 shows a Western blot of serum proteins from seven patients using an anti-human CFH antibody. FHL-1, CFHR1 and CFHR2 indicate the positions of the truncated form of CFH, CFHR1 and CFHR2, respectively. The anti-human CFH antibody employed also cross-reacts with CFHR1 and CFHR2. No CFHR1 is detected in the serum of two patients (197-02 and 325-02) that have a homozygous deletion of the CFHR3 and CFHR1 genes, as determined by SSCP analysis and direct DNA sequencing.

By Western blotting, it was determined that CFHR1 protein, normally an abundant serum protein, is absent in sera derived from individuals homozygous for the CFHR1/CFHR3 deletion. FIG. 3 shows a representative Western blot of serum proteins from seven (out of a sample set of 52) patients using an anti-human CFH antibody. Serum proteins were separated by one-dimensional SDS-polyacrylamide gel electrophoresis and transferred to a nitrocellulose membrane. After transfer, the membrane was blocked with 5% non-fat dry milk, washed, and then incubated with a goat anti-human CFH (Calbiochem, 1:1000 dilution). After incubation, the membrane was washed, and then incubated with horse radish peroxidase-conjugated rabbit anti-goat 1 g antibody (Abcam, 1:4000 dilution). After incubation, the membrane was washed, and then incubated with extravidin (1:1500 dilution). Samples 197-02 and 325-02 were from patients with a TT 402 genotype (protective CFH H4 haplotype) and have homozygous deletion of CFHR1 and CFHR3 genes, as determined by SSCP analysis and direct sequencing. FIG. 3 shows that no CFHR1 is detected in the serum from patients having a homozygous deletion of the CFHR1 and CFHR3 genes.

Figure 4:
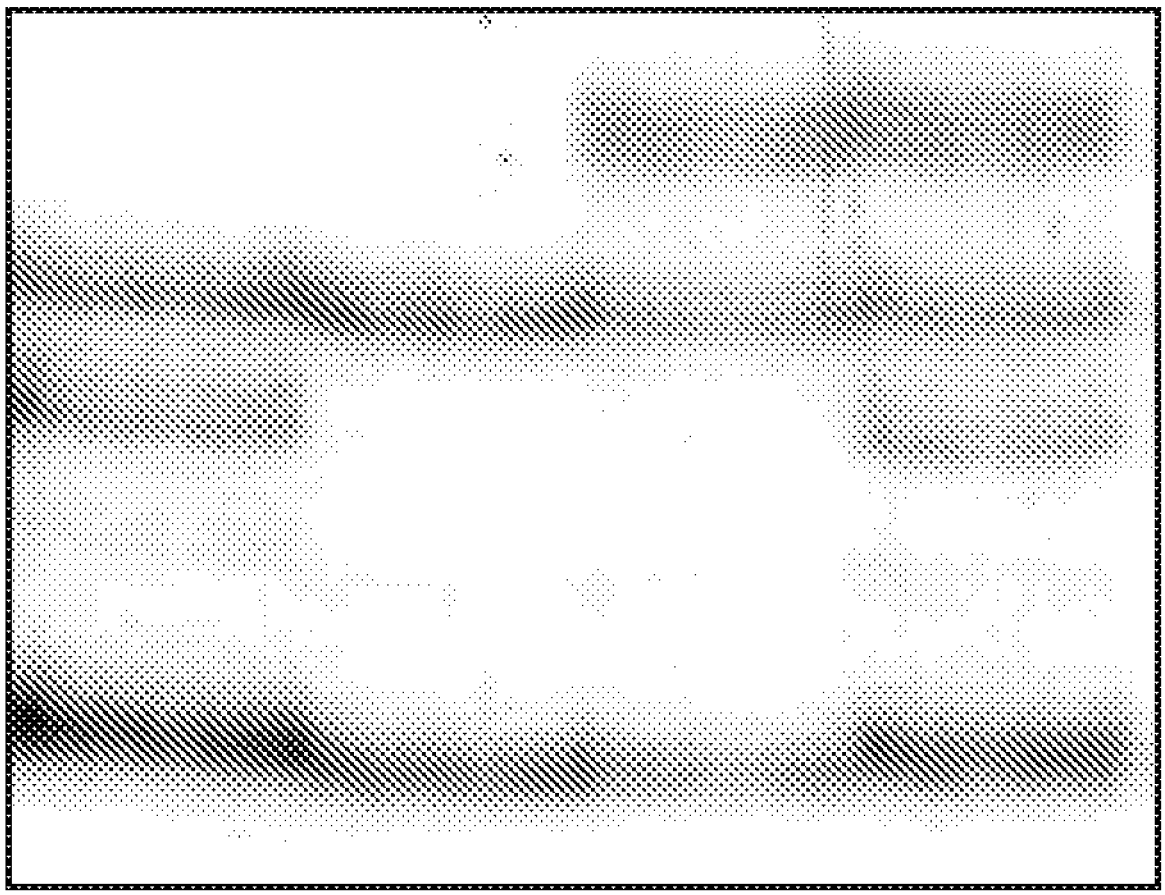
FIG. 4 shows a SSCP analysis of the CFH, CFHR3 and CFHR1 genes. 1, 2, 3, and 4 indicate four different SSCP patterns observed using primers from exon 22 of the CFH gene to PCR amplify DNA. SSCP patterns 1, 2 and 3 correspond to homozygous non-deletion or heterozygous deletion of CFHR3 and CFHR1, and pattern 4 corresponds to homozygous deletion of CFHR3 and CFHR1.

Western blotting using the same anti-human CFH antibody was used to detect CFH and CFHR1 in serum from an additional 40 patients, separated according to SSCP patterns using the CFH exon 22 primers. Patterns 1-3 correspond to homozygous, or heterozygous for, non-deletion of CFHR1 and CFHR3 (+/+, +/Δ), and pattern 4 corresponds to homozygous deletion of CFHR1 and CFHR3 (Δ/Δ) (see FIG. 4). All 10 of the serum samples from patients displaying SSCP pattern 4 show no CFHR1, whereas all 30 of the serum samples from patients displaying SSCP patterns 1-3 show at least some CFHR1 (data not shown). Thus, analysis of serum from individuals with a CFHR1 del/del (Δ/Δ) genotype shows that they lack any detectable CFHR1 protein. This protein analysis confirms that these individuals lack both the CFHR1 gene and encoded protein. Individuals who are heterozygous for deletion of CFHR1 and CFHR3 can be recognized by protein analysis of serum samples by virtue of the intensity of the band corresponding to CFHR 1 being roughly half the intensity in heterozygous (+/Δ) patients as compared to homozygous non-deletion (+/+) patients.

Figure 5:
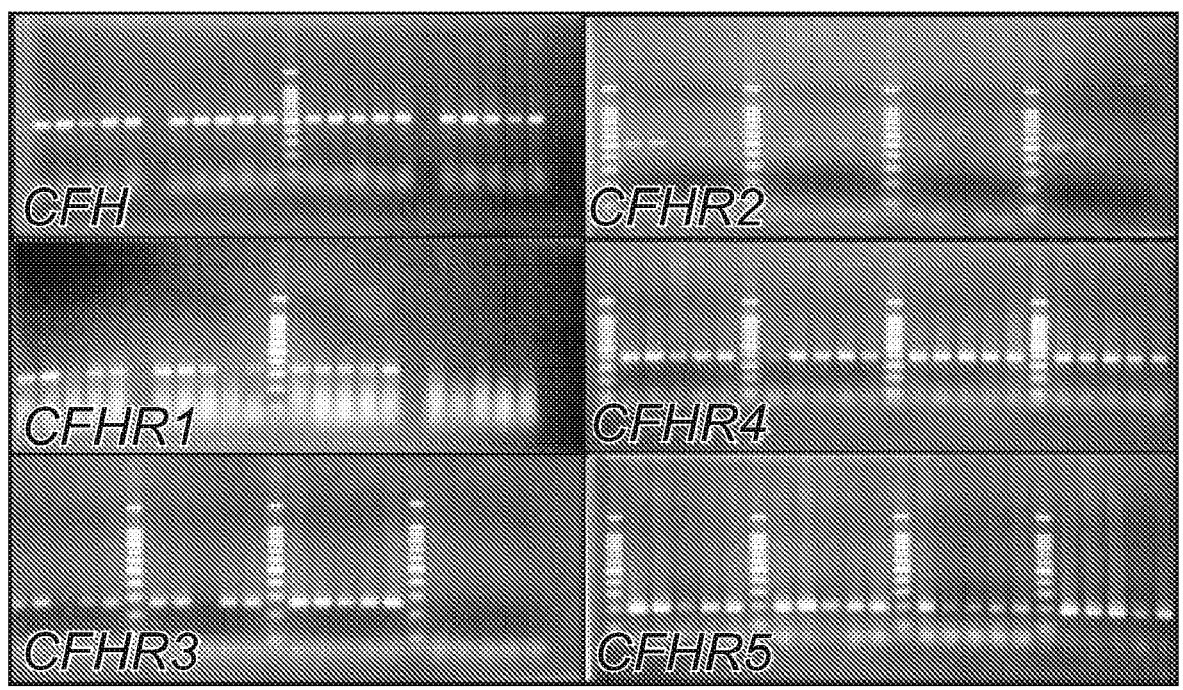
FIG. 5 shows a PCR analysis of the CFH and CFH-related genes 1 to 5 in leukocytes from 20 patients that are separated into four groups according to the SSCP patterns using the CFH exon 22 primers (patterns 1-4 are as described in FIG. 4). From left to right, in each panel (gel), 5 leukocyte-derived DNA samples each from patients displaying SSCP patterns 1, 2, 3 and 4 were subjected to PCR using primers specific for CFH, CFHR1, CFHR2, CFHR3, CFHR4 and CFHR5, as indicated. When SSCP analysis and direct DNA sequencing show a homozygous deletion of the CFHR3 and CFHR1 genes, no PCR amplifiable CFHR3 and CFHR1 DNA are detected.

PCR experiments using leukocyte-derived DNA were performed to confirm that patients having a homozygous deletion of CFHR1 and CFHR3 do not have CFHR1 and CFHR3 DNA. FIG. 5 shows a PCR analysis of CFH and CFHR1-5 from DNA samples from 20 patients, separated into four groups according to SSCP patterns using the CFH exon 22 primers mentioned above. Patterns 1-3 correspond to homozygous non-deletion or heterozygous deletion of CFHR1 and CFHR3 (+/+, +/Δ), and pattern 4 corresponds to homozygous deletion of CFHR1 and CFHR3 (Δ/Δ). From left to right, 5 samples each from patients displaying SSCP patterns 1, 2, 3 and 4 were subjected to PCR using primers specific for CFH, CFHR1, CFHR2, CFHR3, CFHR4 and CFHR5, as indicated. This figure shows that CFH, CFHR4 and CFHR5 DNA are amplified in all of the samples, whereas CFHR1 and CFHR3 DNA are amplified in samples from patients displaying SSCP patterns 1-3, but not from patients displaying SSCP pattern 4. The CFHR2DNA was amplified in some, but not all, of the samples. Thus, when SSCP and direct sequencing show a homozygous deletion of the CFHR1 and CFHR3 genes, no PCR amplifiable CFHR1 and CFHR3DNA are detected in samples.

Example 2

Production of Anti-CFHR1 and Anti-CFHR3 Monoclonal Antibodies

Mice will be immunized with recombinant human CFHR1 or CFHR3. Two mice with sera displaying the highest anti-CFHR1 and anti-CFHR3 activity by Enzyme Linked Immunosorbent Assay (ELISA) will be chosen for subsequent fusion and spleens and lymph nodes from the appropriate mice will be harvested. B-cells will be harvested and fused with an myeloma line. Fusion products will be serially diluted on one or more plates to near clonality. Supernatants from the resulting fusions will be screened for their binding to hCFHR1 or hCFHR3 by ELISA. Supernatants identified as containing antibodies to CFHR1 or CFHR3 will be further characterized by in vitro functional testing as discussed below. A panel of hybridomas will be selected and the hybridomas will be subcloned and expanded. The monoclonal antibodies will then be purified by affinity chromatography on Protein A/G resin under standard conditions.

Anti-CFHR1 and anti-CFHR3 antibodies may be further characterized by in vitro functional testing using complement activation assays well known in the art. For example, complement activation assays may be conducted in solution (e.g., fluid phase in blood) or on immobilized surfaces. Exemplary assays may measure the ability of the anti-CFHR1 and/or anti-CFHR3 antibodies to block or reduce CFH, C3b, heparin and/or C-reactive protein (CRP) binding to a substrate.

Although the present invention has been described in detail with reference to specific embodiments, those of skill in the art will recognize that modifications and improvements are within the scope and spirit of the invention, as set forth in the claims which follow. All publications and patent documents cited herein are incorporated herein by reference as if each

What is claimed is:

1. A screening method for determining a human subject's propensity to develop an abdominal aortic aneurysm and/or age-related macular degeneration (AMD) comprising:
analyzing a biological sample from the subject to detect the presence or absence of a deletion of at least 1000 bp in the region of chromosome 1 between the 3' end of exon 22 of the complement factor H (CFI-1) gene and the 5' end of exon 1 of complement Factor H-related 4 (CFHR4) gene
wherein the presence of a deletion indicates the subject is at increased risk of developing an abdominal aortic aneurysm and is at decreased risk of developing AMD.

2. The method of claim 1 wherein the presence or absence of the deletion is detected by assaying for a gene product encoded in chromosome 1 between the 3' end of exon 22 of the complement factor H (CFH) gene and the 5' end of exon 1 of complement Factor H-related 4 (CFHR4) gene, where the absence of the gene product, or a reduced level of expression of the gene product, indicates the presence of deletion.

3. The method of claim 2 wherein the presence or absence of a complement Factor H-related 1 (CFHR1) gene product and/or a complement Factor H-related 3 (CFHR3) gene product is detected, where the absence of a gene product is indicative of a deletion.

4. The method of claim 2 wherein the gene product is a protein.

5. The method of claim 3 wherein entire protein coding region of the CFHR3 gene is deleted.

6. The method of claim 3 wherein entire protein coding region of the CFHR1 gene is deleted.

7. The method of claim 1 comprising detecting a deletion of an intragenic sequence selected from a sequence between the CFHR3 gene and the CFHR1 gene and a sequence between the CFHR1 gene and the CFHR4 gene.

8. The method of claim 1 wherein the subject is homozygous for the deletion.

9. The method of claim 1 wherein the biological sample is blood, serum, urine or a tissue sample.

10. The method of claim 4 wherein the detection step comprises detecting a gene product using an immunoassay or mass spectroscopy.

11. The method of claim 1 wherein the presence or absence of the deletion is detected by assaying for a truncated CFHR1 or CFHR3 gene product, where detection of a truncated gene product is indicative of a deletion.

12. The method of claim 1 wherein the step comprising detecting the presence or absence of a deletion is performed by analyzing a chromosome or nucleic acid from the subject.

13. The method of claim 12 wherein the nucleic acid is DNA or RNA.

14. The method of claim 1 wherein the subject has a genotype of T at position 1277 of the coding region of the CFH gene of the chromosome comprising the deletion.

15. The method of claim 1 further comprising detecting genetic variants of complement factor H (CFH) gene com prising detecting one or a plurality of polymorphic sites selected from the group consisting of:
   a) any one or more of rs529825; rs800292; rs3766404; rs1061147; rs1061170; and rs203674;
   b) any one of more of intron 2 (IVS2 or insTT); rs2274700; exon 10A; and rs375046;
   c) one or both of rs529825 and rs800292;
   d) one or more of rs1061147, rs1061170 and rs203674;
   e) at least one of rs529825 and rs800292; and rs3766404; and at least one of rs1061147, rs1061170 and rs203674;
   f) at least rs529825, rs800292, rs3766404, rs1061170, and rs203674;
   g) exon 22 (R1210C); and
   h) exon 22 (R1210C) and any of (a)-(g).

16. The method of claim 1 further comprising detecting in a sample from the subject a macular degeneration-associated molecule selected from the group consisting of fibulin-3, vitronectin, β-crystallin A2, β-crystallin A3, β-crystallin A4, β-crystallin S, glucose-regulated protein 78 kD (GRP-78), calreticulin, 14-3-3 protein epsilon, serotransferrin, albumin, keratin, pyruvate carboxylase, villin 2, complement 1 q binding protein/hyaluronic acid binding protein ("complement 1 q component"), amyloid A (a1 amyloid A), amyloid P component, C5 and CSb-9 terminal complexes, HLA-DR, fibrinogen, Factor X, prothrombin, complements 3,5 and 9, complement reactive protein (CRP), HLA-DR, apolipoprotein A, apolipoprotein E, antichymotrypsin, p2 microglobulin, thrombospondin, elastin, collagen, ICAM-1, LFA1, LFA3, B7, IL-1, IL-6, IL-12, TNF-alpha, GM-CSF, heat shock proteins, colony stimulating factors (GM-CSF, M-CSFs), and IL-10.

17. The method of claim 1 further comprising detecting in a sample from the subject genetic variants of the HTRA1 gene comprising detecting a polymorphic site selected from the group consisting of: at least one of rs10490924, rs11200638, rs760336, and rs763720.

18. The method of claim 1 further comprising detecting in a sample from the subject genetic variants of the complement factor B (BF) gene and/or the complement component 2 (C2) gene comprising detecting a polymorphic site selected from the group consisting of:
   a) A or G at rs641153 of the BF gene, or R or Q at position 32 of the BF protein;
   b) A or T at rs4151667 of the BF gene, or L or H at position 9 of the BF protein;
   c) G or T at rs547154 of the C2 gene; and
   d) C or G at rs9332379 of the C2 gene, or E of D at position 318 of the C2 protein.

19. The method of claim 1 wherein the entire protein coding region of the CFHR3 gene is deleted.

20. The method of claim 1 wherein the entire protein coding region of the CFHR1 gene is deleted.

21. The method of claim 1 wherein the subject has a deletion of at least 10,000 bp in the genomic sequence encoding CFHR1 and/or CFHR3.

22. The method of claim 21 wherein the entire genomic sequence encoding CFHR3 is deleted.

23. The method of claim 21 wherein the entire genomic sequence encoding CFHR1 is deleted.

24. The method of claim 21 wherein at least a portion of the genomic sequence encoding CFHR1 and at least a portion of the genomic sequence encoding CFHR3 is deleted.

25. A screening method for determining a human subject's propensity to develop age-related macular degeneration (AMD) and/or abdominal aortic aneurysm (AAA) comprising analyzing the subject's genome to detect the presence or absence of a deletion of at least 10,000 bp in the genomic sequence encoding CFHR1 and/or CFHR3, wherein the presence of said deletion indicates the subject is at increased risk of developing an abdominal aortic aneurysm and is at decreased risk of developing AMD.

26. The method of claim 25 wherein the entire genomic sequence encoding CFHR3 is deleted.

27. The method of claim 25 wherein the entire genomic sequence encoding CFHR1 is deleted.

28. The method of claim 25 wherein at least a portion of the genomic sequence encoding CFHR1 and at least a portion of the genomic sequence encoding CFHR3 is deleted.

29. The method of claim 26 wherein the subject is homozygous for said deletion.

30. The method of claim 4 wherein the protein is CFHR1.

* * * * *

SEQUENCE LISTING

<160> NUMBER OF SEQ ID NOS: 42

<210> SEQ ID NO 1
<211> LENGTH: 3853
<212> TYPE: DNA
<213> ORGANISM: Homo sapiens

<400> SEQUENCE: 1

| | | | | | |
|---|---|---|---|---|---|
| atgagacttc | tagcaaagat | tatttgcctt | atgttatggg | ctatttgtgt | agcagaagat | 60 |
| tgcaatgaac | ttcctccaag | aagaaataca | gaaattctga | caggttcctg | gtctgaccaa | 120 |
| acatatccag | aaggcaccca | ggctatctat | aaatgccgcc | ctggatatag | atctcttgga | 180 |
| aatgtaataa | tggtatgcag | gaagggagaa | tgggttgctc | ttaatccatt | aaggaaatgt | 240 |
| cagaaaaggc | cctgtggaca | tcctggagat | actccttttg | gtacttttac | ccttacagga | 300 |
| ggaaatgtgt | ttgaatatgg | tgtaaaagct | gtgtatacat | gtaatgaggg | gtatcaattg | 360 |
| ctaggtgaga | ttaattaccg | tgaatgtgac | acagatggat | ggaccaatga | tattcctata | 420 |
| tgtgaagttg | tgaagtgttt | accagtgaca | gcaccagaga | atggaaaaat | tgtcagtagt | 480 |
| gcaatggaac | cagatcggga | ataccatttt | ggacaagcag | tacggtttgt | atgtaactca | 540 |
| ggctacaaga | ttgaaggaga | tgaagaaatg | cattgttcag | acgatggttt | ttggagtaaa | 600 |
| gagaaaccaa | agtgtgtgga | aatttcatgc | aaatccccag | atgttataaa | tggatctcct | 660 |
| atatctcaga | agattattta | taaggagaat | gaacgatttc | aatataaatg | taacatgggt | 720 |
| tatgaataca | gtgaaagagg | agatgctgta | tgcactgaat | ctggatggcg | tccgttgcct | 780 |
| tcatgtgaag | aaaaatcatg | tgataatcct | tatattccaa | atggtgacta | ctcacctta | 840 |
| aggattaaac | acagaactgg | agatgaaatc | acgtaccagt | gtagaaatgg | ttttatcct | 900 |
| gcaacccggg | gaaatacagc | caaatgcaca | agtactggct | ggatacctgc | tccgagatgt | 960 |
| accttgaaac | cttgtgatta | tccagacatt | aaacatggag | gtctatatca | tgagaatatg | 1020 |
| cgtagaccat | actttccagt | agctgtagga | aaatattact | cctattactg | tgatgaacat | 1080 |
| tttgagactc | cgtcaggaag | ttactgggat | cacattcatt | gcacacaaga | tggatggtcg | 1140 |
| ccagcagtac | catgcctcag | aaaatgttat | tttccttatt | tggaaaatgg | atataatcaa | 1200 |
| aatcatggaa | gaaagtttgt | acagggtaaa | tctatagacg | ttgcctgcca | tcctggctac | 1260 |
| gctcttccaa | aagcgcagac | cacagttaca | tgtatggaga | atggctggtc | tcctactccc | 1320 |
| agatgcatcc | gtgtcaaaac | atgttccaaa | tcaagtatag | atattgagaa | tgggtttatt | 1380 |
| tctgaatctc | agtatacata | tgccttaaaa | gaaaaagcga | aatatcaatg | caaactagga | 1440 |
| tatgtaacag | cagatggtga | aacatcagga | tcaattagat | gtgggaaaga | tggatggtca | 1500 |
| gctcaaccca | cgtgcattaa | atcttgtgat | atcccagtat | ttatgaatgc | cagaactaaa | 1560 |
| aatgacttca | catggtttaa | gctgaatgac | acattggact | atgaatgcca | tgatggttat | 1620 |
| gaaagcaata | ctggaagcac | cactggttcc | atagtgtgtg | gttacaatgg | ttggtctgat | 1680 |
| ttacccatat | gttatgaaag | agaatgcgaa | cttcctaaaa | tagatgtaca | cttagttcct | 1740 |
| gatcgcaaga | aagaccagta | taaagttgga | gaggtgttga | aattctcctg | caaaccagga | 1800 |

```
tttacaatag ttggacctaa ttccgttcag tgctaccact ttggattgtc tcctgacctc   1860
ccaatatgta aagagcaagt acaatcatgt ggtccacctc ctgaactcct caatgggaat   1920
gttaaggaaa aaacgaaaga agaatatgga cacagtgaag tggtggaata ttattgcaat   1980
cctagatttc taatgaaggg acctaataaa attcaatgtg ttgatggaga gtggacaact   2040
ttaccagtgt gtattgtgga ggagagtacc tgtggagata tacctgaact tgaacatggc   2100
tgggcccagc tttcttcccc tccttattac tatggagatt cagtggaatt caattgctca   2160
gaatcattta caatgattgg acacagatca attacgtgta ttcatggagt atggacccaa   2220
cttccccagt gtgtggcaat agataaactt aagaagtgca aatcatcaaa tttaattata   2280
cttgaggaac atttaaaaaa caagaaggaa ttcgatcata attctaacat aaggtacaga   2340
tgtagaggaa aagaaggatg gatacacaca gtctgcataa atggaagatg ggatccagaa   2400
gtgaactgct caatggcaca aatacaatta tgcccacctc cacctcagat tcccaattct   2460
cacaatatga caaccacact gaattatcgg gatggagaaa aagtatctgt tctttgccaa   2520
gaaaattatc taattcagga aggagaagaa attacatgca aagatggaag atggcagtca   2580
ataccactct gtgttgaaaa aattccatgt tcacaaccac ctcagataga acacggaacc   2640
attaattcat ccaggtcttc acaagaaagt tatgcacatg ggactaaatt gagttatact   2700
tgtgagggtg gtttcaggat atctgaagaa atgaaaacaa catgctacat gggaaaatgg   2760
agttctccac ctcagtgtga aggccttcct tgtaaatctc cacctgagat ttctcatggt   2820
gttgtagctc acatgtcaga cagttatcag tatggagaag aagttacgta caaatgtttt   2880
gaaggttttg gaattgatgg gcctgcaatt gcaaaatgct taggagaaaa atggtctcac   2940
cctccatcat gcataaaaac agattgtctc agtttaccta gctttgaaaa tgccatacc    3000 atgggagaga agaaggatgt gtataaggcg ggtgagcaag tgacttacac ttgtgcaaca   3060
tattacaaaa tggatggagc cagtaatgta acatgcatta tagcagatg gacaggaagg    3120 ccaacatgca gagacacctc ctgtgtgaat ccgcccacag tacaaaatgc ttatatagtg   3180
tcgagacaga tgagtaaata tccatctggt gagagagtac gttatcaatg taggagccct   3240
tatgaaatgt tggggatga agaagtgatg tgtttaaatg gaaactggac ggaaccacct   3300
caatgcaaag attctacagg aaaatgtggg cccctccac ctattgacaa tggggacatt   3360
acttcattcc cgttgtcagt atatgctcca gcttcatcag ttgagtacca atgccagaac   3420
ttgtatcaac ttgagggtaa caagcgaata acatgtagaa atggacaatg gtcagaacca   3480
ccaaaatgct acatccgtg tgtaatatcc cgagaaatta tggaaaatta acatagca     3540 ttaaggtgga cagccaaaca gaagctttat tcgagaacag gtgaatcagt tgaatttgtg   3600
tgtaaacggg gatatcgtct ttcatcacgt tctcacacat tgcgaacaac atgttgggat   3660
gggaaactgg agtatccaac ttgtgcaaaa agatagaatc aatcataaag tgcacacctt   3720
tattcagaac tttagtatta aatcagttct caatttcatt ttttatgtat tgttttactc   3780
ctttttattc atacgtaaaa ttttggatta atttgtgaaa atgtaattat aagctgagac   3840
cggtggctct ctt                                                     3853

<210> SEQ ID NO 2
<211> LENGTH: 1231
<212> TYPE: PRT
<213> ORGANISM: Homo sapiens

<400> SEQUENCE: 2
```

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Asn Thr Glu Ile
            20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Val Ile Met
            50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
                100                 105                 110

Thr Cys Asn Glu Gly Tyr Gln Leu Leu Gly Glu Ile Asn Tyr Arg Glu
            115                 120                 125

Cys Asp Thr Asp Gly Trp Thr Asn Asp Ile Pro Ile Cys Glu Val Val
            130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
            195                 200                 205

Ser Cys Lys Ser Pro Asp Val Ile Asn Gly Ser Pro Ile Ser Gln Lys
210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
            275                 280                 285

Glu Ile Thr Tyr Gln Cys Arg Asn Gly Phe Tyr Pro Ala Thr Arg Gly
            290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
            355                 360                 365

Trp Asp His Ile His Cys Thr Gln Asp Gly Trp Ser Pro Ala Val Pro
            370                 375                 380

Cys Leu Arg Lys Cys Tyr Phe Pro Tyr Leu Glu Asn Gly Tyr Asn Gln
385                 390                 395                 400

Asn His Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
```

-continued

```
                420                 425                 430
Glu Asn Gly Trp Ser Pro Thr Pro Arg Cys Ile Arg Val Lys Thr Cys
            435                 440                 445

Ser Lys Ser Ser Ile Asp Ile Glu Asn Gly Phe Ile Ser Glu Ser Gln
450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Arg Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
            515                 520                 525

Asn Asp Thr Leu Asp Tyr Glu Cys His Asp Gly Tyr Glu Ser Asn Thr
530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
            595                 600                 605

Val Gln Cys Tyr His Phe Gly Leu Ser Pro Asp Leu Pro Ile Cys Lys
            610                 615                 620

Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
            675                 680                 685

Ser Thr Cys Gly Asp Ile Pro Glu Leu Glu His Gly Trp Ala Gln Leu
            690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
            755                 760                 765

Lys Glu Phe Asp His Asn Ser Asn Ile Arg Tyr Arg Cys Arg Gly Lys
            770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
            835                 840                 845
```

```
Glu Glu Ile Thr Cys Lys Asp Gly Arg Trp Gln Ser Ile Pro Leu Cys
    850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro  Met Gly Glu Lys Lys  Asp Val Tyr
        995                 1000                 1005

Lys Ala  Gly Glu Gln Val Thr  Tyr Thr Cys Ala Thr  Tyr Tyr Lys
    1010                 1015                 1020

Met Asp  Gly Ala Ser Asn Val  Thr Cys Ile Asn Ser  Arg Trp Thr
    1025                 1030                 1035

Gly Arg  Pro Thr Cys Arg Asp  Thr Ser Cys Val Asn  Pro Pro Thr
    1040                 1045                 1050

Val Gln  Asn Ala Tyr Ile Val  Ser Arg Gln Met Ser  Lys Tyr Pro
    1055                 1060                 1065

Ser Gly  Glu Arg Val Arg Tyr  Gln Cys Arg Ser Pro  Tyr Glu Met
    1070                 1075                 1080

Phe Gly  Asp Glu Glu Val Met  Cys Leu Asn Gly Asn  Trp Thr Glu
    1085                 1090                 1095

Pro Pro  Gln Cys Lys Asp Ser  Thr Gly Lys Cys Gly  Pro Pro Pro
    1100                 1105                 1110

Pro Ile  Asp Asn Gly Asp Ile  Thr Ser Phe Pro Leu  Ser Val Tyr
    1115                 1120                 1125

Ala Pro  Ala Ser Ser Val Glu  Tyr Gln Cys Gln Asn  Leu Tyr Gln
    1130                 1135                 1140

Leu Glu  Gly Asn Lys Arg Ile  Thr Cys Arg Asn Gly  Gln Trp Ser
    1145                 1150                 1155

Glu Pro  Pro Lys Cys Leu His  Pro Cys Val Ile Ser  Arg Glu Ile
    1160                 1165                 1170

Met Glu  Asn Tyr Asn Ile Ala  Leu Arg Trp Thr Ala  Lys Gln Lys
    1175                 1180                 1185

Leu Tyr  Ser Arg Thr Gly Glu  Ser Val Glu Phe Val  Cys Lys Arg
    1190                 1195                 1200

Gly Tyr  Arg Leu Ser Ser Arg  Ser His Thr Leu Arg  Thr Thr Cys
    1205                 1210                 1215

Trp Asp  Gly Lys Leu Glu Tyr  Pro Thr Cys Ala Lys  Arg
    1220                 1225                 1230

<210> SEQ ID NO 3
<211> LENGTH: 1189
```

<212> TYPE: DNA
<213> ORGANISM: Homo sapiens

<400> SEQUENCE: 3

```
atgtggctcc tggtcagtgt aattctaatc tcacggatat cctctgttgg gggagaagca      60
acattttgtg attttccaaa aataaaccat ggaattctat atgatgaaga aaaatataag     120
ccattttccc aggttcctac aggggaagtt ttctattact cctgtgaata taattttgtg     180
tctccttcaa atcattttg gactcgcata acatgcacag aagaaggatg gtcaccaaca      240
ccaaagtgtc tcagactgtg tttctttcct tttgtggaaa atggtcattc tgaatcttca     300
ggacaaacac atctggaagg tgatactgtg caaattattt gcaacacagg atacagactt     360
caaaacaatg agaacaacat ttcatgtgta aacggggct ggtccacccc tcccaaatgc      420
aggtccactg acacttcctg tgtgaatccg cccacagtac aaaatgctta tatagtgtcg     480
agacagatga gtaaatatcc atctggtgag agagtacgtt atcaatgtag gagcccttat     540
gaaatgtttg gggatgaaga agtgatgtgt ttaaatggaa actggacgga accacctcaa     600
tgcaaagatt ctacgggaaa atgtgggccc cctccaccta ttgacaatgg ggacattact     660
tcattcccgt tgtcagtata tgctccagct tcatcagttg agtaccaatg ccagaacttg     720
tatcaacttg agggtaacaa gcgaataaca tgtagaaatg gacaatggtc agaaccacca     780
aaatgcttac atccgtgtgt aatatcccga gaaattatgg aaaattataa catagcatta     840
aggtggacag ccaaacagaa gctttatttg agaacaggtg aatcagctga atttgtgtgt     900
aaacggggat atcgtctttc atcacgttct cacacattgc gaacaacatg ttgggatggg     960
aaactggagt atccaacttg tgcaaaaaga tagaatcaat cataaaatgc acacctttat    1020
tcagaacttt agtattaaat cagttcttaa tttaattttt aagtattgtt ttactccttt    1080
ttattcatac gtaaaatttt ggattaattt gtgaaaatgt aattataagc tgagaccggt    1140
ggctctcttc ttaaaagcac catattaaaa cttggaaaac tggaaaact                1189
```

<210> SEQ ID NO 4
<211> LENGTH: 330
<212> TYPE: PRT
<213> ORGANISM: Homo sapiens

<400> SEQUENCE: 4

```
Met Trp Leu Leu Val Ser Val Ile Leu Ile Ser Arg Ile Ser Ser Val
1               5                   10                  15

Gly Gly Glu Ala Thr Phe Cys Asp Phe Pro Lys Ile Asn His Gly Ile
            20                  25                  30

Leu Tyr Asp Glu Glu Lys Tyr Lys Pro Phe Ser Gln Val Pro Thr Gly
        35                  40                  45

Glu Val Phe Tyr Tyr Ser Cys Glu Tyr Asn Phe Val Ser Pro Ser Lys
    50                  55                  60

Ser Phe Trp Thr Arg Ile Thr Cys Thr Glu Glu Gly Trp Ser Pro Thr
65                  70                  75                  80

Pro Lys Cys Leu Arg Leu Cys Phe Phe Pro Phe Val Glu Asn Gly His
                85                  90                  95

Ser Glu Ser Ser Gly Gln Thr His Leu Glu Gly Asp Thr Val Gln Ile
            100                 105                 110

Ile Cys Asn Thr Gly Tyr Arg Leu Gln Asn Asn Glu Asn Asn Ile Ser
        115                 120                 125

Cys Val Glu Arg Gly Trp Ser Thr Pro Pro Lys Cys Arg Ser Thr Asp
    130                 135                 140
```

```
Thr Ser Cys Val Asn Pro Pro Thr Val Gln Asn Ala Tyr Ile Val Ser
145                 150                 155                 160

Arg Gln Met Ser Lys Tyr Pro Ser Gly Glu Arg Val Arg Tyr Gln Cys
            165                 170                 175

Arg Ser Pro Tyr Glu Met Phe Gly Asp Glu Val Met Cys Leu Asn
        180                 185                 190

Gly Asn Trp Thr Glu Pro Pro Gln Cys Lys Asp Ser Thr Gly Lys Cys
            195                 200                 205

Gly Pro Pro Pro Ile Asp Asn Gly Asp Ile Thr Ser Phe Pro Leu
    210                 215                 220

Ser Val Tyr Ala Pro Ala Ser Ser Val Glu Tyr Gln Cys Gln Asn Leu
225                 230                 235                 240

Tyr Gln Leu Glu Gly Asn Lys Arg Ile Thr Cys Arg Asn Gly Gln Trp
            245                 250                 255

Ser Glu Pro Pro Lys Cys Leu His Pro Cys Val Ile Ser Arg Glu Ile
            260                 265                 270

Met Glu Asn Tyr Asn Ile Ala Leu Arg Trp Thr Ala Lys Gln Lys Leu
            275                 280                 285

Tyr Leu Arg Thr Gly Glu Ser Ala Glu Phe Val Cys Lys Arg Gly Tyr
    290                 295                 300

Arg Leu Ser Ser Arg Ser His Thr Leu Arg Thr Thr Cys Trp Asp Gly
305                 310                 315                 320

Lys Leu Glu Tyr Pro Thr Cys Ala Lys Arg
            325                 330

<210> SEQ ID NO 5
<211> LENGTH: 1246
<212> TYPE: DNA
<213> ORGANISM: Homo sapiens

<400> SEQUENCE: 5
atgttgttac taatcaatgt cattctgacc ttgtgggttt cctgtgctaa tggacaagtg      60
aaaccttgtg attttccaga cattaaacat ggaggtctat ttcatgagaa tatgcgtaga     120
ccatactttc cagtagctgt aggaaaatat tactcctatt actgtgatga acattttgag     180
actccgtcag gaagttactg ggattacatt cattgcacac aaaatgggtg gtcaccagca     240
gtaccatgtc tcagaaaatg ttatttttcct tatttggaaa atggatataa tcaaaattat     300
ggaagaaagt ttgtacaggg taactctaca gaagttgcct gccatcctgg ctacggtctt     360
ccaaaagtcc gtcagaccac agttacatgt acggagaatg gctggtctcc tactcccaga     420
tgcatccgag acagaacatg ctcaaaatca gatatagaaa ttgaaaatgg attcattct      480 gaatcttcct ctatttatat tttaaataaa gaaatacaat ataaatgtaa accaggatat     540
gcaacagcag atggaaattc ttcaggatca attacatgtt gcgaaatgg atggtcagca     600 caaccaattt gcattaattc ttcagaaaag tgtggacctc ctccacctat tagcaatggt     660
gataccacct cctttctact aaaagtgtat gtgccacagt caagagtcga gtaccaatgc     720
cagtcctact atgaacttca gggttctaat tatgtaacat gtagtaatgg agagtggtcg     780
gcaccaccta gatgcataca tccatgtata taactgaag aaaacatgaa taaaataac     840 ataagttaa aaggaagaag tgacagaaaa tattatgcaa aaacagggga taccattgaa     900
tttatgtgta aattgggata taatgcaaat acatcaattc tatcatttca agcagtgtgt     960
cgggaaggga tagtggaata ccccagatgc gaataaggca gcattgttac cctaaatgta    1020
```

```
tgtccaactt ccactttcc acttctcact cttatggtct caaagcttgc aaagatagct    1080
tctgatattg ttgtaatttc tactttattt caaagaaaat taatataata gtttcaattt    1140
gcaacttaat atattctcaa aaatatatta aacaaacta aattattgct tatgcttgta     1200 ctaaataat aaaaactact cttataaaaa aaaaaaaaa aaaaaa                     1246
```

<210> SEQ ID NO 6
<211> LENGTH: 331
<212> TYPE: PRT
<213> ORGANISM: Homo sapiens

<400> SEQUENCE: 6

```
Met Leu Leu Leu Ile Asn Val Ile Leu Thr Leu Trp Val Ser Cys Ala
1               5                   10                  15

Asn Gly Gln Val Lys Pro Cys Asp Phe Pro Asp Ile Lys His Gly Gly
                20                  25                  30

Leu Phe His Glu Asn Met Arg Arg Pro Tyr Phe Pro Val Ala Val Gly
            35                  40                  45

Lys Tyr Tyr Ser Tyr Tyr Cys Asp Glu His Phe Glu Thr Pro Ser Gly
        50                  55                  60

Ser Tyr Trp Asp Tyr Ile His Cys Thr Gln Asn Gly Trp Ser Pro Ala
65                  70                  75                  80

Val Pro Cys Leu Arg Lys Cys Tyr Phe Pro Tyr Leu Glu Asn Gly Tyr
                85                  90                  95

Asn Gln Asn Tyr Gly Arg Lys Phe Val Gln Gly Asn Ser Thr Glu Val
            100                 105                 110

Ala Cys His Pro Gly Tyr Gly Leu Pro Lys Val Arg Gln Thr Thr Val
        115                 120                 125

Thr Cys Thr Glu Asn Gly Trp Ser Pro Thr Pro Arg Cys Ile Arg Asp
130                 135                 140

Arg Thr Cys Ser Lys Ser Asp Ile Glu Ile Glu Asn Gly Phe Ile Ser
145                 150                 155                 160

Glu Ser Ser Ser Ile Tyr Ile Leu Asn Lys Glu Ile Gln Tyr Lys Cys
                165                 170                 175

Lys Pro Gly Tyr Ala Thr Ala Asp Gly Asn Ser Ser Gly Ser Ile Thr
            180                 185                 190

Cys Leu Arg Asn Gly Trp Ser Ala Gln Pro Ile Cys Ile Asn Ser Ser
        195                 200                 205

Glu Lys Cys Gly Pro Pro Pro Ile Ser Asn Gly Asp Thr Thr Ser
210                 215                 220

Phe Leu Leu Lys Val Tyr Val Pro Gln Ser Arg Val Glu Tyr Gln Cys
225                 230                 235                 240

Gln Ser Tyr Tyr Glu Leu Gln Gly Ser Asn Tyr Val Thr Cys Ser Asn
                245                 250                 255

Gly Glu Trp Ser Ala Pro Pro Arg Cys Ile His Pro Cys Ile Ile Thr
            260                 265                 270

Glu Glu Asn Met Asn Lys Asn Asn Ile Lys Leu Lys Gly Arg Ser Asp
        275                 280                 285

Arg Lys Tyr Tyr Ala Lys Thr Gly Asp Thr Ile Glu Phe Met Cys Lys
    290                 295                 300

Leu Gly Tyr Asn Ala Asn Thr Ser Ile Leu Ser Phe Gln Ala Val Cys
305                 310                 315                 320

Arg Glu Gly Ile Val Glu Tyr Pro Arg Cys Glu
                325                 330
```

```
<210> SEQ ID NO 7
<211> LENGTH: 17
<212> TYPE: DNA
<213> ORGANISM: Artificial
<220> FEATURE:
<223> OTHER INFORMATION: Synthetic CFHL1ex6.F, CFHR1 ex6 forward primer

<400> SEQUENCE: 7
agtcggtttg gacagtg                                                17

<210> SEQ ID NO 8
<211> LENGTH: 18
<212> TYPE: DNA
<213> ORGANISM: Artificial
<220> FEATURE:
<223> OTHER INFORMATION: Synthetic CFHL1ex6R, CFHR1 ex6 reverse primer

<400> SEQUENCE: 8
gcacaagttg gatactcc                                               18

<210> SEQ ID NO 9
<211> LENGTH: 20
<212> TYPE: DNA
<213> ORGANISM: Artificial
<220> FEATURE:
<223> OTHER INFORMATION: Synthetic CFHL1ex6. F2, CFHR1 (ex6) forward
      primer

<400> SEQUENCE: 9
catagtcggt ttggacagtg                                             20

<210> SEQ ID NO 10
<211> LENGTH: 19
<212> TYPE: DNA
<213> ORGANISM: Artificial
<220> FEATURE:
<223> OTHER INFORMATION: Synthetic CFHL3ex3.F, CFHR3 ex3 forward primer

<400> SEQUENCE: 10
tcattgctat gtccttagg                                              19

<210> SEQ ID NO 11
<211> LENGTH: 17
<212> TYPE: DNA
<213> ORGANISM: Artificial
<220> FEATURE:
<223> OTHER INFORMATION: Synthetic CFHL3ex3.R, CFHR3 ex3 reverse primer

<400> SEQUENCE: 11
tctgagactg tcgtccg                                                17

<210> SEQ ID NO 12
<211> LENGTH: 17
<212> TYPE: DNA
<213> ORGANISM: Artificial
<220> FEATURE:
<223> OTHER INFORMATION: Synthetic CFHL3ex3seq.F, CFHR3 ex3 seq forward
      primer

<400> SEQUENCE: 12
ttttggatgt ttatgcg                                                17

<210> SEQ ID NO 13
<211> LENGTH: 16
<212> TYPE: DNA
<213> ORGANISM: Artificial
```

```
<220> FEATURE:
<223> OTHER INFORMATION: Synthetic CFHL3ex3seq.R, CFHR3 ex3 seq reverse
      primer

<400> SEQUENCE: 13
aaataggtcc gttggc                                                   16

<210> SEQ ID NO 14
<211> LENGTH: 20
<212> TYPE: DNA
<213> ORGANISM: Artificial
<220> FEATURE:
<223> OTHER INFORMATION: Synthetic PCR primer CFH ex22 forward

<400> SEQUENCE: 14
ggtttggata gtgttttgag                                               20

<210> SEQ ID NO 15
<211> LENGTH: 17
<212> TYPE: DNA
<213> ORGANISM: Artificial
<220> FEATURE:
<223> OTHER INFORMATION: Synthetic PCR primer CFH ex22 reverse

<400> SEQUENCE: 15
accgttagtt ttccagg                                                  17

<210> SEQ ID NO 16
<211> LENGTH: 17
<212> TYPE: DNA
<213> ORGANISM: Artificial
<220> FEATURE:
<223> OTHER INFORMATION: Synthetic PCR primer CFHR2 ex4 forward

<400> SEQUENCE: 16
tgtgttcatt cagtgag                                                  17

<210> SEQ ID NO 17
<211> LENGTH: 17
<212> TYPE: DNA
<213> ORGANISM: Artificial
<220> FEATURE:
<223> OTHER INFORMATION: Synthetic PCR primer CFHR2 ex4 reverse

<400> SEQUENCE: 17
atagacattt ggtaggc                                                  17

<210> SEQ ID NO 18
<211> LENGTH: 20
<212> TYPE: DNA
<213> ORGANISM: Artificial
<220> FEATURE:
<223> OTHER INFORMATION: Synthetic PCR primer CFHR4 ex3 forward

<400> SEQUENCE: 18
ctacaatggg actttcttag                                               20

<210> SEQ ID NO 19
<211> LENGTH: 19
<212> TYPE: DNA
<213> ORGANISM: Artificial
<220> FEATURE:
<223> OTHER INFORMATION: Synthetic PCR primer CFHR4 ex3 reverse

<400> SEQUENCE: 19
ttcacactca taggaggac                                                19
```

<210> SEQ ID NO 20
<211> LENGTH: 16
<212> TYPE: DNA
<213> ORGANISM: Artificial
<220> FEATURE:
<223> OTHER INFORMATION: Synthetic PCR primer CFHR5 ex2 forward

<400> SEQUENCE: 20 aaccctttt cccaag                                                    16

<210> SEQ ID NO 21
<211> LENGTH: 19
<212> TYPE: DNA
<213> ORGANISM: Artificial
<220> FEATURE:
<223> OTHER INFORMATION: Synthetic PCR primer CFHR5 ex2 reverse

<400> SEQUENCE: 21
cacatccttc tctattcac                                                19

<210> SEQ ID NO 22
<211> LENGTH: 17
<212> TYPE: DNA
<213> ORGANISM: Artificial
<220> FEATURE:
<223> OTHER INFORMATION: Synthetic PCR primer CFH ex22 reverse

<400> SEQUENCE: 22
atgttgttcg caatgtg                                                  17

<210> SEQ ID NO 23
<211> LENGTH: 23
<212> TYPE: DNA
<213> ORGANISM: Artificial
<220> FEATURE:
<223> OTHER INFORMATION: Synthetic PCR primer IVS 5' to CFHR3 forward

<400> SEQUENCE: 23
cacgctattt gaaagacaaa ctt                                           23

<210> SEQ ID NO 24
<211> LENGTH: 22
<212> TYPE: DNA
<213> ORGANISM: Artificial
<220> FEATURE:
<223> OTHER INFORMATION: Synthetic PCR primer IVS 5' to CFHR3 reverse

<400> SEQUENCE: 24
aagcaaccct gctctacaat gt                                            22

<210> SEQ ID NO 25
<211> LENGTH: 20
<212> TYPE: DNA
<213> ORGANISM: Artificial
<220> FEATURE:
<223> OTHER INFORMATION: Synthetic PCR primer IVS 5' to CFHR3 forward

<400> SEQUENCE: 25
ggaaccacat gggtcaaatg                                               20

<210> SEQ ID NO 26
<211> LENGTH: 27
<212> TYPE: DNA
<213> ORGANISM: Artificial
<220> FEATURE:

```
<223> OTHER INFORMATION: Synthetic PCR primer IVS 5' to CFHR3 reverse

<400> SEQUENCE: 26
gcacaacaaa taaaactagc aaatcat                                          27

<210> SEQ ID NO 27
<211> LENGTH: 23
<212> TYPE: DNA
<213> ORGANISM: Artificial
<220> FEATURE:
<223> OTHER INFORMATION: Synthetic PCR primer IVS 5' to CFHR3 forward

<400> SEQUENCE: 27
attgctgcaa tctcagaaga aaa                                              23

<210> SEQ ID NO 28
<211> LENGTH: 22
<212> TYPE: DNA
<213> ORGANISM: Artificial
<220> FEATURE:
<223> OTHER INFORMATION: Synthetic PCR primer IVS 5' to CFHR3 reverse

<400> SEQUENCE: 28
tcaaaacgaa caaacaaaca gg                                               22

<210> SEQ ID NO 29
<211> LENGTH: 21
<212> TYPE: DNA
<213> ORGANISM: Artificial
<220> FEATURE:
<223> OTHER INFORMATION: Synthetic PCR primer CFHR3 (ex2) forward

<400> SEQUENCE: 29
tgcgtagacc atactttcca g                                                21

<210> SEQ ID NO 30
<211> LENGTH: 33
<212> TYPE: DNA
<213> ORGANISM: Artificial
<220> FEATURE:
<223> OTHER INFORMATION: Synthetic PCR primer CFHR3 (ex2) reverse

<400> SEQUENCE: 30
ctctctttaa tcttttaaag ttttatacat gtg                                   33

<210> SEQ ID NO 31
<211> LENGTH: 23
<212> TYPE: DNA
<213> ORGANISM: Artificial
<220> FEATURE:
<223> OTHER INFORMATION: Synthetic PCR primer CFHR1 (ex2) forward

<400> SEQUENCE: 31
taaagtgctg tgtttgtatt tgc                                              23

<210> SEQ ID NO 32
<211> LENGTH: 23
<212> TYPE: DNA
<213> ORGANISM: Artificial
<220> FEATURE:
<223> OTHER INFORMATION: Synthetic PCR primer CFHR1 (ex2) reverse

<400> SEQUENCE: 32
gtgattattt tgttaccaac agc                                              23
```

```
<210> SEQ ID NO 33
<211> LENGTH: 23
<212> TYPE: DNA
<213> ORGANISM: Artificial
<220> FEATURE:
<223> OTHER INFORMATION: Synthetic PCR primer CFHR2 forward

<400> SEQUENCE: 33
tccttttcta gttcattaac ata                                         23

<210> SEQ ID NO 34
<211> LENGTH: 21
<212> TYPE: DNA
<213> ORGANISM: Artificial
<220> FEATURE:
<223> OTHER INFORMATION: Synthetic PCR primer CFHR2 reverse

<400> SEQUENCE: 34
agtgatatga cacatgctga c                                           21

<210> SEQ ID NO 35
<211> LENGTH: 24
<212> TYPE: DNA
<213> ORGANISM: Artificial
<220> FEATURE:
<223> OTHER INFORMATION: Synthetic PCR primer CFHR2 forward

<400> SEQUENCE: 35
ctacagacta actttcaata attt                                        24

<210> SEQ ID NO 36
<211> LENGTH: 24
<212> TYPE: DNA
<213> ORGANISM: Artificial
<220> FEATURE:
<223> OTHER INFORMATION: Synthetic PCR primer CFHR2 reverse

<400> SEQUENCE: 36
gatactttta cattttctta tgat                                        24

<210> SEQ ID NO 37
<211> LENGTH: 25
<212> TYPE: DNA
<213> ORGANISM: Artificial
<220> FEATURE:
<223> OTHER INFORMATION: Synthetic PCR primer CFHR2 forward

<400> SEQUENCE: 37
acatagttat atgatcgttt tgagt                                       25

<210> SEQ ID NO 38
<211> LENGTH: 23
<212> TYPE: DNA
<213> ORGANISM: Artificial
<220> FEATURE:
<223> OTHER INFORMATION: Synthetic PCR primer CFHR2 reverse

<400> SEQUENCE: 38
acagagaaag aacttactaa ttg                                         23

<210> SEQ ID NO 39
<211> LENGTH: 22
<212> TYPE: DNA
<213> ORGANISM: Artificial
<220> FEATURE:
<223> OTHER INFORMATION: Synthetic PCR primer CFHR4 forward
```

-continued

```
<400> SEQUENCE: 39
agtattaaat tgttcagtcc ag                                                  22

<210> SEQ ID NO 40
<211> LENGTH: 23
<212> TYPE: DNA
<213> ORGANISM: Artificial
<220> FEATURE:
<223> OTHER INFORMATION: Synthetic PCR primer CFHR4 reverse

<400> SEQUENCE: 40
aaactagtgt aagaatgtat gat                                                 23

<210> SEQ ID NO 41
<211> LENGTH: 23
<212> TYPE: DNA
<213> ORGANISM: Artificial
<220> FEATURE:
<223> OTHER INFORMATION: Synthetic PCR primer CFHR4 forward

<400> SEQUENCE: 41
taagttgaaa gagatctaaa cac                                                 23

<210> SEQ ID NO 42
<211> LENGTH: 25
<212> TYPE: DNA
<213> ORGANISM: Artificial
<220> FEATURE:
<223> OTHER INFORMATION: Synthetic PCR primer CFHR4 reverse

<400> SEQUENCE: 42
actgtatgta agattatgaa agtat                                               25
```